US009771360B2

(12) United States Patent
Vakalopoulos et al.

(10) Patent No.: US 9,771,360 B2
(45) Date of Patent: Sep. 26, 2017

(54) CYANO-SUBSTITUTED IMIDAZO[1,2-A]PYRIDINECARBOXAMIDES AND THEIR USE

(71) Applicant: Bayer Pharma Aktiengesellschaft, Berlin (DE)

(72) Inventors: Alexandros Vakalopoulos, Hilden (DE); Philipp Buchgraber, Berlin (DE); Niels Lindner, Wuppertal (DE); Markus Follmann, Köln (DE); Frank Wunder, Wuppertal (DE); Johannes-Peter Stasch, Grottaferrata (IT); Tobias Marquardt, Wuppertal (DE); Gorden Redlich, Bochum (DE); Lisa Dietz, Wuppertal (DE); Volkhart Min-Jian Li, Velbert (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/120,377

(22) PCT Filed: Mar. 18, 2015

(86) PCT No.: PCT/EP2015/055642
§ 371 (c)(1),
(2) Date: Aug. 19, 2016

(87) PCT Pub. No.: WO2015/140199
PCT Pub. Date: Sep. 24, 2015

(65) Prior Publication Data
US 2017/0217954 A1   Aug. 3, 2017

(30) Foreign Application Priority Data

Mar. 21, 2014  (EP) .................................... 14161144

(51) Int. Cl.
| | | |
|---|---|---|
| *C07D 401/02* | (2006.01) | |
| *C07D 401/10* | (2006.01) | |
| *A61K 31/437* | (2006.01) | |
| *A61K 31/4353* | (2006.01) | |
| *C07D 471/04* | (2006.01) | |
| *A61K 45/06* | (2006.01) | |
| *A61K 31/444* | (2006.01) | |
| *A61K 31/4545* | (2006.01) | |

(52) U.S. Cl.
CPC .......... *C07D 471/04* (2013.01); *A61K 31/437* (2013.01); *A61K 31/444* (2013.01); *A61K 31/4545* (2013.01); *A61K 45/06* (2013.01)

(58) Field of Classification Search
CPC .. C07D 401/02; C07D 401/10; A61K 31/437; A61K 31/4353
USPC .......................................... 546/121; 514/300
See application file for complete search history.

(56) References Cited

U.S. PATENT DOCUMENTS

| 5,459,132 A | * | 10/1995 | Bru-Magniez ......... C07H 19/16 |
|---|---|---|---|
| | | | 514/46 |
| 5,593,993 A | | 1/1997 | Morin, Jr. et al. |
| 5,691,336 A | | 11/1997 | Dorn et al. |
| 5,698,704 A | | 12/1997 | Jackson |
| 5,935,984 A | | 8/1999 | Goldmann et al. |
| 6,180,656 B1 | | 1/2001 | Fürstner et al. |
| 6,403,588 B1 | | 6/2002 | Hayakawa et al. |
| 7,935,722 B2 | | 5/2011 | Fales et al. |
| 8,212,041 B2 | | 7/2012 | Albrecht et al. |
| 8,778,964 B2 | | 7/2014 | Vakalopoulos et al. |
| 8,796,305 B2 | | 8/2014 | Vakalopoulos et al. |
| 8,946,215 B2 | | 2/2015 | Vakalopoulos et al. |
| 8,969,045 B2 | | 3/2015 | Burkhardt et al. |
| 9,126,998 B2 | | 9/2015 | Vakalopoulos et al. |
| 9,278,968 B2 | | 3/2016 | Kurosaki et al. |
| 2004/0180896 A1 | | 9/2004 | Munson et al. |
| 2008/0051409 A1 | | 2/2008 | Gmeiner et al. |
| 2008/0103183 A1 | | 5/2008 | Ackermann et al. |
| 2009/0124612 A1 | | 5/2009 | Albrecht et al. |
| 2009/0233920 A1 | | 9/2009 | Breitenstein et al. |
| 2010/0063068 A1 | | 3/2010 | Pracitto et al. |
| 2012/0232099 A1 | | 9/2012 | Pracitto et al. |
| 2013/0065884 A1 | | 3/2013 | No et al. |
| 2013/0203751 A1 | | 8/2013 | Hübsch et al. |
| 2014/0088080 A1 | | 3/2014 | Koga et al. |
| 2014/0128372 A1 | | 5/2014 | Vakalopoulos et al. |

(Continued)

FOREIGN PATENT DOCUMENTS

DE   196 42 255 A1   4/1998
EP   0 266 890 A1   5/1988

(Continued)

OTHER PUBLICATIONS

Altuna-Urquijo et al., "A Convenient Synthesis of Pyridine and 2,2'-Bipyridine Derivatives," Tetrahedron, (2009), vol. 65, Issue 5, pp. 975-984.
Bai et al., "Lewis Acid Catalyzed Intramolecular [4+2] and [3+2] Cross-Cycloaddition of Alkynylcyclopropane Ketones with Carbonyl Compounds and Imines," Angewandte Chemie International Edition, (Apr. 23, 2012), vol. 51, Issue 17, pp. 4112-4116.
Bergmann et al., "Autoxidation, of Hexaethylbenzene," 644. Organic Fluorine Compounds. Part XXVII.* Fluorinated α-Aminoisobutyric Acids, Journal of the Chemical Society, (1963), pp. 3462-3463.
Bitler et al., "The Preparation and Properties of Crystalline Firefly Luciferin," Archives of Biochemistry and Biophysics, (1957), vol. 72, No. 2, pp. 358-368.

(Continued)

*Primary Examiner* — Niloofar Rahmani
(74) *Attorney, Agent, or Firm* — Buchanan Ingersoll & Rooney PC

(57) ABSTRACT

The present application relates to novel substituted imidazo[1,2-a]pyridine-3-carboxamides, to processes for preparation thereof, to the use thereof, alone or in combinations, for the treatment and/or prophylaxis of diseases, and to the use thereof for production of medicaments for the treatment and/or prophylaxis of diseases, especially for the treatment and/or prophylaxis of cardiovascular disorders.

7 Claims, No Drawings

(56) References Cited

U.S. PATENT DOCUMENTS

| | | |
|---|---|---|
| 2014/0179672 A1 | 6/2014 | Vakalopoulos et al. |
| 2015/0274719 A1 | 10/2015 | Vakalopoulos et al. |
| 2016/0122341 A1 | 5/2016 | Vakalopoulos et al. |
| 2016/0185775 A1 | 6/2016 | Vakalopoulos et al. |
| 2016/0347770 A1 | 12/2016 | Vakalopoulos et al. |
| 2016/0362408 A1 | 12/2016 | Vakalopoulos et al. |
| 2017/0050961 A1 | 2/2017 | Vakalopoulos et al. |
| 2017/0050962 A1 | 2/2017 | Vakalopoulos et al. |
| 2017/0057954 A1 | 3/2017 | Vakalopoulos et al. |

FOREIGN PATENT DOCUMENTS

| | | |
|---|---|---|
| EP | 1 277 754 A1 | 1/2003 |
| EP | 2 716 642 A1 | 4/2014 |
| JP | H01-258674 A | 10/1989 |
| WO | 89/03833 A1 | 5/1989 |
| WO | 96/34866 A1 | 11/1996 |
| WO | 98/16223 A1 | 4/1998 |
| WO | 2006/015737 A1 | 2/2006 |
| WO | 2006/117183 A1 | 11/2006 |
| WO | 2007/002181 A2 | 1/2007 |
| WO | 2008/008539 A2 | 1/2008 |
| WO | 2008/061626 A1 | 5/2008 |
| WO | 2008/082490 A2 | 7/2008 |
| WO | 2008/134553 A1 | 11/2008 |
| WO | 2010/030538 A2 | 3/2010 |
| WO | 2011/113606 A1 | 9/2011 |
| WO | 2011/141409 A1 | 11/2011 |
| WO | 2012/143796 A2 | 10/2012 |
| WO | 2012/165399 A1 | 12/2012 |
| WO | 2014/068099 A1 | 5/2014 |
| WO | 2015/018814 A1 | 2/2015 |
| WO | 2015/082411 A1 | 6/2015 |
| WO | 2015/124544 A1 | 8/2015 |
| WO | 2015/140199 A1 | 9/2015 |
| WO | 2015/140254 A1 | 9/2015 |
| WO | 2015/165931 A1 | 11/2015 |

OTHER PUBLICATIONS

Bodanszky et al., "The Practice of Peptide Synthesis," Second, Revised Edition, Springer-Verlag Berlin Heidelberg 1994, pp. 1-24.

Chen et al., "Radical Formation in the Oxidation of 2,2¢-Azo-2-methyl-6-heptene by Thianthrene Cation Radical," The Journal of Organic Chemistry, (1996), vol. 61, No. 14, pp. 4716-4719.

Chen et al., "Cyclic Guanosine Monophosphate Signalling Pathway in Pulmonary Arterial Hypertension," Vascular Pharmacology, (Mar. 2013), vol. 58, Issue 3, pp. 211-218.

Dembinski, "Recent Advances in the Mitsunobu Reaction: Modified Reagents and the Quest for Chromatography-Free Separation," European Journal of Organic Chemistry, (Jul. 2004), vol. 2004, Issue 13, pp. 2763-2772.

Deng et al., "Studies on Phosphoroheterocycle Chemistry II: A Simple and New Route to 1,3,2-Diazaphospholidine-4-thione 2-sulfide Derivatives," Synthesis, (2001), No. 16, pp. 2445-2449.

Gensini et al., "3-Azabicyclo[3.1.0]hex-1-ylamines by Ti-Mediated Intramolecular Reductive Cyclopropanation of α-(N-Allylamino)-Substituted N,N-Dialkylcarboxamides and Carbonitriles," European Journal of Organic Chemistry, (2002), vol. 2002, No. 15, pp. 2499-2507.

Glass et al., "Stimulation of Human Platelet Guanylate Cyclase by Fatty Acids," The Journal of Biological Chemistry, (Feb. 25, 1977), vol. 252, No. 4, pp. 1279-1285.

Greene et al., "The Role of Protective Groups in Organic Synthesis," Greene's Protective Groups in Organic Synthesis, Fourth Edition, (2007), pp. 1-15.

Hamill et al., "Improved Patch-Clamp Techniques for High-Resolution Current Recording from Cells and Cell-Free Membrane Patches," Pflügers Archiv, (1981), vol. 391, No. 2, pp. 85-100.

Hassan et al., "Aryl-Aryl Bond Formation One Century after the Discovery of the Ullmann Reaction," Chemical Reviews, (Mar. 8, 2002), vol. 102, No. 5, pp. 1359-1469.

Himmel et al., "Suitability of Commonly Used Excipients for Electrophysiological In-Vitro Safety Pharmacology Assessment of Effects on hERG Potassium Current and on Rabbit Purkinje Fiber Action Potential," Journal of Pharmacological and Toxicological Methods, (2007), vol. 56, No. 2, pp. 145-158.

Hiroi et al., "A Novel Method for Direct Construction of Indole Skeletons by Intramolecular Carbopalladation of Allenes Followed by Nucleophilic Substitution," Synlett, (2001, vol. 2001, No. 2, pp. 263-265.

-Hjørringgaard et al., "An Automatic Solid-Phase Synthesis of Peptaibols," The Journal of Organic Chemistry, (2009), vol. 74, No. 3, pp. 1329-1332.

Hoenicka et al., "Purified Soluble Guanylyl Cyclase Expressed in a Baculovirus/Sf9 System: Stimulation by YC-1, Nitric Oxide, and Carbon Monoxide," Journal of Molecular Medicine, (Jan. 1999), vol. 77, No. 1, pp. 14-23.

Hughes, "The Mitsunobu Reaction," Organic Reactions, (1992), vol. 42, Chapter 2, Published by John Wiley & Sons, Inc., pp. 335-395 and 636-656.

Johnson, "Invitation to Organic Chemistry," Jones and Bartlett: Mississauga, Canada, (1999), p. 24 (6 pages).

Ko et al., "YC-1, a Novel Activator of Platelet Guanylate Cyclase," Blood, (1994), vol. 84, No. 12, pp. 4226-4233.

Kozo et al., "Spontaneous Hypertension in Rats," Int Rev. Exp. Pathol, (1969), vol. 7, pp. 227-270.

Lasker et al., "Targeting Soluble Guanylate Cyclase for the Treatment of Pulmonary Hypertension," Expert Review of Respiratory Medicine, (Apr. 2011), vol. 5, Issue 2, pp. 153-161.

McConathy et al., "Radiolabeled Amino Acids for Tumor Imaging with PET: Radiosynthesis andB iological Evaluation of 2-Amino-3-[18F]fluoro-2-methylpropanoic Acid and 3-[18F]Fluoro-2-methyl-2-(methylamino)propanoic Acid," Journal of Medicinal Chemistry, (2002), vol. 45, No. 11, pp. 2240-2249.

Mikami et al., "Applications of the Tandem [2,3]-Wittig-Oxy-Cope Rearrangement to Syntheses of exo-Brevicomin and Oxocrinol. The Scope and Limitation of the Sigmatropic Sequences as a Synthetic Method for δ,ε-Unsaturated Ketones," Chemistry Letters, (1982), vol. 11, No. 9, pp. 1349-1352.

Mülsch et al., "Effect of YC-1, an NO-independent, superoxide-sensitive stimulator of soluble guanylyl cyclase, on smooth muscle responsiveness to nitrovasodilators," British Journal of Pharmacology, (1997), vol. 120, No. 4, pp. 681-689.

Ogrel et al., "Synthesis of 15N-Labelled D-Isovaline and α-Aminoisobutyric Acid," European Journal of Organic Chemistry, (Mar. 2000), vol. 2000, Issue 5, pp. 857-859.

Ostermann et al., "A Novel Class of Oral Direct Renin Inhibitors: Highly Potent 3,5-Disubstituted Piperidines Bearing a Tricyclic P3-P1 Pharmacophore," Journal of Medicinal Chemistry, (2013), vol. 56, No. 6, pp. 2196-2206.

Patani et a., "Bioisosterism: A Rational Approach in Drug Design," Chemical Reviews, (1996), vol. 96, No. 8, pp. 3147-3176.

Pettibone et al., "A Structurally Novel Stimulator of Guanylate Cyclase with Long-Lasting Hypotensive Activity in the Dog," European Journal of Pharmacology, (Oct. 22, 1985), vol. 116, No. 3, pp. 307-312.

Rubottom et al., "Preparation of Methyl Ketones by the Sequential Treatment of Carboxylic Acids with Methyllithium and Chlorotrimethylsilane," The Journal of Organic Chemistry, (1983), vol. 48, No. 9, pp. 1550-1552.

Scheel et al., "Introduction of a Modular Automated Voltage-Clamp Platform and Its Correlation with Manual Human Ether-Á-go-goRelated Gene Voltage-Clamp Data," ASSAY and Drug Development Technologies, (2011), vol. 9, No. 6, pp. 600-607.

Soler et al., "Betulinic Acid Derivatives: A New Class of Specific Inhibitors of Human Immunodeficiency Virus Type 1 Entry," Journal of Medicinal Chemistry, (1996), vol. 39, Issue 5, pp. 1069-1083.

Stasch et al., "Cardiovascular Actions of a Novel No-Independent Guanylyl Cyclase Stimulator, BAY 41-8543: in vivo Studies," British Journal of Pharmacology, (2002), vol. 135, No. 2, pp. 344-355.

(56) References Cited

OTHER PUBLICATIONS

Van Den Buuse, "Circadian Rhythms of Blood Pressure, Heart Rate, and Locomotor Activity in Spontaneously Hypertensive Rats as Measured with Radio-Telemetry," Physiology & Behavior, (Apr. 1994), vol. 55, Issue 4, pp. 783-787.
Weidmann et al., "2-[(2-Pyridylmethyl)sulfinyl]-1H-thieno[3,4-d]imidazoles. A Novel Class of Gastric H+/K+-ATPase Inhibitors," Journal of Medicinal Chemistry, (1992), vol. 35, No. 3, pp. 438-450.
Wermuth, "Molecular Variations Based on Isosteric Replacements," The Practice of Medical Chemistry, (1996), pp. 203-237.
Witte et al., "Experimental heart failure in rats: effects on cardiovascular circadian rhythms and on myocardial β-adrenergic signaling," Cardiovascular Research, (Aug. 2000), vol. 47, No. 2, pp. 350-358.
Wube et al., "Design, Synthesis and Antimycobacterial Activities of 1-Methyl-2-Alkenyl-4(1H)-Quinolones," Bioorganic & Medicinal Chemistry, (2011), vol. 19, No. 1, pp. 567-579.
Wunder et al., "A Cell-Based cGMP Assay Useful for Ultra-High-Throughput Screening and Identification of Modulators of the Nitric Oxide/cGMP Pathway," Analytical Biochemistry, (2005), vol. 339, No. 1, pp. 104-112.
Yu et al., "Vasorelaxant Effect of Isoliquiritigenin, a Novel Soluble Guanylate Cyclase Activator, in Rat Aorta," British Journal of Pharmacology, (Apr. 1995), vol. 114, No. 38, pp. 1587-1594.
Zhou et al., "Properties of HERG Channels Stably Expressed in HEK 293 Cells Studied at Physiological Temperature," Biophysical Journal, (1998), vol. 74, No. 1, pp. 230-241.
Notification of Transmittal of the International Search Report (Forms PCT/ISA/220 and PCT/ISA/210) and the Written Opinion of the International Searching Authority (Form PCT/ISA/237) issued on May 20, 2015 by the European Patent Office in the International Application No. PCT/EP2015/055642 with English Translation of the International Search Report and the Written Opinion of the International Searching Authority. (19 pages).

* cited by examiner

CYANO-SUBSTITUTED IMIDAZO[1,2-A]PYRIDINECARBOXAMIDES AND THEIR USE

The present application relates to novel substituted imidazo[1,2-a]pyridine-3-carboxamides, to processes for preparation thereof, to the use thereof, alone or in combinations, for the treatment and/or prophylaxis of diseases, and to the use thereof for production of medicaments for the treatment and/or prophylaxis of diseases, especially for the treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be classified into two groups either by structural features or by the type of ligands: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory centre. This is of central importance for the activation mechanism. NO is able to bind to the iron atom of haem and thus markedly increase the activity of the enzyme. Haem-free preparations cannot, by contrast, be stimulated by NO. Carbon monoxide (CO) is also able to bind to the central iron atom of haem, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the aforementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attack at the central iron atom of haem. In addition to the side effects, the development of tolerance is one of the crucial disadvantages of this mode of treatment.

In recent years, some substances have been described which stimulate soluble guanylate cyclase directly, i.e. without prior release of NO, such as, for example, 3-(5'-hydroxymethyl-2'-furyl)-1-benzylindazole [YC-1; Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223).

Various imidazo[1,2-a]pyridine derivatives which can be used for treating disorders are described, inter alia, in EP 0 266 890-A1, WO 89/03833-A1, JP 01258674-A [cf. Chem. Abstr. 112:178986], WO 96/34866-A1, EP 1 277 754-A1, WO 2006/015737-A1, WO 2008/008539-A2, WO 2008/082490-A2, WO 2008/134553-A1, WO 2010/030538-A2, WO 2011/113606-A1 and WO 2012/165399-A1.

It was an object of the present invention to provide novel substances which act as stimulators of soluble guanylate cyclase and are suitable as such for the treatment and/or prophylaxis of diseases.

The present invention provides compounds of the general formula (I)

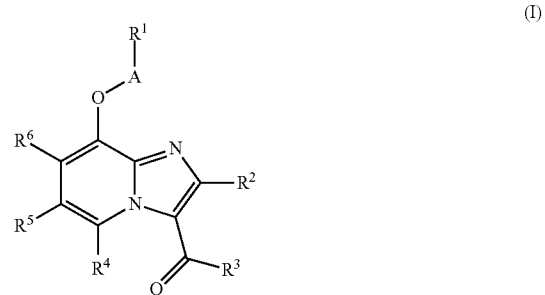

in which
A represents $CH_2$, $CD_2$ or $CH(CH_3)$,
$R^1$ represents $(C_4-C_6)$-alkyl, $(C_3-C_7)$-cycloalkyl, pyridyl or phenyl,
   where $(C_4-C_6)$-alkyl may be up to hexasubstituted by fluorine,
   where $(C_3-C_7)$-cycloalkyl may be substituted by 1 to 4 substituents independently of one another selected from the group consisting of fluorine, trifluoromethyl and $(C_1-C_4)$-alkyl, and
   where phenyl may be substituted by 1 to 4 substituents independently of one another selected from the group consisting of halogen, cyano, monofluoromethyl, difluoromethyl, trifluoromethyl, $(C_1-C_4)$-alkyl, $(C_3-C_5)$-cycloalkyl, $(C_1-C_4)$-alkoxy, difluoromethoxy and trifluoromethoxy, or may be substituted on two adjacent carbon atoms in the phenyl by a difluoromethylenedioxy bridge,
   where pyridyl may be substituted by 1 to 4 substituents independently of one another selected from the group consisting of fluorine, monofluoromethyl, difluoromethyl, trifluoromethyl and $(C_1-C_4)$-alkyl,
$R^2$ represents hydrogen, $(C_1-C_4)$-alkyl, cyclopropyl, monofluoromethyl, difluoromethyl or trifluoromethyl,
$R^3$ represents a group of the formula

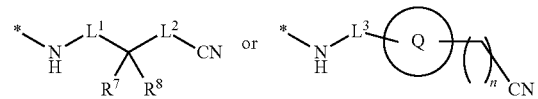

where
* represents the point of attachment to the carbonyl group,
$L^1$ represents a bond or $(C_1-C_4)$-alkanediyl,
   in which $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy, $L^2$ represents a bond or $(C_1-C_4)$-alkanediyl,
  in which $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$R^7$ represents hydrogen, $(C_1-C_6)$-alkyl, $(C_2-C_6)$-alkenyl, $(C_2-C_6)$-alkynyl, $(C_3-C_7)$-cycloalkyl, —(C═O)—NR$^9$R$^{10}$, $(C_1-C_4)$-alkoxycarbonyl, amino, hydroxy, 5- or 6-membered heteroaryl or phenyl,
  in which $(C_1-C_6)$-alkyl may be substituted by 1 to 3 substituents independently of one another selected from the group consisting of fluorine, trifluoromethyl, difluoromethoxy, trifluoromethoxy, hydroxy, $(C_3-C_7)$-cycloalkyl, $(C_1-C_4)$-alkoxy, $(C_1-C_4)$-alkoxycarbonyl, amino, phenyl, phenoxy and benzyloxy,
    in which phenyl, phenoxy and benzyloxy for their part may be substituted by 1 to 3 substituents independently of one another selected from the group consisting of halogen and cyano,
  in which $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
  in which
    $R^9$ represents hydrogen, $(C_1-C_6)$-alkyl or $(C_3-C_7)$-cycloalkyl,
    $R^{10}$ represents hydrogen or $(C_1-C_6)$-alkyl,
    and
  in which phenyl and 5- or 6-membered heteroaryl may be substituted by 1 to 3 substituents independently of one another selected from the group consisting of halogen, cyano, trifluoromethyl, $(C_1-C_4)$-alkyl, $(C_1-C_4)$-alkoxy and $(C_1-C_4)$-alkylsulphonyl,
$R^8$ represents hydrogen or $(C_1-C_4)$-alkyl,
  in which $(C_1-C_4)$-alkyl may be substituted by hydroxy,
or
$R^7$ and $R^8$ together with the carbon atom to which they are bonded form a 3- to 7-membered carbocycle or a 4- to 7-membered heterocycle,
  in which the 3- to 7-membered carbocycle and the 4- to 7-membered heterocycle may in turn be substituted by 1 or 2 substituents independently of one another selected from the group consisting of fluorine and $(C_1-C_4)$-alkyl,
$L^3$ represents a bond or $(C_1-C_4)$-alkanediyl,
  in which $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
n represents 0, 1 or 2,
the ring Q represents 3- to 7-membered carbocyclyl, 4- to 7-membered heterocyclyl, phenyl or 5- to 6-membered heteroaryl,
  where the ring Q may be substituted by 1 to 3 substituents independently of one another selected from the group consisting of halogen, $(C_1-C_4)$-alkyl, trifluoromethyl, amino, hydroxy and $(C_1-C_4)$-alkoxy,
$R^4$ represents hydrogen,
$R^5$ represents hydrogen, halogen, cyano, monofluoromethyl, difluoromethyl, trifluoromethyl, $(C_1-C_4)$-alkyl, $(C_3-C_7)$-cycloalkyl, $(C_2-C_4)$-alkenyl, $(C_2-C_4)$-alkynyl, difluoromethoxy, trifluoromethoxy, $(C_1-C_4)$-alkoxy, amino, 4- to 7-membered heterocyclyl or 5- or 6-membered heteroaryl, $R^6$ represents hydrogen, cyano or halogen,
and the N-oxides, salts, solvates, salts of the N-oxides and solvates of the N-oxides and salts thereof.
The present invention provides compounds of the general formula (I)
in which
A represents $CH_2$, $CD_2$ or $CH(CH_3)$,
$R^1$ represents $(C_4-C_6)$-alkyl, $(C_3-C_7)$-cycloalkyl, pyridyl or phenyl,
  where $(C_4-C_6)$-alkyl may be up to hexasubstituted by fluorine,
  where $(C_3-C_7)$-cycloalkyl may be substituted by 1 to 4 substituents independently of one another selected from the group consisting of fluorine, trifluoromethyl and $(C_1-C_4)$-alkyl,
  and
  where phenyl may be substituted by 1 to 4 substituents independently of one another selected from the group consisting of halogen, cyano, monofluoromethyl, difluoromethyl, trifluoromethyl, $(C_1-C_4)$-alkyl, $(C_3-C_5)$-cycloalkyl, $(C_1-C_4)$-alkoxy, difluoromethoxy and trifluoromethoxy, or may be substituted on two adjacent carbon atoms in the phenyl by a difluoromethylenedioxy bridge,
  where pyridyl may be substituted by 1 to 4 substituents independently of one another selected from the group consisting of fluorine, monofluoromethyl, difluoromethyl, trifluoromethyl and $(C_1-C_4)$-alkyl,
$R^2$ represents hydrogen, $(C_1-C_4)$-alkyl, cyclopropyl, monofluoromethyl, difluoromethyl or trifluoromethyl,
$R^3$ represents a group of the formula $$*\underset{H}{\overset{}{N}}\overset{L^1}{\diagdown}\underset{R^7\ R^8}{\overset{}{\diagup}}\overset{L^2}{\diagdown}CN \quad \text{or} \quad *\underset{H}{\overset{}{N}}\overset{L^3}{\diagdown}\left(Q\right)_n\diagdown CN$$

where
* represents the point of attachment to the carbonyl group,
$L^1$ represents a bond or $(C_1-C_4)$-alkanediyl,
  in which $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$L^2$ represents a bond or $(C_1-C_4)$-alkanediyl,
  in which $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$R^7$ represents hydrogen, $(C_1-C_6)$-alkyl, $(C_2-C_6)$-alkenyl, $(C_2-C_6)$-alkynyl, $(C_3-C_7)$-cycloalkyl, —(C═O)—NR$^9$R$^{10}$, $(C_1-C_4)$-alkoxycarbonyl, amino, hydroxy, 5- or 6-membered heteroaryl or phenyl,
  in which $(C_1-C_6)$-alkyl may be substituted by 1 to 3 substituents independently of one another selected from the group consisting of fluorine, trifluoromethyl, difluoromethoxy, trifluoromethoxy, hydroxy, $(C_3-C_7)$-cycloalkyl, $(C_1-C_4)$-alkoxy, $(C_1-C_4)$-alkoxycarbonyl, amino, phenyl, phenoxy and benzyloxy,
    in which phenyl, phenoxy and benzyloxy for their part may be substituted by 1 to 3 substituents independently of one another selected from the group consisting of halogen and cyano, in which $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy, in which $R^9$ represents hydrogen, $(C_1-C_6)$-alkyl or $(C_3-C_7)$-cycloalkyl, $R^{10}$ represents hydrogen or $(C_1-C_6)$-alkyl, and in which phenyl and 5- or 6-membered heteroaryl may be substituted by 1 to 3 substituents independently of one another selected from the group consisting of halogen, cyano, trifluoromethyl, $(C_1-C_4)$-alkyl, $(C_1-C_4)$-alkoxy and $(C_1-C_4)$-alkylsulphonyl, $R^8$ represents hydrogen or $(C_1-C_4)$-alkyl, in which $(C_1-C_4)$-alkyl may be substituted by hydroxy, Or $R^7$ and $R^8$ together with the carbon atom to which they are bonded form a 3- to 7-membered carbocycle or a 4- to 7-membered heterocycle, in which the 3- to 7-membered carbocycle and the 4- to 7-membered heterocycle may in turn be substituted by 1 or 2 substituents independently of one another selected from the group consisting of fluorine and $(C_1-C_4)$-alkyl, $L^3$ represents a bond or $(C_1-C_4)$-alkanediyl, in which $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy, n represents 0, 1 or 2, the ring Q represents 3- to 7-membered carbocyclyl, 4- to 7-membered heterocyclyl, phenyl or 5- to 6-membered heteroaryl, where the ring Q may be substituted by 1 to 3 substituents independently of one another selected from the group consisting of halogen, $(C_1-C_4)$-alkyl, trifluoromethyl and $(C_1-C_4)$-alkoxy, $R^4$ represents hydrogen, $R^5$ represents hydrogen, halogen, cyano, monofluoromethyl, difluoromethyl, trifluoromethyl, $(C_1-C_4)$-alkyl, $(C_3-C_7)$-cycloalkyl, $(C_2-C_4)$-alkenyl, $(C_2-C_4)$-alkynyl, difluoromethoxy, trifluoromethoxy, $(C_1-C_4)$-alkoxy, amino, 4- to 7-membered heterocyclyl or 5- or 6-membered heteroaryl, $R^6$ represents hydrogen, cyano or halogen, and the N-oxides, salts, solvates, salts of the N-oxides and solvates of the N-oxides and salts thereof.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are mentioned below as working examples and the salts, solvates and solvates of the salts thereof if the compounds that are encompassed by formula (I) and are mentioned below are not already salts, solvates and solvates of the salts.

Preferred salts in the context of the present invention are physiologically acceptable salts of the compounds of the invention. Also encompassed are salts which are not themselves suitable for pharmaceutical applications but can be used, for example, for isolation or purification of the compounds according to the invention.

Physiologically acceptable salts of the compounds of the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The compounds according to the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatographic processes are preferably used for this purpose, especially HPLC chromatography on an achiral or chiral phase.

If the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass from the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium) $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds of the invention can be prepared by the processes known to those skilled in the art, for example by the methods described further down and the procedures described in the working examples, by using corresponding isotopic modifications of the respective reagents and/or starting materials.

The present invention additionally also encompasses prodrugs of the compounds according to the invention. The term "prodrugs" in this context refers to compounds which may themselves be biologically active or inactive but are reacted (for example metabolically or hydrolytically) to give compounds according to the invention during their residence time in the body.

In the context of the present invention, unless specified otherwise, the substituents are defined as follows:

Alkyl in the context of the invention is a straight-chain or branched alkyl radical having the particular number of carbon atoms specified. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl.

Carbocycle or cycloalkyl in the context of the invention is a mono- or bicyclic saturated or partially unsaturated carbocycle having the number of ring carbon atoms stated in each case and up to 3 double bonds. The following may be mentioned by way of example and by way of preference: cyclopropyl, cyclobutyl, cyclopentyl, cyclohexyl, cycloheptyl, cyclopentenyl, cyclohexenyl, cyclohexadienyl, cycloheptenyl, cycloheptadienyl, indanyl, tetralinyl.

Alkenyl in the context of the invention is a straight-chain or branched alkenyl radical having 2 to 6 carbon atoms and one or two double bonds. Preference is given to a straight-chain or branched alkenyl radical having 2 to 4 carbon atoms and one double bond. The following may be mentioned by way of example and by way of preference: vinyl, allyl, isopropenyl and n-but-2-en-1-yl.

Alkynyl in the context of the invention is a straight-chain or branched alkynyl radical having 2 to 6 carbon atoms and one triple bond. The following may be mentioned by way of example and by way of preference: ethynyl, n-prop-1-yn-1-yl, n-prop-2-yn-1-yl, n-but-2-yn-1-yl and n-but-3-yn-1-yl.

Alkanediyl in the context of the invention is a straight-chain or branched divalent alkyl radical having 1 to 4 carbon atoms. The following may be mentioned by way of example and by way of preference: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl and butane-2,3-diyl.

Alkoxy in the context of the invention is a straight-chain or branched alkoxy radical having 1 to 4 carbon atoms. The following may be mentioned by way of example and by way of preference: methoxy, ethoxy, n-propoxy, isopropoxy, 1-methylpropoxy, n-butoxy, isobutoxy and tert-butoxy.

Alkoxycarbonyl in the context of the invention is a straight-chain or branched alkoxy radical having 1 to 4 carbon atoms and a carbonyl group attached to the oxygen. The following may be mentioned by way of example and by way of preference: methoxycarbonyl, ethoxycarbonyl, n-propoxycarbonyl, isopropoxycarbonyl and tert-butoxycarbonyl.

Alkylthio in the context of the invention is a thio group having a straight-chain or branched alkyl substituent having 1 to 4 carbon atoms. The following may be mentioned by way of example and by way of preference: methylthio, ethylthio, n-propylthio, isopropylthio, n-butylthio and tert-butylthio.

Alkylsulphonyl in the context of the invention is a straight-chain or branched alkyl radical which has 1 to 4 carbon atoms and is bonded via a sulphonyl group. The following may be mentioned by way of example and by way of preference: methylsulphonyl, ethylsulphonyl, n-propylsulphonyl, isopropylsulphonyl, n-butylsulphonyl and tert-butylsulphonyl.

Monoalkylamino in the context of the invention is an amino group having a straight-chain or branched alkyl substituent having 1 to 4 carbon atoms. The following may be mentioned by way of example and by way of preference: methylamino, ethylamino, n-propylamino, isopropylamino and tert-butylamino.

Dialkylamino in the context of the invention is an amino group having two identical or different straight-chain or branched alkyl substituents each having 1 to 4 carbon atoms. The following may be mentioned by way of example and by way of preference: N,N-dimethylamino, N,N-diethylamino, N-ethyl-N-methylamino, N-methyl-N-n-propylamino, N-isopropyl-N-n-propylamino and N-tert-butyl-N-methylamino.

A 4- to 7-membered heterocycle in the context of the invention is a monocyclic saturated heterocycle which has a total of 4 to 7 ring atoms, contains one or two ring heteroatoms from the group consisting of N, O, S, SO and $SO_2$ and is joined via a ring carbon atom or optionally a ring nitrogen atom. The following may be mentioned by way of example: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to azetidinyl, oxetanyl, pyrrolidinyl, tetrahydrofuranyl, piperidinyl, piperazinyl, tetrahydropyranyl and morpholinyl.

Heteroaryl in the context of the invention is a monocyclic aromatic heterocycle (heteroaromatic) which has a total of 5 or 6 ring atoms, contains up to three identical or different ring heteroatoms from the group consisting of N, O and S and is joined via a ring carbon atom or optionally via a ring nitrogen atom. The following may be mentioned by way of example and by way of preference: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl.

Halogen in the context of the invention includes fluorine, chlorine, bromine and iodine. Preference is given to chlorine or fluorine.

An oxo substituent in the context of the invention is an oxygen atom attached to a carbon or sulphur atom via a double bond.

In the formula of the group that $R^3$ or $R^1$ may represent, the end point of the line marked by the symbol * and # does not represent a carbon atom or a $CH_2$ group but is part of the bond to the respectively denoted atom to which $R^3$ or $R^1$ is attached.

When radicals in the compounds according to the invention are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In the context of the present invention, preference is given to compounds of the formula (I) in which
A represents $CH_2$ or $CH(CH_3)$,
$R^1$ represents $(C_4-C_6)$-alkyl, $(C_4-C_6)$-cycloalkyl, pyridyl or phenyl,
  where $(C_4-C_6)$-alkyl may be up to hexasubstituted by fluorine,
  where $(C_4-C_6)$-cycloalkyl may be substituted by 1 to 4 fluorine substituents,
  and
  where phenyl may be substituted by 1 to 3 substituents independently of one another selected from the group consisting of fluorine, chlorine, cyano, trifluoromethyl, methyl, cyclopropyl, methoxy and ethoxy,
  where pyridyl may be substituted by 1 or 2 substituents,
$R^2$ represents hydrogen, $(C_1-C_4)$-alkyl, cyclopropyl or trifluoromethyl,
$R^3$ represents a group of the formula

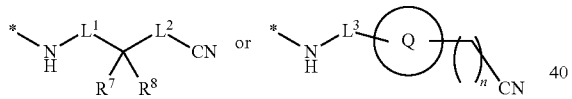

where
* represents the point of attachment to the carbonyl group,
$L^1$ represents a bond or $(C_1-C_4)$-alkanediyl,
  in which $(C_1-C_4)$-alkanediyl may be substituted by 1 or 2 substituents independently of one another selected from the group consisting of fluorine, trifluoromethyl, methyl and ethyl,
$L^2$ represents a bond, methylene, ethylene or propylene,
$R^7$ represents hydrogen, $(C_1-C_6)$-alkyl, $(C_3-C_5)$-cycloalkyl, —(C=O)—$NR^9R^{10}$, amino or phenyl,
  in which $(C_1-C_6)$-alkyl may be substituted by 1 to 3 substituents independently of one another selected from the group consisting of fluorine, trifluoromethyl, hydroxy, methoxy, ethoxy, amino and phenyl,
    in which phenyl may be substituted by 1 to 3 fluorine substituents,
  in which $(C_3-C_5)$-cycloalkyl may be substituted by 1 or 2 fluorine substituents,
  in which
    $R^9$ represents hydrogen, $(C_1-C_4)$-alkyl, cyclopropyl or cyclobutyl,
    $R^{10}$ represents hydrogen or $(C_1-C_4)$-alkyl,
    and
    in which phenyl may be substituted by 1 to 3 substituents independently of one another selected from the group consisting of fluorine, chlorine, cyano, trifluoromethyl, methyl, ethyl, methoxy and ethoxy,
$R^8$ represents hydrogen or $(C_1-C_4)$-alkyl,
or
$R^7$ and $R^8$ together with the carbon atom to which they are bonded form a 3- to 6-membered carbocycle,
  in which the 3- to 6-membered carbocycle may be substituted by 1 or 2 fluorine substituents,
$L^3$ represents a bond, methylene or ethylene,
  in which methylene and ethylene may be substituted by 1 or 2 substituents independently of one another selected from the group consisting of fluorine, methyl, ethyl and trifluoromethyl,
n represents 0 or 1,
the ring Q represents cyclopentyl, cyclohexyl, piperidinyl, piperazinyl, phenyl, pyrazolyl, pyridyl, oxazolyl, isoxazolyl, thiazolyl, oxadiazolyl or triazolyl,
  in which the ring Q may be substituted by 1 or 2 substituents independently of one another selected from the group consisting of fluorine, chlorine, methyl, ethyl, trifluoromethyl, methoxy and ethoxy,
$R^4$ represents hydrogen,
$R^5$ represents hydrogen, fluorine, bromine, chlorine, cyano, methyl, ethyl, cyclopropyl, ethynyl, methoxy or ethoxy,
$R^6$ represents hydrogen or fluorine,
and the N-oxides, salts, solvates, salts of the N-oxides and solvates of the N-oxides and salts thereof.

Particular preference is given in the context of the present invention to compounds of the formula (I) in which
A represents $CH_2$,
$R^1$ represents 3-methylbutyl,
  where 3-methylbutyl may be up to hexasubstituted by fluorine,
or
represents cyclohexyl,
  where cyclohexyl may be substituted by 2 fluorine substituents,
or
represents a phenyl group of the formula

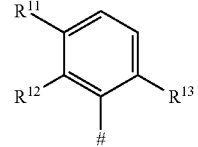

where
# represents the point of attachment to A,
and
$R^{11}$ represents hydrogen or fluorine,
$R^{12}$ and $R^{13}$ represent fluorine,
or
represents a pyridyl group of the formula

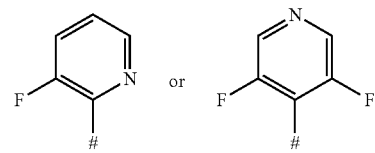

where
# represents the point of attachment to A,
$R^2$ represents methyl,
$R^3$ represents a group of the formula

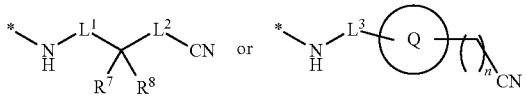

where
* represents the point of attachment to the carbonyl group,
$L^1$ represents a bond, methylene or ethylene,
$L^2$ represents a bond, methylene, ethylene or propylene,
$R^7$ represents hydrogen, methyl, ethyl, propyl, cyclopropyl, —(C=O)—$NR^9R^{10}$, amino or phenyl,
  in which methyl, ethyl and propyl may be substituted by hydroxy, methoxy, ethoxy or amino,
  in which cyclopropyl may be substituted by 1 or 2 fluorine substituents,
  in which
  $R^9$ represents hydrogen,
  $R^{10}$ represents hydrogen,
  and
  in which phenyl may be substituted by chlorine,
$R^8$ represents hydrogen or methyl,
or
$R^7$ and $R^8$ together with the carbon atom to which they are attached form a cyclopropyl ring or a cyclobutyl ring,
$L^3$ represents a bond or methylene,
n represents 0 or 1,
the ring Q represents cyclohexyl, piperidinyl, phenyl or pyrazolyl,
  in which the ring Q may be substituted by methoxy or ethoxy,
$R^4$ represents hydrogen,
$R^5$ represents hydrogen, chlorine, methyl, cyclopropyl or methoxy,
$R^6$ represents hydrogen,
and the N-oxides, salts, solvates, salts of the N-oxides and solvates of the N-oxides and salts thereof.

Particular preference is given in the context of the present invention to compounds of the formula (I) in which
A represents $CH_2$,
$R^1$ represents a phenyl group of the formula

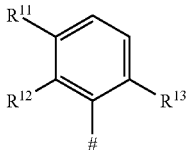

where
# represents the point of attachment to A,
and
$R^{11}$ represents hydrogen,
$R^{12}$ and $R^{13}$ represent fluorine,
$R^2$ represents methyl,
$R^3$ represents a group of the formula

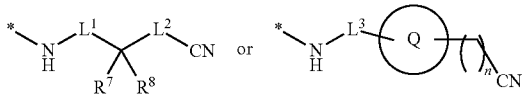

where
* represents the point of attachment to the carbonyl group,
$L^1$ represents a bond, methylene or ethylene,
$L^2$ represents a bond, methylene or ethylene,
$R^7$ represents hydrogen, methyl, ethyl, cyclopropyl, —(C=O)—$NR^9R^{10}$, amino or phenyl,
  in which methyl and ethyl may be substituted by hydroxy, methoxy, ethoxy or amino,
  in which
  $R^9$ represents hydrogen,
  $R^{10}$ represents hydrogen,
  and
  in which phenyl may be substituted by chlorine,
$R^8$ represents hydrogen or methyl,
or
$R^7$ and $R^8$ together with the carbon atom to which they are attached form a cyclopropyl ring or a cyclobutyl ring,
$L^3$ represents a bond or methylene,
n represents 0 or 1,
the ring Q represents cyclohexyl, piperidin-3-yl, phenyl or 1H-pyrazol-5-yl,
  in which phenyl may be substituted by methoxy or ethoxy,
$R^4$ represents hydrogen,
$R^5$ represents hydrogen, chlorine, methyl or methoxy,
$R^6$ represents hydrogen,
and the N-oxides, salts, solvates, salts of the N-oxides and solvates of the N-oxides and salts thereof.

In the context of the present invention, preference is also given to compounds of the formula (I) in which
A represents $CH_2$,
and the N-oxides, salts, solvates, salts of the N-oxides and solvates of the N-oxides and salts thereof.

In the context of the present invention, preference is also given to compounds of the formula (I) in which
$R^1$ represents 3-methylbutyl,
  where 3-methylbutyl may be up to hexasubstituted by fluorine,
or
represents cyclohexyl,
  where cyclohexyl may be substituted by 2 fluorine substituents,
or
represents a phenyl group of the formula

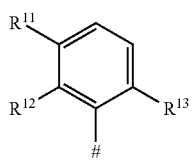

where
# represents the point of attachment to A,
and
$R^{11}$ represents hydrogen or fluorine,
$R^{12}$ and $R^{13}$ represent fluorine,
or
represents a pyridyl group of the formula

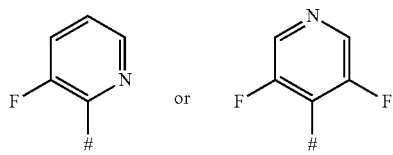

where
# represents the point of attachment to A,
and the N-oxides, salts, solvates, salts of the N-oxides and solvates of the N-oxides and salts thereof.

In the context of the present invention, preference is also given to compounds of the formula (I) in which
R¹ represents 3-methylbutyl,
where 3-methylbutyl may be up to hexasubstituted by fluorine,
and the N-oxides, salts, solvates, salts of the N-oxides and solvates of the N-oxides and salts thereof.

In the context of the present invention, preference is also given to compounds of the formula (I) in which
R¹ represents cyclohexyl,
where cyclohexyl may be substituted by 2 fluorine substituents,
and the N-oxides, salts, solvates, salts of the N-oxides and solvates of the N-oxides and salts thereof.

In the context of the present invention, preference is also given to compounds of the formula (I) in which
R¹ represents a phenyl group of the formula

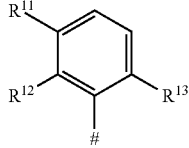

where
# represents the point of attachment to A,
and
R¹¹ represents hydrogen or fluorine,
R¹² and R¹³ represent fluorine,
and the N-oxides, salts, solvates, salts of the N-oxides and solvates of the N-oxides and salts thereof.

In the context of the present invention, preference is also given to compounds of the formula (I) in which
R¹ represents a phenyl group of the formula

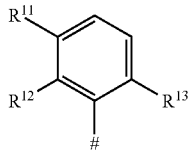

where
# represents the point of attachment to A,
and
R¹¹ represents hydrogen,
R¹² and R¹³ represent fluorine,
and the N-oxides, salts, solvates, salts of the N-oxides and solvates of the N-oxides and salts thereof.

In the context of the present invention, preference is also given to compounds of the formula (I) in which
R¹ represents a phenyl group of the formula

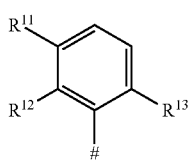

where
# represents the point of attachment to A,
and
R¹¹ represents fluorine,
R¹² and R¹³ represent fluorine,
and the N-oxides, salts, solvates, salts of the N-oxides and solvates of the N-oxides and salts thereof.

In the context of the present invention, preference is also given to compounds of the formula (I) in which
R¹ represents a pyridyl group of the formula

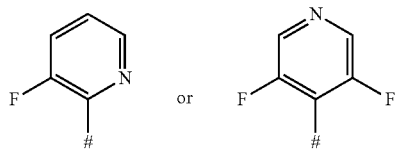

where
# represents the point of attachment to A,
and the N-oxides, salts, solvates, salts of the N-oxides and solvates of the N-oxides and salts thereof.

In the context of the present invention, preference is also given to compounds of the formula (I) in which
R² represents methyl,
and the N-oxides, salts, solvates, salts of the N-oxides and solvates of the N-oxides and salts thereof.

In the context of the present invention, preference is also given to compounds of the formula (I) in which
R³ represents a group of the formula

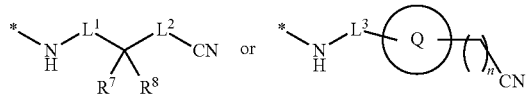

where
* represents the point of attachment to the carbonyl group,
L¹ represents a bond, methylene or ethylene,
L² represents a bond, methylene, ethylene or propylene,
R⁷ represents hydrogen, methyl, ethyl, propyl, cyclopropyl, —(C═O)—NR⁹R¹⁰, amino or phenyl,
in which (C₁-C₄)-alkyl may be substituted by hydroxy, methoxy, ethoxy or amino,
in which cyclopropyl may be substituted by 1 or 2 fluorine substituents,
in which
R⁹ represents hydrogen,
R¹⁰ represents hydrogen,
and
in which phenyl may be substituted by chlorine,
R⁸ represents hydrogen or methyl,
or
R⁷ and R⁸ together with the carbon atom to which they are attached form a cyclopropyl ring or a cyclobutyl ring,
L³ represents a bond or methylene,
n represents 0 or 1,
the ring Q represents cyclohexyl, piperidinyl, phenyl or pyrazolyl,
in which the ring Q may be substituted by methoxy or ethoxy,
and the N-oxides, salts, solvates, salts of the N-oxides and solvates of the N-oxides and salts thereof.

In the context of the present invention, preference is also given to compounds of the formula (I) in which R³ represents a group of the formula

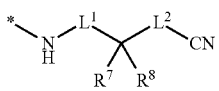

where
\* represents the point of attachment to the carbonyl group,
L¹ represents a bond, methylene or ethylene,
L² represents a bond, methylene, ethylene or propylene,
R⁷ represents hydrogen, methyl, ethyl, propyl, cyclopropyl, —(C=O)—NR⁹R¹⁰, amino or phenyl,
in which $(C_1-C_4)$-alkyl may be substituted by hydroxy, methoxy, ethoxy or amino,
in which cyclopropyl may be substituted by 1 or 2 fluorine substituents,
in which
R⁹ represents hydrogen,
R¹⁰ represents hydrogen,
and
in which phenyl may be substituted by chlorine,
R⁸ represents hydrogen or methyl,
or
R⁷ and R⁸ together with the carbon atom to which they are attached form a cyclopropyl ring or a cyclobutyl ring,
and the N-oxides, salts, solvates, salts of the N-oxides and solvates of the N-oxides and salts thereof.

In the context of the present invention, preference is also given to compounds of the formula (I) in which
R³ represents a group of the formula

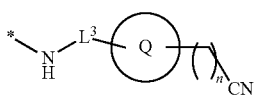

where
\* represents the point of attachment to the carbonyl group,
L³ represents a bond or methylene,
n represents 0 or 1,
the ring Q represents cyclohexyl, piperidinyl, phenyl or pyrazolyl,
in which the ring Q may be substituted by methoxy or ethoxy,
and the N-oxides, salts, solvates, salts of the N-oxides and solvates of the N-oxides and salts thereof.

In the context of the present invention, preference is also given to compounds of the formula (I) in which
R³ represents a group of the formula

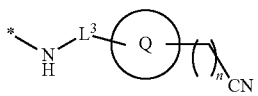

where
\* represents the point of attachment to the carbonyl group,
L³ represents a bond or methylene,
n represents 0 or 1,
the ring Q represents cyclohexyl, piperidin-3-yl, phenyl or 1H-pyrazol-5-yl,
in which phenyl may be substituted by methoxy or ethoxy, and the N-oxides, salts, solvates, salts of the N-oxides and solvates of the N-oxides and salts thereof.

In the context of the present invention, preference is also given to compounds of the formula (I) in which
R⁵ represents hydrogen, chlorine, methyl or methoxy,
and the N-oxides, salts, solvates, salts of the N-oxides and solvates of the N-oxides and salts thereof.

In the context of the present invention, preference is also given to compounds of the formula (I) in which
R⁵ represents hydrogen,
and the N-oxides, salts, solvates, salts of the N-oxides and solvates of the N-oxides and salts thereof.

In the context of the present invention, preference is also given to compounds of the formula (I) in which
R⁵ represents chlorine,
and the N-oxides, salts, solvates, salts of the N-oxides and solvates of the N-oxides and salts thereof.

In the context of the present invention, preference is also given to compounds of the formula (I) in which
R⁵ represents methyl,
and the N-oxides, salts, solvates, salts of the N-oxides and solvates of the N-oxides and salts thereof.

In the context of the present invention, preference is also given to compounds of the formula (I) in which
R⁵ represents methoxy,
and the N-oxides, salts, solvates, salts of the N-oxides and solvates of the N-oxides and salts thereof.

The invention further provides a process for preparing the compounds of the formula (I) according to the invention, characterized in that
[A] a compound of the formula (II)

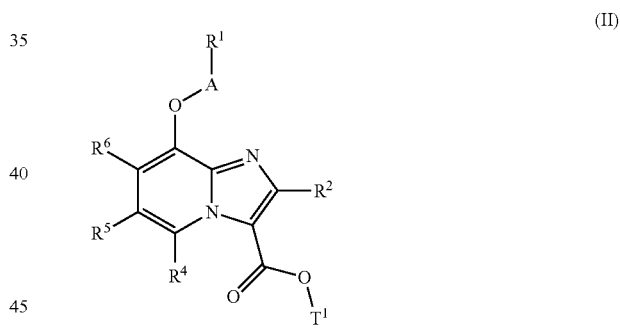

in which A, R¹, R², R⁴, R⁵ and R⁶ are each as defined above and
T¹ represents $(C_1-C_4)$-alkyl or benzyl,
is reacted in an inert solvent in the presence of a suitable base or acid to give a carboxylic acid of the formula (III)

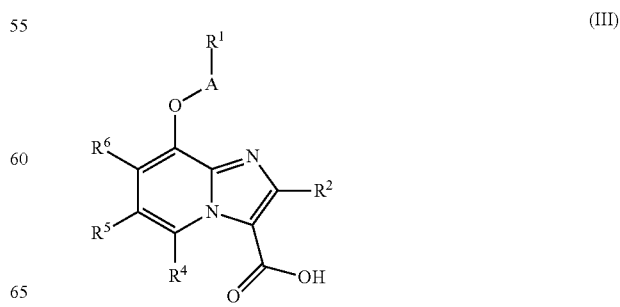

in which A, $R^1$, $R^2$, $R^4$, $R^5$ and $R^6$ each have the meanings given above, and this is subsequently reacted in an inert solvent under amide coupling conditions with an amine of the formula (IV-A) or (IV-B)

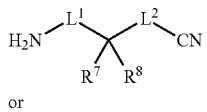
(IV-A)

or

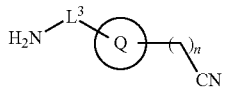
(IV-B)

in which n, $L^1$, $L^2$, $L^3$, Q, $R^7$ and $R^8$ each have the meanings given above, or

[B] a compound of the formula (III-B)

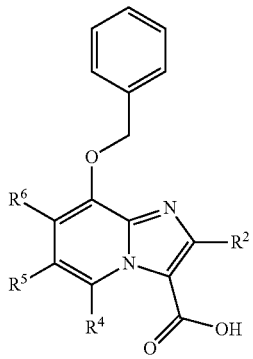
(III-B)

in which $R^2$, $R^4$, $R^5$ and $R^6$ each have the meanings given above, is reacted in an inert solvent under amide coupling conditions with an amine of the formula (IV) to give a compound of the formula (I-A) and (I-B)

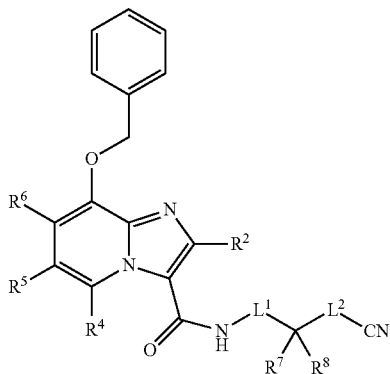
(I-A)

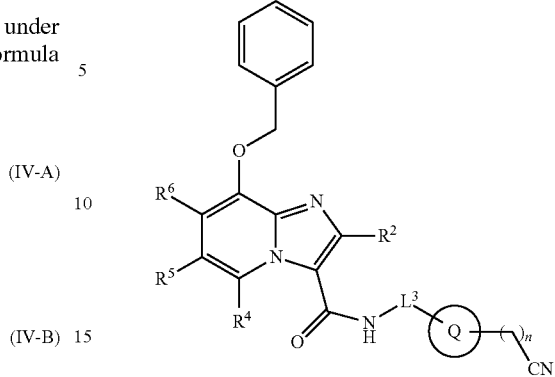
(I-B)

in which $R^2$, $R^4$, $R^5$, $R^6$, n, $L^1$, $L^2$, $L^3$, Q, $R^7$ and $R^8$ each have the meanings given above, and the benzyl group is subsequently detached therefrom by the methods known to the person skilled in the art and the resulting compound of the formula (V-A) or (V-B)

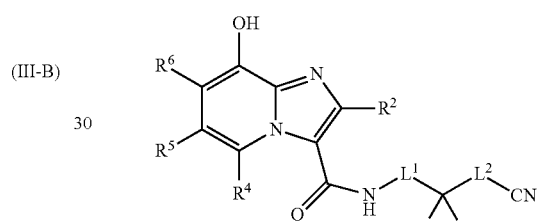
(V-A)

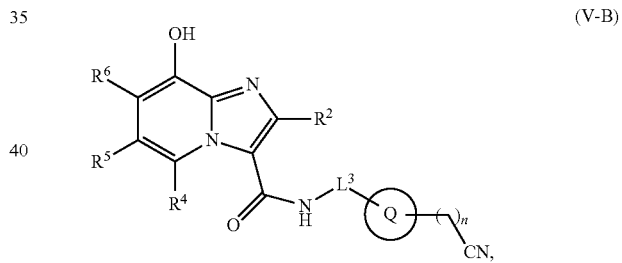
(V-B)

in which $R^2$, $R^4$, $R^5$, $R^6$, n, $L^1$, $L^2$, $L^3$, Q, $R^7$ and $R^8$ each have the meanings given above, is reacted in an inert solvent in the presence of a suitable base with a compound of the formula (VI)

(VI)

in which A and $R^1$ have the meaning given above and
$X^1$ represents a suitable leaving group, in particular chlorine, bromine, iodine, mesylate, triflate or tosylate,
then any protective groups present are detached, and the resulting compounds of the formula (I) are optionally converted with the appropriate (i) solvents and/or (ii) acids or bases to the solvates, salts and/or solvates of the salts thereof.

The compounds of the formulae (I-A) and (I-B) form a subset of the compounds of the formula (I) according to the invention.

The preparation processes described can be illustrated by way of example by the following synthesis schemes (Schemes 1 and 2):

Scheme 1:

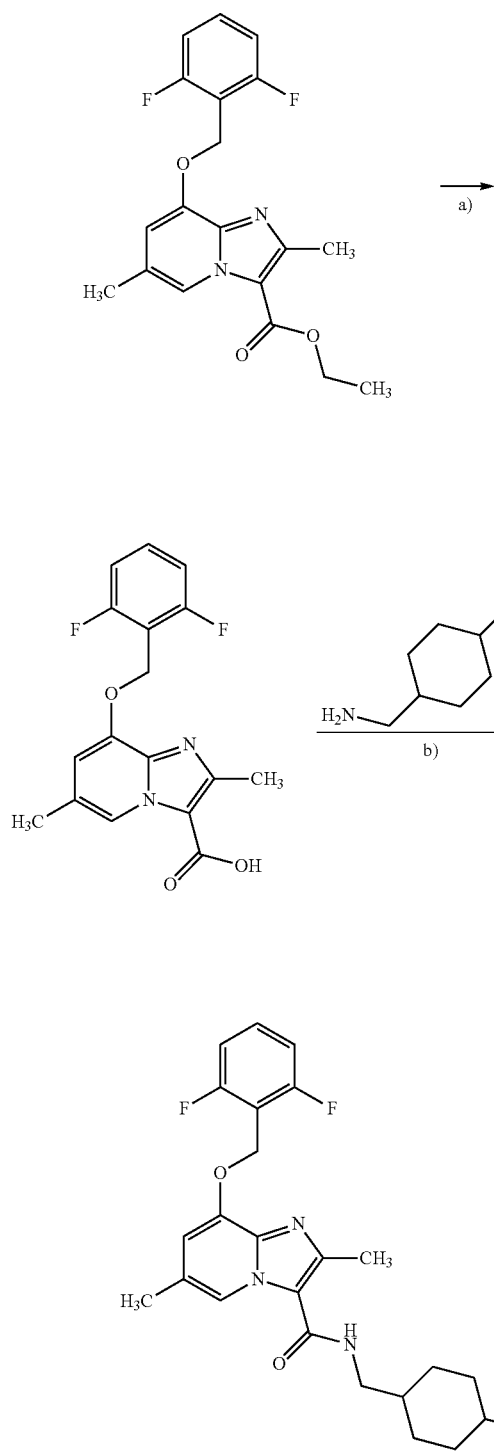

[a]: lithium hydroxide, THF/methanol/H₂O, RT; b): HATU, 4-methylmorpholine or N,N-diisopropylethylamine, DMF].

Scheme 2:

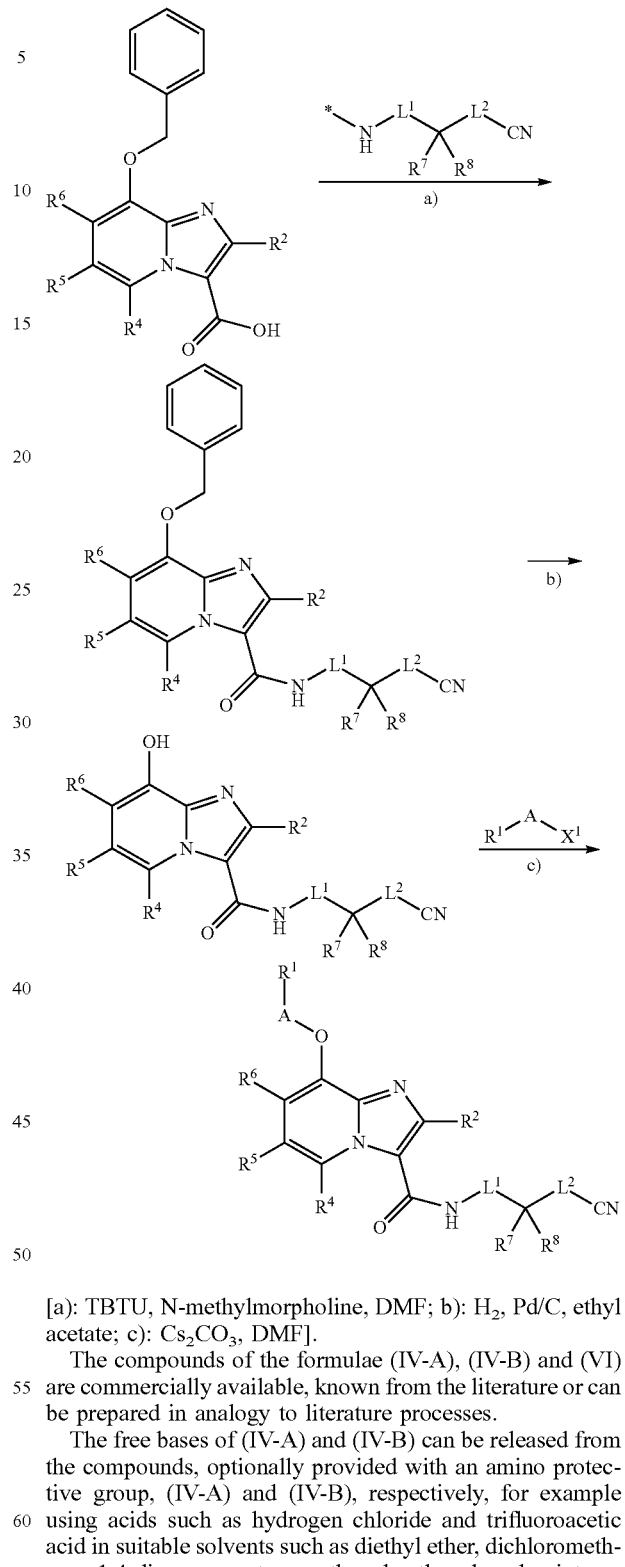

[a): TBTU, N-methylmorpholine, DMF; b): H₂, Pd/C, ethyl acetate; c): Cs₂CO₃, DMF].

The compounds of the formulae (IV-A), (IV-B) and (VI) are commercially available, known from the literature or can be prepared in analogy to literature processes.

The free bases of (IV-A) and (IV-B) can be released from the compounds, optionally provided with an amino protective group, (IV-A) and (IV-B), respectively, for example using acids such as hydrogen chloride and trifluoroacetic acid in suitable solvents such as diethyl ether, dichloromethane, 1,4-dioxane, water, methanol, ethanol and mixtures thereof.

Inert solvents for the process steps (III)+(IV)→(I) and (III-B)+(IV-A)→(I-A) or (III-B)+(IV-B)→(I-B) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

Suitable for use as condensing agents for the amide formation in process steps (III)+(IV)→(I) and (III-B)+(IV-A)→(I-A) or (III-B)+(IV-B)→(I-B) are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline or isobutyl chloroformate, propanephosphonic anhydride (T3P), 1-chloro-N,N,2-trimethylprop-1-en-1-amine, diethyl cyanophosphonate, bis-(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), O-(benzotriazol-1-yl)-N,N,N',N'-tetramethyluronium tetrafluoroborate (TBTU), 0-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate or sodium bicarbonate or potassium bicarbonate, or organic bases such as trialkylamines, for example triethylamine, N-methylmorpholine, N-methylpiperidine or N,N-diisopropylethylamine. Preference is given to using TBTU in combination with N-methylmorpholine, HATU in combination with N,N-diisopropylethylamine or 1-chloro-N,N,2-trimethylprop-1-en-1-amine.

The condensations (III)+(IV)→(I) and (III-B)+(IV-A)→(I-A) or (III-B)+(IV-B)→(I-B) is generally conducted within a temperature range from −20° C. to +100° C., preferably at 0° C. to +60° C. The conversion can be carried out under atmospheric, elevated or reduced pressure (for example from 0.5 to 5 bar). In general, the reaction is carried out at atmospheric pressure.

Alternatively, the carboxylic acid of the formula (III) can also first be converted to the corresponding carbonyl chloride and the latter can then be reacted directly or in a separate reaction with an amine of the formula (IV-A) or (IV-B) to give the compounds of the invention. The formation of carbonyl chlorides from carboxylic acids is effected by the methods known to those skilled in the art, for example by treatment with thionyl chloride, sulphuryl chloride or oxalyl chloride, in the presence of a suitable base, for example in the presence of pyridine, and optionally with addition of dimethylformamide, optionally in a suitable inert solvent.

The hydrolysis of the ester group $T^1$ in the compounds of the formula (II) is effected by customary methods, by treating the esters in inert solvents with acids or bases, in which latter case the salts formed at first are converted to the free carboxylic acids by treating with acid. In the case of the tert-butyl esters, the ester hydrolysis is preferably effected with acids. In the case of the benzyl esters, the ester hydrolysis is preferably effected by hydrogenolysis with palladium on activated carbon or Raney nickel. Suitable inert solvents for this reaction are water or the organic solvents customary for ester hydrolysis. These preferably include alcohols such as methanol, ethanol, n-propanol, isopropanol, n-butanol or tert-butanol, or ethers such as diethyl ether, tetrahydrofuran, 2-methyltetrahydrofuran, dioxane or glycol dimethyl ether, or other solvents such as acetone, dichloromethane, dimethylformamide or dimethyl sulphoxide. It is also possible to use mixtures of the solvents mentioned. In the case of a basic ester hydrolysis, preference is given to using mixtures of water with dioxane, tetrahydrofuran, methanol and/or ethanol.

Suitable bases for the ester hydrolysis are the customary inorganic bases. These preferably include alkali metal or alkaline earth metal hydroxides, for example sodium hydroxide, lithium hydroxide, potassium hydroxide or barium hydroxide, or alkali metal or alkaline earth metal carbonates, such as sodium carbonate, potassium carbonate or calcium carbonate. Particular preference is given to sodium hydroxide or lithium hydroxide.

Suitable acids for the ester hydrolysis are generally sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid, or mixtures thereof, optionally with addition of water. Preference is given to hydrogen chloride or trifluoroacetic acid in the case of the tert-butyl esters and to hydrochloric acid in the case of the methyl esters.

The ester hydrolysis is generally carried out within a temperature range from 0° C. to +100° C., preferably at +0° C. to +50° C.

These conversions can be performed at atmospheric, elevated or reduced pressure (for example from 0.5 to 5 bar). In general, the reaction is in each case carried out at atmospheric pressure.

Inert solvents for the process step (V-A)+(VI)→(I) or (V-B)+(VI)→(I) are, for example, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP) or pyridine. It is also possible to use mixtures of the solvents mentioned. Preference is given to using dimethylformamide or dimethyl sulphoxide.

Suitable bases for the process step (V)+(VI)→(I) or (V-B)+(VI)→(I) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, optionally with addition of an alkali metal iodide, for example sodium iodide or potassium iodide, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 4-(N,N-dimethylamino)pyridine (DMAP), 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using potassium carbonate, caesium carbonate or sodium methoxide.

The reaction is generally effected within a temperature range from 0° C. to +120° C., preferably at +20° C. to +80° C., optionally in a microwave. The reaction can be carried out under atmospheric, elevated or reduced pressure (for example from 0.5 to 5 bar).

The amino protective group used is preferably tert-butoxycarbonyl (Boc) or benzyloxycarbonyl (Z). The protective group used for a hydroxy or carboxyl function is preferably tert-butyl or benzyl. These protective groups are detached by customary methods, preferably by reaction with a strong acid such as hydrogen chloride, hydrogen bromide or trifluoroacetic acid in an inert solvent such as dioxane, diethyl ether, dichloromethane or acetic acid; it is optionally also possible to effect the detachment without an additional inert solvent. In the case of benzyl and benzyloxycarbonyl as protective groups, these may also be removed by hydrogenolysis in the presence of a palladium catalyst. The detachment of the protective groups mentioned can optionally be undertaken simultaneously in a one-pot reaction or in separate reaction steps.

The removal of the benzyl group in the reaction step (I-A)→(V-A) or (I-B)→(V-B) is carried out here by customary methods known from protective group chemistry, preferably by hydrogenolysis in the presence of a palladium catalyst, for example palladium on activated carbon, in an inert solvent, for example ethanol or ethyl acetate [see also, for example, T.W. Greene and P.G.M. Wuts, *Protective Groups in Organic Synthesis*, Wiley, New York, 1999].

The compounds of the formula (II) are known from the literature or can be prepared by reacting a compound of the formula (VII)

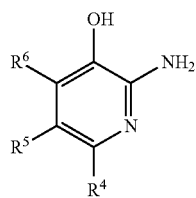

(VII)

in which $R^4$, $R^5$ and $R^6$ have the meaning given above, in an inert solvent in the presence of a suitable base with a compound of the formula (VI) to give a compound of the formula (VIII)

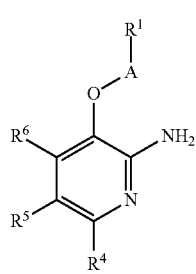

(VIII)

in which $R^1$, $R^4$, $R^5$ and $R^6$ each have the meanings given above, and then reacting the latter in an inert solvent with a compound of the formula (IX)

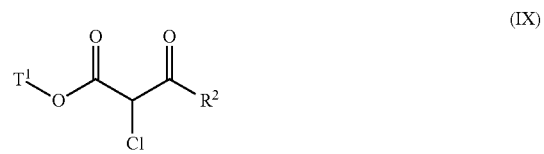

(IX)

in which $R^2$ and $T^1$ are each as defined above.

The process described is illustrated in an exemplary manner by the scheme below (Scheme 3):

Scheme 3:

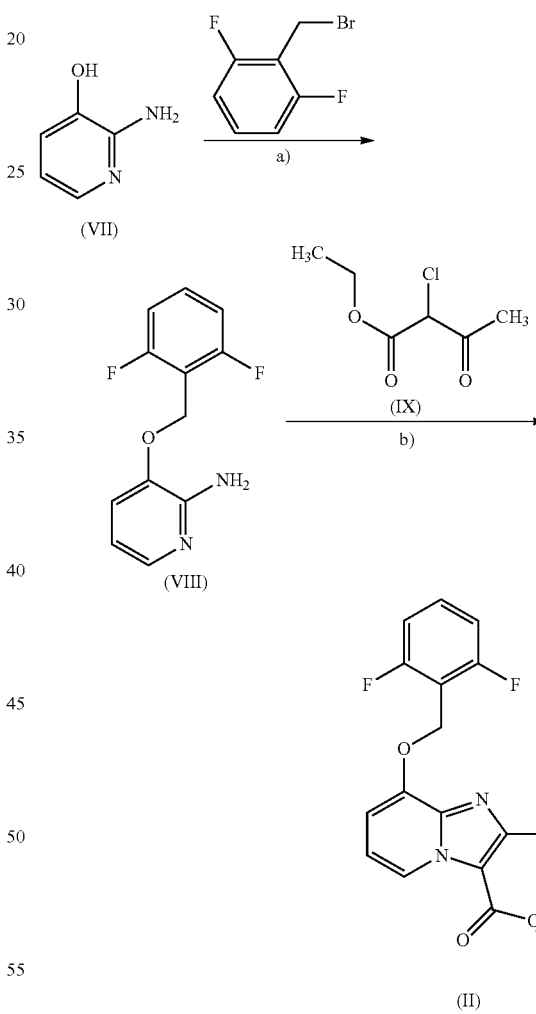

[a]: i) NaOMe, MeOH, RT; ii) DMSO, RT; b): EtOH, molecular sieve, reflux].

The synthesis sequence shown can be modified such that the respective reaction steps are carried out in a different order. An example of such a modified synthesis sequence is shown in Scheme 4.

Scheme 4:

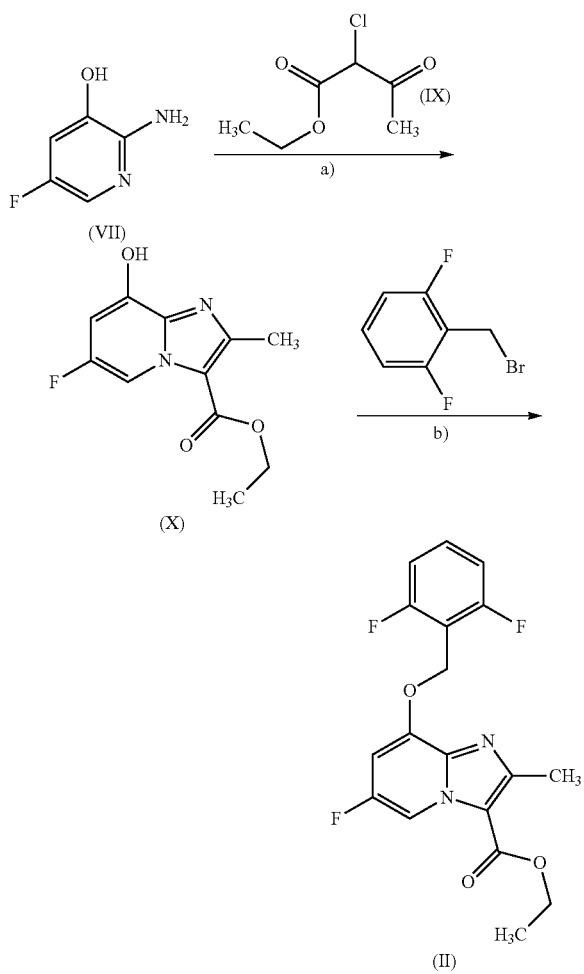

[a): EtOH, molecular sieve, reflux; b): b) Cs$_2$CO$_3$, DMF, 50° C.].

Inert solvents for the ring closure to give the imidazo[1,2-a]pyridine base skeleton (VIII)+(IX)→(II) or (VII)+(IX)→(X) are the customary organic solvents. These preferably include alcohols such as methanol, ethanol, n-propanol, isopropanol, n-butanol, n-pentanol or tert-butanol, or ethers such as diethyl ether, tetrahydrofuran, 2-methyltetrahydrofuran, dioxane or glycol dimethyl ether, or other solvents such as acetone, dichloromethane, 1,2-dichloroethane, acetonitrile, dimethylformamide or dimethyl sulphoxide. It is also possible to use mixtures of the solvents mentioned. Preference is given to using ethanol.

The ring closure is generally effected within a temperature range from +50° C. to +150° C., preferably at +50° C. to +100° C., optionally in a microwave.

The ring closure (VIII)+(IX)→(II) or (VII)+(IX)→(X) is optionally effected in the presence of dehydrating reaction additives, for example in the presence of molecular sieve (pore size 4 Å), or using a water separator. The reaction (VIII)+(IX)→(II) or (VII)+(IX)→(X) is effected using an excess of the reagent of the formula (IX), for example with 1 to 20 equivalents of the reagent (IX), optionally with addition of bases (for example sodium bicarbonate), in which case the addition of this reagent can be effected all at once or in several portions.

As an alternative to the introductions of R$^1$ by reaction of the compounds (V), (VII) or (X) with compounds of the formula (VI), as shown in Schemes 1 to 4, it is likewise possible—as shown in Scheme 5—to react these intermediates with alcohols of the formula (XI) under conditions of the Mitsunobu reaction.

Scheme 5:

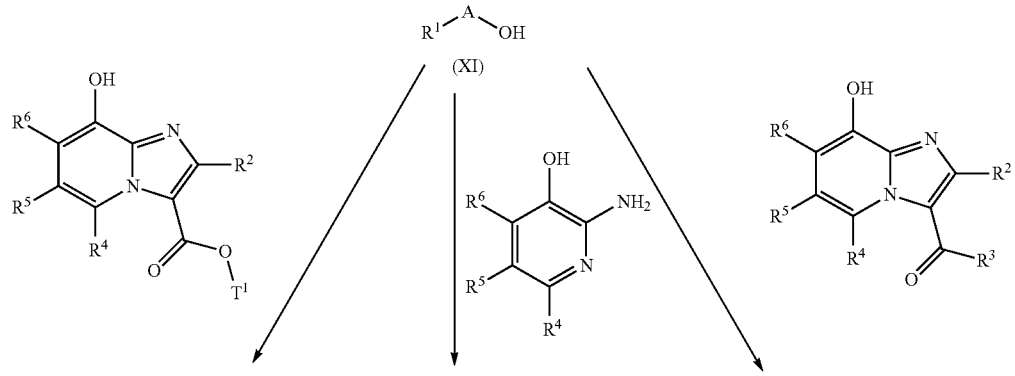

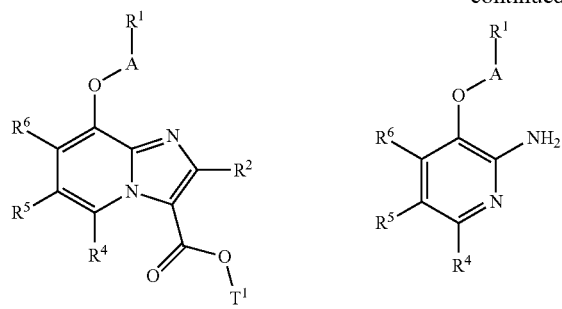

-continued

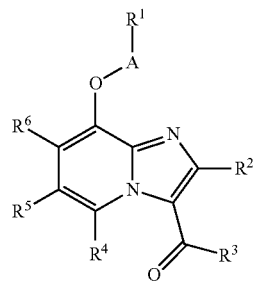

Typical reaction conditions for such Mitsunobu condensations of phenols with alcohols can be found in the relevant literature, e.g. Hughes, D. L. *Org. React.* 1992, 42, 335; Dembinski, R. *Eur. J. Org. Chem.* 2004, 2763. Typically, the reaction is carried out using an activating agent, e.g. diethyl azodicarboxylate (DEAD) or diisopropyl azodicarboxylate (DIAD), and a phosphine reagent, e.g. triphenylphosphine or tributylphosphine, in an inert solvent, e.g. THF, dichloromethane, toluene or DMF, at a temperature between 0° C. and the boiling point of the solvent employed.

Further compounds of the invention can optionally also be prepared by conversions of functional groups of individual substituents, especially those listed for $R^3$, proceeding from the compounds of the formula (I) obtained by above processes. These conversions are performed by customary methods known to those skilled in the art and include, for example, reactions such as nucleophilic and electrophilic substitutions, oxidations, reductions, hydrogenations, transition metal-catalysed coupling reactions, eliminations, alkylation, amination, esterification, ester hydrolysis, etherification, ether hydrolysis, formation of carbonamides, and introduction and removal of temporary protective groups.

The compounds of the invention have valuable pharmacological properties and can be used for the prevention and treatment of diseases in humans and animals. The compounds of the invention offer a further treatment alternative and thus enlarge the field of pharmacy.

The compounds of the invention bring about vasorelaxation and inhibition of platelet aggregation, and lead to a decrease in blood pressure and to a rise in coronary blood flow. These effects are mediated by a direct stimulation of soluble guanylate cyclase and an intracellular rise in cGMP. In addition, the compounds of the invention enhance the action of substances which increase the cGMP level, for example EDRF (endothelium-derived relaxing factor), NO donors, protoporphyrin IX, arachidonic acid or phenylhydrazine derivatives.

The compounds of the invention are suitable for the treatment and/or prophylaxis of cardiovascular, pulmonary, thromboembolic and fibrotic disorders.

Accordingly, the compounds according to the invention can be used in medicaments for the treatment and/or prophylaxis of cardiovascular disorders such as, for example, high blood pressure (hypertension), resistant hypertension, acute and chronic heart failure, coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term "heart failure" encompasses both acute and chronic forms of heart failure, and also more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure and acute phases of worsening of existing chronic heart failure (worsening heart failure).

In addition, the compounds of the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetelipoproteinaemia, sitosterolaemia, xanthomatosis, Tangier disease, adiposity, obesity and of combined hyperlipidaemias and metabolic syndrome.

The compounds of the invention can also be used for the treatment and/or prophylaxis of primary and secondary Raynaud's phenomenon, microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic over-active bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds of the invention are also suitable for the treatment and/or prophylaxis of kidney disorders, in particular of acute and chronic renal insufficiency and acute and chronic renal failure. In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the compounds of the invention for the treatment and/or prophylaxis of sequelae of renal insufficiency, for example pulmonary oedema, heart failure, uraemia, anaemia, electrolyte disorders (for example hyperkalaemia, hyponatraemia) and disorders in bone and carbohydrate metabolism.

In addition, the compounds of the invention are also suitable for the treatment and/or prophylaxis of asthmatic disorders, pulmonary arterial hypertension (PAH) and other forms of pulmonary hypertension (PH) including left-heart disease-, HIV-, sickle cell anaemia-, thromboembolism- (CTEPH), sarcoidosis-, COPD- or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeldt-Jakob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

In addition, the compounds of the invention are also suitable for controlling cerebral blood flow and are effective agents for controlling migraines. They are also suitable for the prophylaxis and control of sequelae of cerebral infarct (Apoplexia cerebri) such as stroke, cerebral ischaemias and skull-brain trauma. The compounds according to the invention can likewise be used for controlling states of pain and tinnitus.

In addition, the compounds of the invention have anti-inflammatory action and can therefore be used as anti-inflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

Furthermore, the compounds of the invention can also be used for the treatment and/or prophylaxis of autoimmune diseases.

The compounds of the invention are also suitable for the treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis).

The compounds of the invention are also suitable for controlling postoperative scarring, for example as a result of glaucoma operations.

The compounds of the invention can also be used cosmetically for ageing and keratinizing skin.

Moreover, the compounds according to the invention are suitable for the treatment and/or prophylaxis of hepatitis, neoplasms, osteoporosis, glaucoma and gastroparesis.

The present invention further provides for the use of the compounds according to the invention for the treatment and/or prophylaxis of disorders, especially the disorders mentioned above.

The present invention further provides for the use of the compounds of the invention for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides the compounds of the invention for use in a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides for the use of the compounds of the invention for production of a medicament for the treatment and/or prophylaxis of disorders, especially the aforementioned disorders.

The present invention further provides for the use of the compounds of the invention for production of a medicament for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides a method for the treatment and/or prophylaxis of disorders, in particular the disorders mentioned above, using an effective amount of at least one of the compounds of the invention.

The present invention further provides a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis using an effective amount of at least one of the compounds of the invention.

The compounds according to the invention can be used alone or, if required, in combination with other active compounds. The present invention further provides medicaments comprising at least one of the compounds of the invention and one or more further active compounds, especially for the treatment and/or prophylaxis of the aforementioned disorders. Preferred examples of active compounds suitable for combinations include:

organic nitrates and NO donors, for example sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil;

antithrombotic agents, by way of example and with preference from the group of the platelet aggregation inhibitors, the anticoagulants or the profibrinolytic substances;

hypotensive active compounds, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or active compounds altering lipid metabolism, for example and with preference from the group of the thyroid receptor agonists, cholesterol synthesis inhibitors such as, by way of example and preferably, HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Antithrombotic agents are preferably understood to mean compounds from the group of the platelet aggregation inhibitors, the anticoagulants or the profibrinolytic substances.

In a preferred embodiment of the invention, the compounds according to the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, dabigatran, melagatran, bivalirudin or clexane.

In a preferred embodiment of the invention, the compounds according to the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan or embursatan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone or eplerenone.

In a preferred embodiment of the invention, the compounds of the invention are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds of the invention are administered in combination with a CETP inhibitor, by way of example and with preference dalcetrapib, BAY 60-5521, anacetrapib or CETP vaccine (CETi-1).

In a preferred embodiment of the invention, the compounds according to the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, by way of example and with preference orlistat.

In a preferred embodiment of the invention, the compounds according to the invention are administered in combination with a polymeric bile acid adsorber, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist, by way of example and with preference gemcabene calcium (CI-1027) or nicotinic acid.

The present invention further provides medicaments which comprise at least one compound according to the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds of the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary in some cases to deviate from the stated amounts, specifically as a function of body weight, route of administration, individual response to the active compound, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are based in each case on volume.

A. EXAMPLES

Abbreviations and Acronyms:
aq. aqueous solution
calc. calculated
br. broad signal (NMR coupling pattern)
CAS No. Chemical Abstracts Service number
Δ shift in the NMR spectrum (stated in)
d doublet (NMR coupling pattern)
TLC thin-layer chromatography
DCI direct chemical ionization (in MS)
DMAP 4-N,N-dimethylaminopyridine
DMF dimethylformamide
DMSO dimethyl sulphoxide
EDCI N-[3-(dimethylamino)propyl]-N'-ethylcarbodiimide
eq. equivalent(s)
ESI electrospray ionization (in MS)
Et ethyl
ent enantiomerically pure
h hour(s)
HATU N-Rdimethylamino)(3H-[1,2,3]triazolo[4,5-N-pyridin-3-yloxy)methylene]-N-methylmethanaminium hexafluorophosphate
HOBT 1H-benzotriazol-1-ol
HPLC high-pressure, high-performance liquid chromatography
HRMS high-resolution mass spectrometry
conc. concentrated
LC-MS liquid chromatography-coupled mass spectrometry
LiHMDS lithium hexamethyldisilazide
m multiplet
Me methyl
min minute(s)
MS mass spectrometry
NMR nuclear magnetic resonance spectrometry
$Pd_2dba_3$ tris(dibenzylideneacetone)dipalladium
Ph phenyl
q quartet (NMR coupling pattern)
quint. quintet (NMR coupling pattern)
rac racemic
$R_F$ retention factor (in thin-layer chromatography)
RT room temperature
$R_t$ retention time (in HPLC)
s singlet (NMR coupling pattern)
t triplet (NMR coupling pattern)
TFA trifluoroacetate
THF tetrahydrofuran
TBTU (benzotriazol-1-yloxy)bisdimethylaminomethylium fluoroborate
UV ultraviolet spectrometry
v/v ratio by volume (of a solution)
Xantphos 4,5-bis(diphenylphosphino)-9,9-dimethylxanthene
XPHOS dicyclohexyl(2',4',6'-triisopropylbiphenyl-2-yl)phosphine LC/MS and HPLC Methods:

Method 1 (LC-MS):
Instrument: Waters ACQUITY SQD UPLC system; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 2 (LC-MS):
Instrument: Micromass Quattro Premier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 3 (LC-MS):
MS instrument type: Waters Micromass Quattro Micro; HPLC instrument type: Agilent 1100 series; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 4 (LC-MS):

MS instrument: Waters SQD; HPLC instrument: Waters UPLC; column: Zorbax SB-Aq (Agilent), 50 mm×2.1 mm, 1.8 µm; mobile phase A: water+0.025% formic acid, mobile phase B: acetonitrile (ULC)+0.025% formic acid; gradient: 0.0 min 98% A–0.9 min 25% A–1.0 min 5% A–1.4 min 5% A–1.41 min 98% A–1.5 min 98% A; oven: 40° C.; flow rate: 0.600 ml/min; UV detection: DAD; 210 nm.

Method 5 (LC-MS):

MS instrument: Waters ZQ 2000; HPLC instrument: Agilent 1100, 2-column system, autosampler: HTC PAL; column: YMC-ODS-AQ, 50 mm×4.6 mm, 3.0 µm; mobile phase A: water+0.1% formic acid, mobile phase B: acetonitrile+0.1% formic acid; gradient: 0.0 min 100% A–0.2 min 95% A–1.8 min 25% A–1.9 min 10% A–2.0 min 5% A–3.2 min 5% A–3.21 min 100% A–3.35 min 100% A; oven: 40° C.; flow rate: 3.0 ml/min; UV detection: 210 nm.

Method 6 (Preparative HPLC):

Column: Macherey-Nagel VP 50/21 Nucleosil 100-5 C18 Nautilus. Flow rate: 25 ml/min. Gradient: A=acetonitrile, B=water+0.1% formic acid, 0.0 min 10% A; 2.00 min 10% A; 6.00 min 90% A; 7.00 min 90% A; 7.10 min 10% A; 8.00 min 10% A; UV detection: 220 nm.

Method 7 (Preparative HPLC):

Column: Phenomenex Gemini C18; 110A, AXIA, 5 µm, 21.2×50 mm 5 micron; gradient: A=water+0.1% conc. ammonia, B=acetonitrile, 0.0 min=10% B, 2.0 min=10% B, 6.0 min=90% B, 7.0 min=90% B, 7.1 min=10% B, 8.0 min=10% B, flow rate 25 ml/min, UV detection 220 nm.

Method 8 (Preparative HPLC):

Column: Axia Gemini 5µ C18 110 A, 50×21.5 mm, P/NO: 00B-4435-P0-AX, S/NO: 35997-2, gradient: A=water+0.1% conc. aq. ammonia, B=acetonitrile, 0.0 min=30% B, 2.0 min=30% B, 6.0 min=100% B, 7.0 min=100% B, 7.1 min=30% B, 8.0 min=30% B, flow rate 25 ml/min, UV detection 220 nm.

Method 9 (Preparative HPLC):

Column: Macherey-Nagel VP 50/21 Nucleosil 100-5 C18 Nautilus. Flow rate: 25 ml/min. Gradient: A=water+0.1% formic acid, B=methanol, 0.0 min=30% B, 2.0 min=30% B, 6.0 min=100% B, 7.0 min=100% B, 7.1 min=30% B, 8.0 min=30% B, flow rate 25 ml/min, UV detection 220 nm.

Method 10 (Preparative HPLC):

Column: Macherey-Nagel VP 50/21 Nucleosil 100-5 C18 Nautilus. Flow rate: 25 ml/min. Gradient: A=water+0.1% conc. aq ammonia, B=methanol, 0.0 min=30% B, 2.0 min=30% B, 6.0 min=100% B, 7.0 min=100% B, 7.1 min=30% B, 8.0 min=30% B, flow rate 25 ml/min, UV detection 220 nm.

Method 11 (Preparative HPLC):

MS instrument: Waters, HPLC instrument: column Waters X-Bridge C18, 18 mm×50 mm, 5 µm, mobile phase A: water+0.05% triethylamine, mobile phase B: acetonitrile (ULC)+0.05% triethylamine, gradient: 0.0 min 95% A–0.15 min 95% A–8.0 min 5% A–9.0 min 5% A; flow rate: 40 ml/min; UV detection: DAD; 210-400 nm.

or:

MS instrument: Waters, HPLC instrument: Waters (column Phenomenex Luna 5µ C18(2) 100A, AXIA Tech. 50×21.2 mm, mobile phase A: water+0.05% formic acid, mobile phase B: acetonitrile (ULC)+0.05% formic acid, gradient: 0.0 min 95% A–0.15 min 95% A–8.0 min 5% A–9.0 min 5% A; flow rate: 40 ml/min; UV detection: DAD; 210-400 nm).

Method 12 (LC-MS):

MS instrument: Waters SQD; HPLC instrument: Waters UPLC; column: Zorbax SB-Aq (Agilent), 50 mm×2.1 mm, 1.8 µm; mobile phase A: water+0.025% formic acid, mobile phase B: acetonitrile (ULC)+0.025% formic acid; gradient: 0.0 min 98% A–0.9 min 25% A–1.0 min 5% A–1.4 min 5% A–1.41 min 98% A–1.5 min 98% A; oven: 40° C.; flow rate: 0.600 ml/min; UV detection: DAD; 210 nm.

Method 13 (DCI-MS):

Instrument: DSQ II; Thermo Fisher-Scientific; DCI with $NH_3$, flow rate: 1.1 ml/min; source temperature: 200° C.; ionization energy 70 eV; heat DCI filament to 800° C.; mass range 80-900.

Method 14 (GC-MS):

Instrument: Micromass GCT, GC6890; column: Restek RTX-35, 15 m×200 µm×0.33 µm; constant helium flow rate: 0.88 ml/min; oven: 70° C.; inlet: 250° C.; gradient: 70° C., 30° C./min→310° C. (maintain for 3 min).

Method 15 (MS):

Instrument: Waters ZQ; ionization type: ESI (+); mobile phase; acetonitrile/water.

Method 16 (LCMS):

Instrument: Waters ACQUITY SQD UPLC system; column: Waters Acquity UPLC HSS T3 1.8µ 30×2 mm; mobile phase A: 1 l of water+0.25 nil of 99% strength formic acid, mobile phase B: 1 l of acetonitrile+0.25 nil of 99% strength formic acid; gradient: 0.0 min 90% A→1.2 min 5% A→2.0 min 5% A oven: 50° C.; flow rate: 0.60 ml/min; UV detection: 208-400 nm.

Method 17 (LC-MS):

Instrument: Micromass Quattro Premier with Waters UPLC Acquity; column: Thermo Hypersil GOLD 1.9µ 50×1 mm; mobile phase A: 1 l of water+0.5 nil of 50% strength formic acid, mobile phase B: 1 l of acetonitrile+0.5 nil of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.

Method 18 (Preparative HPLC):

Chromatorex C18 10µ250×20 mm gradient: A=water+ 0.5% formic acid, B=acetonitrile, 0 min=5% B, 3 min=5% B pre-rinse without substance, then injection, 5 min=5% B, 25 min=30% B, 38 min=30% B, 38.1 min=95% B, 43 min=95% B, 43.01 min=5% B, 48.0 min=5% B flow rate 20 ml/min, wavelength 210 nm.

Method 19 (Preparative HPLC):

Chromatorex C18 10µ 250×20 mm gradient: A=water+ 0.5% formic acid, B=acetonitrile, 0.0 min=5% B, 3.0 min=5% B pre-rinse without substance, then injection, 5.0 min=5% B, 25.0 min=50% B, 38.0 min=50% B, 38.1 min=95% B, 43.0 min=95% B, 43.01 min=5% B, 48.0 min=5% B flow rate 20 ml/min, wavelength 210 nm.

Method 20 (Preparative HPLC):

XBridge Prep. C18 5µ 50×19 mm gradient: A=water+ 0.5% ammonium hydroxide, B=acetonitrile, 0.0 min=5% B, 3.0 min=5% B pre-rinse without substance, then injection, 5.0 min=5% B, 25.0 min=50% B, 38.0 min=50% B, 38.1 min=95% B, 43.00 min=95% B, 43.01 min=5% B, 48.0 min=5% B flow rate 15 ml/min, wavelength 210 nm.

Method 21 (Preparative HPLC):

Chromatorex 10µ 250×20 mm gradient: A=water, B=acetonitrile, 0 min=5% B, 3.0 min=5% B pre-rinse without substance, then injection, 5.0 min=5% B, 25.0 min=95% B, 38.0 min=95% B, 38.1 min=5% B, 40.0 min=5% B, flow rate 20 ml/min, wavelength 210 nm.

Method 22 (LC-MS):

MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 23 (LC-MS):
Instrument: Agilent MS Quad 6150; HPLC: Agilent 1290; column: Waters Acquity UPLC HSS T3 1.8μ 50×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A oven: 50° C.; flow rate: 1.20 ml/min; UV detection: 205-305 nm.

Method 24 (LC-MS):
MS instrument type: Waters Synapt G2S; UPLC instrument type: Waters Acquity I-CLASS; column: Waters, HSST3, 2.1×50 mm, C18 1.8 μm; mobile phase A: 1 l of water+0.01% formic acid; mobile phase B: 1 l of acetonitrile+0.01% formic acid; gradient: 0.0 min 10% B→0.3 min 10% B→1.7 min 95% B→2.5 min 95% B; oven: 50° C.; flow rate: 1.20 ml/min; UV detection: 210 nm.

Method 25 (FIA/MS, ES):
Instrument: Waters ZQ 2000; electrospray ionization; mobile phase A: 1 l of water+0.25 ml of 99% strength formic acid, mobile phase B: 1 l of acetonitrile+0.25 ml of 99% strength formic acid; 25% A, 75% B; flow rate: 0.25 ml/min.

Method 26 (LC/MS): MCW SQ-HSST3 Long
Instrument: Waters ACQUITY SQD UPLC system; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method 27 (LC/MS): MCW-FT-MS-M1
MS instrument type: Thermo Scientific FT-MS; instrument type UHPLC+: Thermo Scientific UltiMate 3000; column: Waters, HSST3, 2.1×75 mm, C18 1.8 μm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/Optimum Integration Path 210-300 nm The multiplicities of proton signals in $^1$H NMR spectra reported in the paragraphs which follow represent the signal form observed in each case and do not take account of any higher-order signal phenomena. In all $^1$H NMR spectra data, the chemical shifts δ are stated in ppm.

Additionally, the starting materials, intermediates and working examples may be present as hydrates. There was no quantitative determination of the water content. In certain cases, the hydrates may affect the $^1$H NMR spectrum and possibly shift and/or significantly broaden the water signal in the $^1$H NMR.

Unless stated otherwise, the percentages in the tests and examples which follow are percentages by weight; parts are parts by weight. Solvent ratios, dilution ratios and concentration data for the liquid/liquid solutions are based in each case on volume.

The multiplicities of proton signals in $^1$H NMR spectra reported in the paragraphs which follow represent the signal form observed in each case and do not take account of any higher-order signal phenomena. In all $^1$H NMR spectra data, the chemical shifts δ are stated in ppm.

When compounds of the invention are purified by preparative HPLC by the above-described methods in which the eluents contain additives, for example trifluoroacetic acid, formic acid or ammonia, the compounds of the invention may be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na+" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Starting Materials and Intermediates:

Example 1A

3-[(2,6-Difluorobenzyl)oxy]pyridine-2-amine

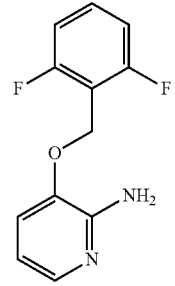 [SMILES: Nc1ncccc1OCc1c(F)cccc1F]

At RT, 51 g of sodium methoxide (953 mmol, 1.05 equivalents) were initially charged in 1000 ml of methanol, 100 g of 2-amino-3-hydroxypyridine (908 mmol, 1 equivalent) were added and the mixture was stirred at RT for another 15 min. The reaction mixture was concentrated under reduced pressure, the residue was taken up in 2500 ml of DMSO and 197 g of 2,6-difluorobenzyl bromide (953 mmol, 1.05 equivalents) were added. After 4 h at RT, the reaction mixture was poured onto 20 l of water, the mixture was stirred for a further 15 min and the solid was filtered off. The solid was washed with 1 l of water and 100 ml of isopropanol and 500 ml of petroleum ether and dried under high vacuum. This gave 171 g of the title compound (78% of theory).

$^1$H-NMR (400 MHz, DMSO-d$_6$): δ=5.10 (s, 2H); 5.52 (br. s, 2H), 6.52 (dd, 1H); 7.16-7.21 (m, 3H); 7.49-7.56 (m, 2H).

Example 2A

Ethyl 8-[(2,6-difluorobenzyl)oxy]-2-methylimidazo[1,2-a]pyridine-3-carboxylate

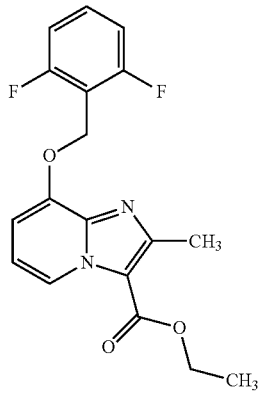 [SMILES: CCOC(=O)c1c(C)nc2c(OCc3c(F)cccc3F)cccn12]

170 g of 3-[(2,6-difluorobenzyl)oxy]pyridine-2-amine (Example 1A; 719 mmol, 1 equivalent) were initially charged in 3800 ml of ethanol, and 151 g of powdered molecular sieve 3 Å and 623 g of ethyl 2-chloroacetoacetate (3.6 mol, 5 equivalents) were added. The reaction mixture was heated at reflux for 24 h and then filtered off through silica gel and concentrated under reduced pressure. The mixture was kept at RT for 48 h and the solid formed was filtered off. The solid was then stirred three times with a little isopropanol and then filtered off, and washed with diethyl ether. This gave 60.8 g (23% of theory) of the title compound. The combined filtrates of the filtration steps were concentrated and the residue was chromatographed on silica gel using the mobile phase cyclohexane/diethyl ether. This gave a further 46.5 g (18% of theory; total yield: 41% of theory) of the title compound.

LC-MS (Method 1): $R_t$=1.01 min

MS (ESpos): m/z=347 (M+H)$^+$ $^1$H-NMR (400 MHz, DMSO-$d_6$): δ=1.36 (t, 3H); 2.54 (s, 3H; obscured by DMSO signal); 4.36 (q, 2H); 5.33 (s, 2H); 7.11 (t, 1H); 7.18-7.27 (m, 3H); 7.59 (quint, 1H); 8.88 (d, 1H).

Example 3A

8-[(2,6-Difluorobenzyl)oxy]-2-methylimidazo[1,2-a]pyridine-3-carboxylic acid

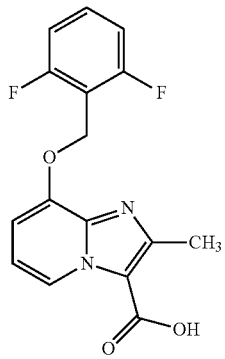 [SMILES: Cc1nc2c(OCc3c(F)cccc3F)cccn2c1C(=O)O]

107 g of ethyl 8-[(2,6-difluorobenzyl)oxy]-2-methylimidazo[1,2-a]pyridine-3-carboxylate (Example 2A; 300 mmol, 1 equivalent) were dissolved in 2.8 l of THF/methanol (1:1), 1.5 l of 1 N aqueous lithium hydroxide solution (1.5 mol, 5 equivalents) were added and the mixture was stirred at RT for 16 h. The organic solvents were removed under reduced pressure and the resulting aqueous solution was, in an ice bath, adjusted to pH 3-4 using 1 N aqueous hydrochloric acid. The resulting solid was filtered off, washed with water and isopropanol and dried under reduced pressure. This gave 92 g (95% of theory) of the title compound.

LC-MS (Method 1): $R_t$=0.62 min

MS (ESpos): m/z=319.1 (M+H)$^+$ $^1$H-NMR (400 MHz, DMSO-$d_6$): δ=2.55 (s, 3H; superposed by DMSO signal); 5.32 (s, 2H); 7.01 (t, 1H); 7.09 (d, 1H); 7.23 (t, 2H); 7.59 (quint, 1H); 9.01 (d, 1H).

Example 4A 3-(Cyclohexylmethoxy)pyridine-2-amine

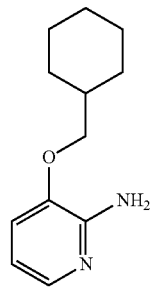 [SMILES: Nc1ncccc1OCC1CCCCC1]

At RT, 96 g of sodium hydroxide, 45% strength in water (1081 mmol, 1 equivalent), were initially charged in 1170 ml of methanol, 119 g of 2-amino-3-hydroxypyridine (1080 mmol, 1 equivalent) were added and the mixture was stirred at RT for another 10 min. The reaction mixture was concentrated under reduced pressure, the residue was taken up in 2900 ml of DMSO and 101 g of cyclohexylmethyl bromide (1135 mmol, 1.05 equivalents) were added. After 16 h at RT, the reaction mixture was slowly added to 6 l of water and the aqueous solution was extracted twice with in each case 2 l of ethyl acetate. The combined organic phases were washed with in each case 1 l of saturated aqueous sodium bicarbonate solution and water, dried, filtered and concentrated. The residue was stirred with 500 ml of n-pentane, filtered and dried under reduced pressure. This gave 130 g (58% of theory) of the title compound.

LC-MS (Method 3): $R_t$=1.41 min

MS (ESpos): m/z=207.1 (M+H)$^+$

Example 5A

Ethyl 8-(cyclohexylmethoxy)-2-methylimidazo[1,2-a]pyridine-3-carboxylate

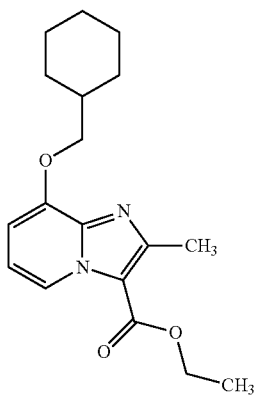 [SMILES: CCOC(=O)c1c(C)nc2c(OCC3CCCCC3)cccn12]

130 g of 3-(cyclohexylmethoxy)pyridine-2-amine (Example 4A; 630 mmol, 1 equivalent) were initially charged in 3950 ml of ethanol, and 436 ml of ethyl 2-chloroacetoacetate (3.2 mol, 5 equivalents) were added. The mixture was heated at reflux for 24 h and then concentrated under reduced pressure. The crude product thus obtained was chromatographed on silica gel using the mobile phase cyclohexane/diethyl ether, giving 66.2 g (33% of theory) of the title compound.

LC-MS (Method 1): $R_t$=1.17 min
MS (ESpos): m/z=317.1 (M+H)$^+$
$^1$H-NMR (400 MHz, DMSO-$d_6$): δ=1.02-1.31 (m, 5H); 1.36 (t, 3H); 1.64-1.77 (m, 3H); 1.79-1.90 (m, 3H); 2.60 (s, 3H); 3.97 (d, 2H); 4.35 (q, 2H); 6.95 (d, 1H); 7.03 (t, 1H); 8.81 (d, 1H).

Example 6A 8-(Cyclohexylmethoxy)-2-methylimidazo[1,2-a]pyridine-3-carboxylic acid

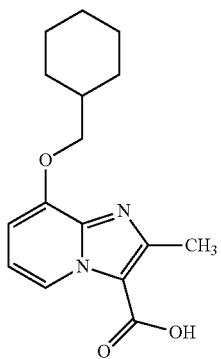 [SMILES: Cc1nc2c(OCC3CCCCC3)cccn2c1C(=O)O]

50 g of ethyl 8-(cyclohexylmethoxy)-2-methylimidazo[1,2-a]pyridine-3-carboxylate (Example 5A; 158 mmol, 1 equivalent) were dissolved in 600 ml of 1,4-dioxane, 790 ml of 2 N aqueous sodium hydroxide solution (1.58 mol, 10 equivalents) were added and the mixture was stirred at RT for 16 h. 316 ml of 6 N hydrochloric acid were added and the mixture was concentrated to about ⅕ of the total volume. The resulting solid was filtered off, washed with water and tert-butyl methyl ether and dried under reduced pressure. This gave 35 g (74% of theory) of the title compound.

LC-MS (Method 1): $R_t$=0.81 min
MS (ESpos): m/z=289.0 (M+H)$^+$
$^1$H-NMR (400 MHz, DMSO-$d_6$): δ=1.03-1.44 (m, 5H); 1.64-1.78 (m, 3H); 1.81-1.92 (m, 3H); 2.69 (s, 3H); 4.07 (d, 2H); 7.30-7.36 (m, 2H); 9.01 (d, 1H).

Example 7A

5-Chloro-2-nitropyridin-3-ol

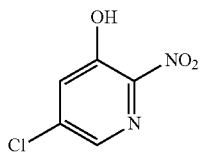 [SMILES: O=[N+]([O-])c1ncc(Cl)cc1O]

With ice cooling, 30 g of 5-chloropyridin-3-ol (232 mmol, 1 equivalent) were dissolved in 228 ml of concentrated sulphuric acid, and 24 ml of concentrated nitric acid were added slowly at 0° C. The reaction was warmed to RT, stirred overnight and then stirred into an ice/water mixture and stirred for another 30 min. The solid was filtered off, washed with cold water and air-dried. This gave 33 g (82% of theory) of the title compound which was used without further purification for the next reaction.

LC-MS (Method 1): $R_t$=0.60 min
MS (ESneg): m/z=172.9/174.9 (M−H)$^−$
$^1$H-NMR (400 MHz, DMSO-$d_6$): δ=7.71 (d, 1H); 8.10 (d, 1H); 12.14 (br. 1H).

Example 8A

5-Chloro-3-[(2,6-difluorobenzyl)oxy]-2-nitropyridine

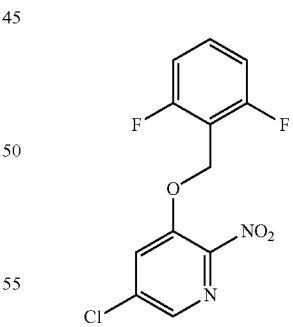

33 g of 5-chloro-2-nitropyridin-3-ol (Example 7A; 189 mmol, 1 equivalent) and 61.6 g of caesium carbonate (189 mmol, 1 equivalent) were initially charged in 528 ml of DMF, 40.4 g of 2,6-difluorobenzyl bromide (189 mmol, 1 equivalent) were added and the mixture was stirred at RT overnight. The reaction mixture was stirred into water/1N aqueous hydrochloric acid. The solid was filtered off, washed with water and air-dried. This gave 54.9 g (97% of theory) of the title compound.

¹H-NMR (400 MHz, DMSO-d₆): δ=5.46 (s, 2H); 7.22 (t, 2H); 7.58 (q, 1H); 8.28 (d, 1H); 8.47 (d, 1H).

Example 9A

5-Chloro-3-[(2,6-difluorobenzyl)oxy]pyridine-2-amine

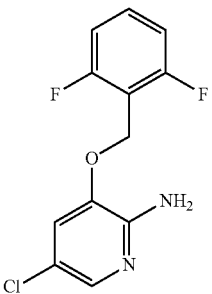 [SMILES: O=[N+]([O-])c1ncc(Cl)cc1OCc1c(F)cccc1F]

59.7 g of 5-chloro-3-[(2,6-difluorobenzyl)oxy]-2-nitropyridine (Example 8A; 199 mmol, 1 equivalent) were initially charged in 600 ml of ethanol, 34.4 g of iron powder (616 mmol, 3.1 equivalents) were added and the mixture was heated to reflux. 152 ml of concentrated hydrochloric acid were slowly added dropwise, and the mixture was boiled at reflux for a further 30 min. The reaction mixture was cooled and stirred into an ice/water mixture. The resulting mixture was adjusted to pH 5 using sodium acetate. The solid was filtered off, washed with water and air-dried and then dried under reduced pressure at 50° C. This gave 52.7 g (98% of theory) of the title compound.

LC-MS (Method 1): R$_t$=0.93 min
MS (ESpos): m/z=271.1/273.1 (M+H)$^+$
¹H-NMR (400 MHz, DMSO-d₆): δ=5.14 (s, 2H); 5.82 (br. s, 2H); 7.20 (t, 2H); 7.35 (d, 1H); 7.55 (q, 1H); 7.56 (d, 1H).

Example 10A

Ethyl 6-chloro-8-[(2,6-difluorobenzyl)oxy]-2-methylimidazo[1,2-a]pyridine-3-carboxylate

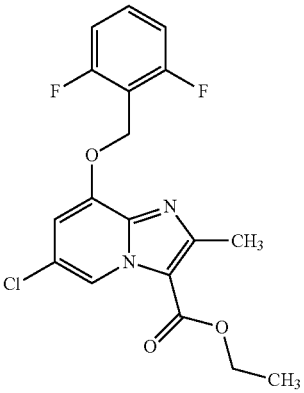

40 g of 5-chloro-3[(2,6-difluorobenzyl)oxy]pyridine-2-amine (Example 9A; 147.8 mmol; 1 equivalent) were initially charged in 800 ml of ethanol, 30 g of powdered molecular sieve 3 Å and 128 g of ethyl 2-chloroacetoacetate (739 mmol, 5 equivalents) were added and the mixture was heated at reflux overnight. The reaction mixture was concentrated, and the residue was taken up in ethyl acetate and filtered. The ethyl acetate phase was washed with water, dried, filtered and concentrated. This gave 44 g (78% of theory) of the title compound.

LC-MS (Method 1): R$_t$=1.27 min
MS (ESpos): m/z=381.2/383.2 (M+H)$^+$
¹H-NMR (400 MHz, DMSO-d₆): δ=1.36 (t, 3H); 2.54 (s, 3H; obscured by DMSO signal); 4.37 (q, 2H); 5.36 (s, 2H); 7.26 (t, 2H); 7.38 (d, 1H); 7.62 (q, 1H); 8.92 (d, 1H).

Example 11A

6-Chloro-8-[(2,6-difluorobenzyl)oxy]-2-methylimidazo[1,2-a]pyridine-3-carboxylic acid

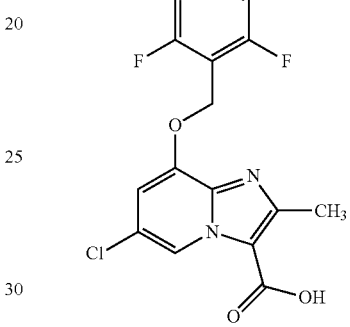

44 g of ethyl 6-chloro-8-[(2,6-difluorobenzyl)oxy]-2-methylimidazo[1,2-a]pyridine-3-carboxylate (Example 10A; 115 mmol, 1 equivalent) were dissolved in 550 ml of THF and 700 ml of methanol, 13.8 g of lithium hydroxide (dissolved in 150 ml of water; 577 mmol, 5 equivalents) were added and the mixture was stirred at RT overnight. 1 N aqueous hydrochloric acid was added and the mixture was concentrated under reduced pressure. The solid obtained was filtered off and washed with water. This gave 34 g of the title compound (84% of theory).

LC-MS (Method 2): R$_t$=1.03 min
MS (ESpos): m/z=353.0/355.0 (M+H)$^+$
¹H-NMR (400 MHz, DMSO-d₆): δ=2.54 (s, 3H; superposed by DMSO signal); 5.36 (s, 2H); 7.26 (t, 2H); 7.34 (d, 1H); 7.61 (q, 1H); 8.99 (d, 1H); 13.36 (br. s, 1H).

Example 12A

5-Bromo-3-[(2,6-difluorobenzyl)oxy]pyridine-2-amine

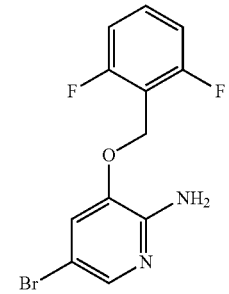 [SMILES: Nc1ncc(Cl)cc1OCc1c(F)cccc1F]

32.6 g of 3-[(2,6-difluorobenzyl)oxy]pyridine-2-amine (Example 1A; 138 mmol, 1 equivalent) were suspended in 552 ml of 10% strength sulphuric acid, and the mixture was cooled to 0° C. 8.5 ml of bromine (165 mmol, 1.2 equivalents) were dissolved in 85 ml of acetic acid and then, over 90 min, added dropwise to the reaction solution, cooled with ice. After the addition had ended, the mixture was stirred at 0° C. for a further 90 min and then diluted with 600 ml of ethyl acetate, and the aqueous phase was separated off. The aqueous phase was extracted with ethyl acetate. The organic phases were combined, washed with saturated aqueous sodium bicarbonate solution, dried and concentrated. The residue was dissolved in dichloromethane and chromatographed on silica gel (petroleum ether/ethyl acetate gradient as mobile phase). This gave 24 g (55% of theory) of the title compound.

LC-MS (Method 1): $R_t$=0.96 min

MS (ESpos): m/z=315.1/317.1 (M+H)$^+$ $^1$H-NMR (400 MHz, DMSO-d$_6$): δ=5.14 (s, 2H); 5.83 (br. s, 2H); 7.20 (t, 2H); 7.42 (d, 1H); 7.54 (q, 1H); 7.62 (d, 1H).

Example 13A

Ethyl 6-bromo-8-[(2,6-difluorobenzyl)oxy]-2-methylimidazo[1,2-a]pyridine-3-carboxylate

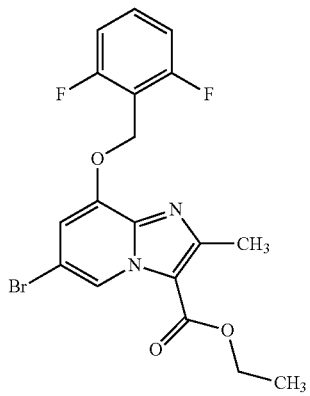 [SMILES: CCOC(=O)c1c(C)nc2c(OCc3c(F)cccc3F)cc(Cl)cn12]

16 g of powdered molecular sieve 3 Å and 52.7 ml of ethyl 2-chloroacetoacetate (380.8 mmol; 5 equivalents) were added to 24 g of 5-bromo-3-[(2,6-difluorobenzyl)oxy]pyridine-2-amine (Example 12A; 76.2 mmol; 1 equivalent) in 400 ml of ethanol, and the mixture was heated at reflux overnight. A further 8 g of molecular sieve were added and the mixture was heated at reflux for a further 24 h. The reaction mixture was concentrated under reduced pressure, and the residue was taken up in dichloromethane and chromatographed on silica gel (mobile phase: dichloromethane/methanol 20:1). The product-containing fractions were concentrated and the residue was stirred with 100 ml of diethyl ether for 30 min. The solid was then filtered off, washed with a little diethyl ether and dried. This gave 15 g (45% of theory) of the title compound.

LC-MS (Method 2): $R_t$=1.43 min

MS (ESpos): m/z=414.9/416.8 (M+H)$^+$ $^1$H-NMR (400 MHz, DMSO-d$_6$): δ=1.36 (t, 3H); 2.54 (s, 3H; obscured by DMSO signal); 4.37 (q, 2H); 5.36 (s, 2H); 7.25 (t, 2H); 7.42 (d, 1H); 7.61 (q, 1H); 9.00 (d, 1H).

Example 14A

6-Bromo-8-[(2,6-difluorobenzyl)oxy]-2-methylimidazo[1,2-a]pyridine-3-carboxylic acid

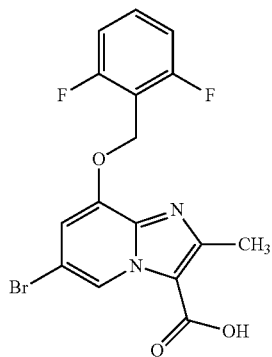 [SMILES: Cc1nc2c(OCc3c(F)cccc3F)cc(Br)cn2c1C(=O)O]

1.5 g of ethyl 6-bromo-8-[(2,6-difluorobenzyl)oxy]-2-methylimidazo[1,2-a]pyridine-3-carboxylate (Example 13A; 3.5 mmol, 1 equivalent) were dissolved in 72 ml of THF/methanol 5:1, 17.6 ml of 1N aqueous lithium hydroxide solution (17.6 mmol, 5 equivalents) were added and the mixture was warmed to 40° C. and stirred at this temperature for 6 h. Using 6 N aqueous hydrochloric acid, the mixture was then adjusted to pH 4 and concentrated under reduced pressure. Water was added to the solid formed, the mixture was stirred and the product was filtered off, washed with water and dried under reduced pressure. This gave 1.24 g of the title compound (88% of theory).

LC-MS (Method 1): $R_t$=0.93 min

MS (ESpos): m/z=397.0/399.1 (M+H)$^+$ $^1$H-NMR (400 MHz, DMSO-d$_6$): δ=2.54 (s, 3H; superposed by DMSO signal); 5.36 (s, 2H); 7.25 (t, 2H); 7.40 (d, 1H); 7.61 (q, 1H); 9.06 (d, 1H); 13.35 (br. s, 1H).

Example 15A

Ethyl 8-[(2,6-difluorobenzyl)oxy]-2,6-dimethylimidazo[1,2-a]pyridine-3-carboxylate

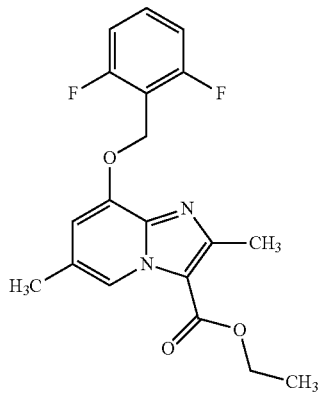 [SMILES: CCOC(=O)c1c(C)nc2c(OCc3c(F)cccc3F)cc(C)cn12]

Method 1:

600 mg of ethyl 6-bromo-8-[(2,6-difluorobenzyl)oxy]-2-methylimidazo[1,2-a]pyridine-3-carboxylate (Example 13A; 1.4 mmol, 1 equivalent) and 230 mg of 1,1'-bis (diphenylphosphino)ferrocenepalladium(II) dichloride/dichloromethane complex (0.282 mmol, 20 mol %) were dissolved in 25 ml of THF, and 0.88 ml (1.76 mmol, 1.2 equivalents) of a 2 M solution of methylzinc chloride in THF was added. In a microwave oven, the reaction mixture was heated at 100° C. for 40 min. The reaction mixture was filtered through Celite and then concentrated under reduced pressure. The residue was chromatographed (Biotage Isolera Four). This gave 225 mg (38% of theory) of the title compound.

Method 2:

20.00 g (85.38 mmol) of ethyl 8-hydroxy-2,6-dimethylimidazo[1,2-a]pyridine-3-carboxylate from Example 20A, 19.44 g (93.91 mmol) of 2,6-difluorobenzyl bromide and 61.20 g (187.83 mmol) of caesium carbonate in 1.18 l of DMF were stirred at 60° C. for 5 h. The reaction mixture was then poured into 6.4 l of 10% strength aqueous sodium chloride solution and then twice extracted with ethyl acetate. The combined organic phases were washed with 854 ml of a 10% strength aqueous sodium chloride solution, dried, concentrated and dried at RT under high vacuum overnight. This gave 28.2 g (92% of theory; purity about 90%) of the title compound.

LC-MS (Method 1): $R_t$=1.05 min
MS (ESpos): m/z=361.1 (M+H)$^+$
$^1$H-NMR (400 MHz, DMSO-d$_6$): δ=1.38 (t, 3H); 2.36 (s, 3H); 4.35 (q, 2H); 5.30 (s, 2H); 7.10 (s, 1H); 7.23 (t, 2H); 7.59 (q, 1H); 8.70 (s, 1H).

Example 16A

8-[(2,6-Difluorobenzyl)oxy]-2,6-dimethylimidazo[1,2-a]pyridine-3-carboxylic acid

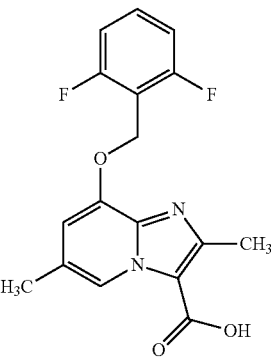

220 mg of ethyl 8-[(2,6-difluorobenzyl)oxy]-2,6-dimethylimidazo[1,2-a]pyridine-3-carboxylate (Example 15A; 0.524 mmol, 1 equivalent) were dissolved in 7 ml of THF/methanol 1:1, 2.6 ml of 1 N aqueous lithium hydroxide solution (2.6 mmol, 5 equivalents) were added and the mixture was stirred at RT for 16 h. The mixture was concentrated under reduced pressure and the residue was acidified with 1N aqueous hydrochloric acid and stirred for 15 min. The solid was filtered off, washed with water and dried under reduced pressure. This gave 120 mg of the title compound (60% of theory).

LC-MS (Method 1): $R_t$=0.68 min
MS (ESpos): m/z=333.1 (M+H)$^+$
$^1$H-NMR (400 MHz, DMSO-d$_6$): δ=2.34 (s, 3H); 5.28 (s, 2H); 7.09 (s, 1H); 7.23 (t, 2H); 7.58 (q, 1H); 8.76 (s, 1H); 13.1 (br. s, 1H).

Example 17A 3-(Benzyloxy)-5-bromopyridine-2-amine

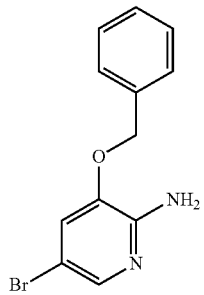 [SMILES: Nc1ncc(Br)cc1OCc1ccccc1]

200 g (1 mol) of 2-amino-3-benzyloxypyridine were initially charged in 4 l of dichloromethane, and at 0° C. a solution of 62 ml (1.2 mol) of bromine in 620 ml of dichloromethane was added over 30 min. After the addition had ended, the reaction solution was stirred at 0° C. for 60 min. About 4 l of saturated aqueous sodium bicarbonate solution were then added to the mixture. The organic phase was removed and concentrated. The residue was purified by silica gel column chromatography (petroleum ether/ethyl acetate 6:4) and the product fractions were concentrated. This gave 214 g (77% of theory) of the title compound.

LC-MS (Method 1): $R_t$=0.92 min
MS (ESpos): m/z=279 (M+H)$^+$
$^1$H-NMR (400 MHz, DMSO-d$_6$): δ=5.16 (s, 2H), 5.94-6.00 (m, 2H), 7.26-7.29 (m, 1H), 7.31-7.36 (m, 1H), 7.37-7.43 (m, 2H), 7.47-7.52 (m, 2H), 7.57-7.59 (m, 1H).

Example 18A

Ethyl 8-(benzyloxy)-6-bromo-2-methylimidazo[1,2-a]pyridine-3-carboxylate

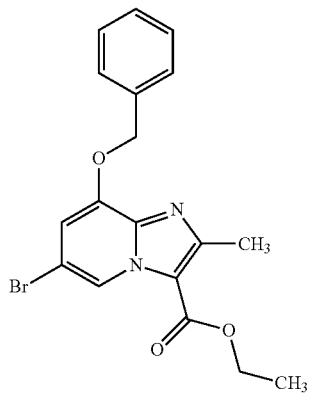

Under argon, 200 g (0.72 mol) of 3-(benzyloxy)-5-bromopyridine-2-amine from Example 17A, 590 g (3.58 mol) of ethyl 2-chloroacetoacetate and 436 g of 3 Å molecular sieve were suspended in 6 l of ethanol, and the suspension was stirred at reflux for 72 h. The reaction mixture was filtered off through silica gel and concentrated. The residue was purified by silica gel chromatography (petroleum ether: ethyl acetate=9:1, then 6:4) and the product fractions were concentrated. This gave 221 g (79% of theory) of the target compound.

LC-MS (Method 16): $R_t$=1.31 min
MS (ESpos): m/z=389 (M+H)$^+$
$^1$H-NMR (400 MHz, DMSO-d$_6$): δ=1.36 (t, 3H), 2.58 (s, 3H), 4.32-4.41 (m, 2H), 5.33 (s, 2H), 7.28-7.32 (m, 1H), 7.36-7.47 (m, 3H), 7.49-7.54 (m, 2H), 8.98 (d, 1H).

Example 19A

Ethyl 8-(benzyloxy)-2,6-dimethylimidazo[1,2-a]pyridine-3-carboxylate

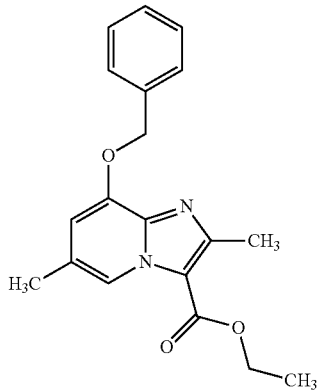 [SMILES: CCOC(=O)c1c(C)nc2c(OCc3ccccc3)cc(C)cn12]

Under argon, 105 g (270 mmol) of ethyl 8-(benzyloxy)-6-bromo-2-methylimidazo[1,2-a]pyridine-3-carboxylate from Example 18A were suspended in 4.2 l of 1,4-dioxane, and 135.4 g (539 mmol, purity 50%) of trimethylboroxine, 31.2 g (27 mmol) of tetrakis(triphenylphosphine)palladium (0) and 78.3 g (566 mmol) of potassium carbonate were added in succession and the mixture was stirred under reflux for 8 h. The precipitate of the reaction mixture, cooled to RT, was removed by filtration over silica gel, and the filtrate was concentrated. The residue was dissolved in dichloromethane and purified by silica gel chromatography (dichloromethane: ethyl acetate=9:1). This gave 74 g (84.6% of theory) of the target compound.
LC-MS (Method 16): $R_t$=1.06 min
MS (ESpos): m/z=325 (M+H)$^+$
$^1$H-NMR (400 MHz, DMSO-d$_6$): δ=1.35 (t, 3H), 2.34 (br. s, 3H), 2.56 (s, 3H), 4.31-4.38 (m, 2H), 5.28 (br. s, 2H), 6.99-7.01 (m, 1H), 7.35-7.47 (m, 3H), 7.49-7.54 (m, 2H), 8.68-8.70 (m, 1H).

Example 20A

Ethyl 8-hydroxy-2,6-dimethylimidazo[1,2-a]pyridine-3-carboxylate

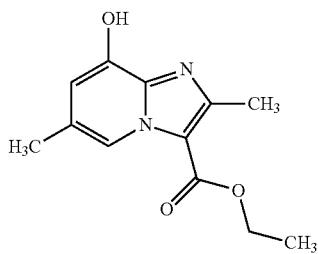 [SMILES: CCOC(=O)c1c(C)nc2c(O)cc(C)cn12]

74 g (228 mmol) of ethyl 8-(benzyloxy)-2,6-dimethylimidazo[1,2-a]pyridine-3-carboxylate from Example 19A were initially charged in 1254 ml of dichloromethane and 251 ml of ethanol, and 20.1 g of 10% palladium on activated carbon (moist with water, 50%) were added under argon. The reaction mixture was hydrogenated at RT and under standard pressure overnight. The reaction mixture was filtered off through silica gel and concentrated. The crude product was purified by silica gel chromatography (dichloromethane: methanol=95:5). This gave 50.4 g (94% of theory) of the target compound.
DCI-MS: (Method 13) (ESpos): m/z=235.2 (M+H)$^+$
$^1$H-NMR (400 MHz, DMSO-d$_6$): δ=1.35 (t, 3H), 2.27 (s, 3H), 2.58 (s, 3H), 4.30-4.38 (m, 2H), 6.65 (d, 1H), 8.59 (s, 1H), 10.57 (br. s, 1H).

Example 21A

Ethyl 2,6-dimethyl-8-[(2,3,6-trifluorobenzyl)oxy]imidazo[1,2-a]pyridine-3-carboxylate

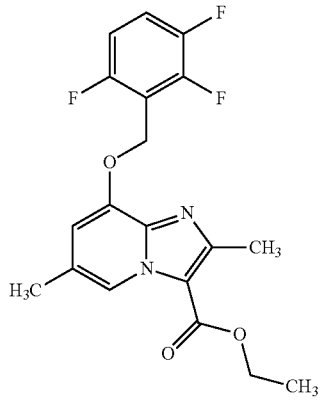 [SMILES: CCOC(=O)c1c(C)nc2c(OCc3c(F)ccc(F)c3F)cc(C)cn12]

3.00 g (12.81 mmol) of ethyl 8-hydroxy-2,6-dimethylimidazo[1,2-a]pyridine-3-carboxylate Example 20A, 3.27 g (14.1 mmol) of 2-(bromomethyl)-1,3,4-trifluorobenzene and 9.18 g (28.17 mmol) of caesium carbonate were initially charged in 183 ml of dry DMF, and the mixture was heated in an oil bath at 60° C. for 30 min. About 1.8 l of water were then added, and the mixture was stirred for 30 min. The solid was filtered off, washed with water and dried under reduced pressure. This gave 5.07 g of the title compound (99% of theory; purity about 96%).
LC-MS (Method 1): $R_t$=1.14 min
MS (ESpos): m/z=379 (M+H)$^+$
$^1$H-NMR (400 MHz, DMSO-d$_6$): δ=1.35 (t, 3H), 2.36 (s, 3H), 2.55 (s, 3H; superposed by DMSO signal), 4.36 (q, 2H), 5.35 (s, 2H), 7.09 (s, 1H), 7.22-7.32 (m, 1H), 7.60-7.73 (m, 1H), 8.72 (s, 1H).

Example 22A 2,6-Dimethyl-8-[(2,3,6-trifluorobenzyl)oxy]imidazo[1,2-a]pyridine-3-carboxylic acid

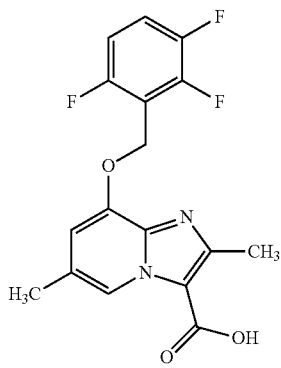

5.07 g (12.87 mmol) of ethyl 2,6-dimethyl-8-[(2,3,6-trifluorobenzyl)oxy]imidazo[1,2-a]pyridine-3-carboxylate Example 21A were dissolved in 275 ml of THF/methanol (5/1), 64.4 ml of 1 N aqueous lithium hydroxide solution were added and the mixture was stirred at 40° C. for 3.5 h. At 0° C., the reaction was acidified to a pH of about 4 using 6 N aqueous hydrochloric acid and concentrated. The solid formed was filtered off, washed with water and dried under reduced pressure. This gave 4.77 g (98% of theory; purity about 93%) of the title compound.

LC-MS (Method 1): $R_t$=0.72 min
MS (ESpos): m/z=351 (M+H)$^+$
$^1$H-NMR (400 MHz, DMSO-d$_6$): δ=2.37 (s, 3H), 2.54 (s, 3H; superposed by DMSO signal), 5.36 (s, 2H), 7.11 (s, 1H), 7.25-7.33 (m, 1H), 7.61-7.73 (m, 1H), 8.78 (s, 1H), 13.10 (br. s, 1H).

Example 23A

Ethyl 8-(benzyloxy)-2-methylimidazo[1,2-a]pyridine-3-carboxylate

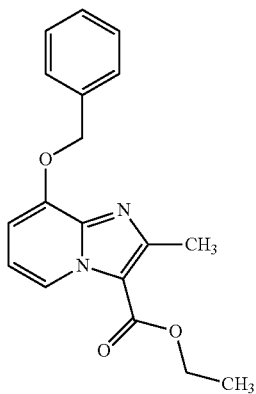 [SMILES: CCOC(=O)c1c(C)nc2c(OCc3ccccc3)cccn12]

25 g (124.8 mmol) of 2-amino-3-benzyloxypyridine were dissolved in 781 ml of ethanol, 102.7 g (624.2 mmol) of ethyl 2-chloroacetoacetate and two tablespoons of 4 A molecular sieve were added and the reaction mixture was then heated at reflux (bath temperature 100° C.) for 2 days. The mixture was concentrated and excess ethyl 2-chloroacetoacetate was distilled off on a rotary evaporator using dry ice cooling. The residue was purified by silica gel chromatography (mobile phase: cyclohexane:ethyl acetate—gradient 9:1, 4:1). This gave 20.81 g of the target compound (54% of theory).

LC-MS (Method 2): $R_t$=1.12 min
MS (ESpos): m/z=311 (M+H)$^+$
$^1$H-NMR (400 MHz, DMSO-d$_6$): δ=1.35 (t, 3H), 2.59 (s, 3H), 4.34 (q, 2H), 5.32 (s, 2H), 7.01-7.09 (m, 2H), 7.33-7.48 (m, 3H), 7.52 (d, 2H), 8.81-8.86 (m, 1H).

Example 24A

Ethyl 8-hydroxy-2-methylimidazo[1,2-a]pyridine-3-carboxylate

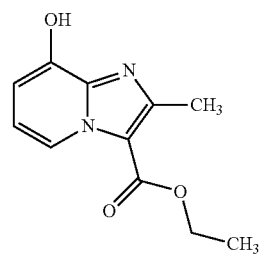 [SMILES: CCOC(=O)c1c(C)nc2c(O)cccn12]

31.45 g (101.3 mmol) of ethyl 8-(benzyloxy)-2-methylimidazo[1,2-a]pyridine-3-carboxylate from Example 23A were dissolved in 2 l of ethyl acetate, 3.15 g of 10% Pd/carbon were added and the mixture was stirred at RT and standard hydrogen pressure for 5 h. The mixture was filtered through kieselguhr, the filter cake was washed well with ethyl acetate/methanol and the filtrate was concentrated to dryness. This gave 21.94 g of the target compound (98% of theory, purity 99%).

LC-MS (Method 1): $R_t$=0.61 min
MS (ESpos): m/z=221 (M+H)$^+$
$^1$H-NMR (400 MHz, DMSO-d$_6$): δ=1.36 (t, 3H), 2.60 (s, 3H), 4.36 (q, 2H), 6.78 (d, 1H), 6.98 (t, 1H), 8.73 (d, 1H), 10.60 (br s, 1H).

Example 25A 3,5-Difluoroisonicotinaldehyde

Under argon and at −70° C., 44 ml of 2.5 M n-butyllithium solution in n-hexane (110 mmol, 1.1 equivalents) were slowly added dropwise to 15.4 ml of diisopropylamine (110 mmol, 1.1 equivalents) in 23 ml of THF. The resulting solution was warmed to 0° C. and stirred at this temperature for 30 min. The reaction mixture was then cooled to −70° C. and diluted with 23 ml of THF, and 11.5 g of 3,5-difluoropyridine (100 mmol, 1 equivalent), dissolved in 72 ml THF, were then added dropwise. The mixture was stirred at −70° C. for a further 30 min. 12.4 ml of methyl formate (200 mmol, 2 equivalents), dissolved in 23 ml of THF, were then quickly added dropwise. After 1.5 h at −70° C., the reaction solution was quickly poured into 230 ml of saturated aqueous sodium bicarbonate solution and extracted with a total of 460 ml of ethyl acetate. The combined organic phases were washed twice with in each case 115 ml of saturated aqueous sodium bicarbonate solution and twice with saturated aqueous sodium chloride solution, dried over sodium sulphate and concentrated. This gave 11.6 g (81% of theory) of the title compound, which were directly reacted further.

GC-MS (Method 14): $R_t$=1.82 min
MS (ESpos): m/z=144.0 (M+H)$^+$
$^1$H-NMR (400 MHz, DMSO-$d_6$): δ=8.75 (br. s, 2H), 10.24 (br. s, 1H).

Example 26A (3,5-Difluoropyridin-4-yl)methanol

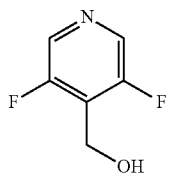

At RT, 11.60 g of 3,5-difluoroisonicotinaldehyde (Example 25A, 81 mmol, 1 equivalent), dissolved in 100 ml of methanol, were added to 3.68 g of sodium borohydride (97.3 mmol, 1.2 equivalents) in 200 ml of methanol. After the evolution of gas had ended (about 2 h), 200 ml of saturated aqueous sodium chloride solution were added and the mixture was extracted twice with in each case 200 ml of ethyl acetate. The combined organic phases were dried over sodium sulphate and concentrated. This gave 9.5 g (81% of theory) of the title compound.

LC-MS (Method 2): $R_t$=0.28 min
MS (ESpos): m/z=146 (M+H)$^+$
$^1$H-NMR (400 MHz, DMSO-$d_6$): δ=4.56 (d, 2H), 5.56 (t, 1H), 8.51 (s, 2H).

Example 27A 4-(Chloromethyl)-3,5-difluoropyridine

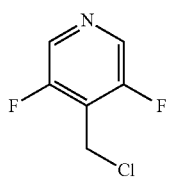

Under argon, 5.0 g of (3,5-difluoropyridin-4-yl)methanol (Example 26A, 34.5 mmol, 1 equivalent) were initially charged in 100 ml of dichloromethane at −20° C., and 5.7 ml of diisopropylethylamine (34.5 mmol, 1 equivalent) and 2.95 ml of methanesulphonyl chloride (37.9 mmol, 1.1 equivalents) were added in succession. The mixture was warmed to RT and stirred at RT for 16 h and then at 40° C. for 3 h. The reaction solution was then concentrated, and twice 50 ml of toluene were added and the solution was concentrated again. This gave 13 g (230% of theory) as a crude product which were reacted further without purification.

Example 28A

Ethyl 8-[(3,5-difluoropyridin-4-yl)methoxy]-2,6-dimethylimidazo[1,2-a]pyridine-3-carboxylate

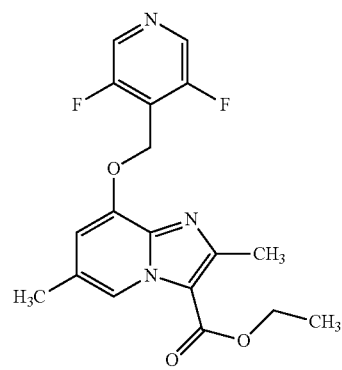 [SMILES: CCOC(=O)c1c(C)nc2c(OCc3c(F)cncc3F)cc(C)cn12]

5.0 g (21.34 mmol) of ethyl 8-hydroxy-2,6-dimethylimidazo[1,2-a]pyridine-3-carboxylate from Example 20A and 3.83 g (23.48 mmol) of 4-(chloromethyl)-3,5-difluoropyridine from Example 27A were initially charged in 306 ml of abs. DMF, and 20.8 g (64.03 mmol) of caesium carbonate were added. The reaction mixture was stirred at 60° C. overnight. The reaction mixture, cooled to RT, was filtered, the filter cake was washed with ethyl acetate and the filtrate was concentrated. The residue was purified by silica gel chromatography (cyclohexane/ethyl acetate gradient=4:1 to 2:1). This gave 5.40 g (70% of theory) of the target compound.

LC-MS (Method 16): $R_t$=0.96 min
MS (ESIpos): m/z=362 (M+H)$^+$
$^1$H-NMR (400 MHz, DMSO-$d_6$): δ=1.35 (t, 3H), 2.36 (s, 3H), 2.51 (s, 3H; superposed by solvent signal), 4.35 (q, 2H), 5.40-5.46 (m, 2H), 7.09 (s, 1H), 8.68 (s, 2H), 8.73 (s, 1H).

Example 29A

8-[(3,5-Difluoropyridin-4-yl)methoxy]-2,6-dimethylimidazo[1,2-a]pyridine-3-carboxylic acid

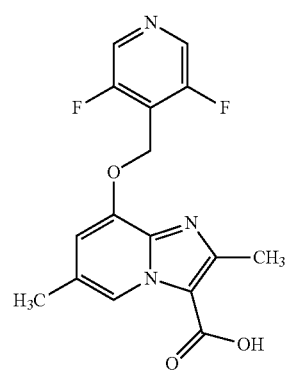

5.34 g (14.78 mmol) of ethyl 8-[(3,5-difluoropyridin-4-yl)methoxy]-2,6-dimethylimidazo[1,2-a]pyridine-3-carboxylate from Example 28A were initially charged in 160 ml of dioxane, 147.8 ml (147.8 mmol) of 1 M aqueous sodium hydroxide solution were added and the mixture was stirred at RT overnight. Using 1 N aqueous hydrochloric acid, the reaction mixture, which had been cooled to RT, was adjusted to about pH 4, the solvent was concentrated to half its original volume and the solid formed was filtered off with suction and dried under reduced pressure. This gave 4.61 g (93% of theory) of the target compound.

LC-MS (Method 1): $R_t$=0.58 min

MS (ESIpos): m/z=334 (M+H)$^+$ $^1$H-NMR (400 MHz, DMSO-d$_6$): δ=2.36 (s, 3H), 2.51 (s, 3H; superposed by solvent signal), 5.41-5.46 (m, 2H), 7.08 (s, 1H), 8.68 (s, 2H), 8.79 (s, 1H), 13.09 (br. s, 1H).

Example 30A

Ethyl 2-chloro-3-oxopropanoate

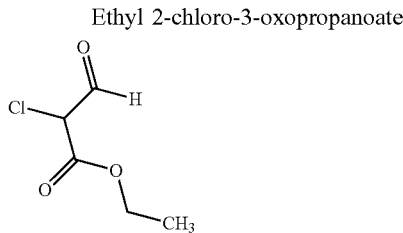

139 ml of a 21% strength sodium ethoxide solution in ethanol (371 mmol, 0.91 equivalent) were initially charged in 200 ml of diethyl ether, and a solution of 43.7 ml of ethyl chloroacetate (408 mmol, 1 equivalent) and 32.9 ml of ethyl formate (408 mmol, 1 equivalent) in 150 ml of diethyl ether was added dropwise at RT. The reaction mixture was stirred overnight and the solid formed was filtered off and washed with diethyl ether. The solid was dissolved in water and the aqueous phase was, with ice-bath cooling, adjusted to pH 4 using concentrated hydrochloric acid. The mixture was repeatedly extracted with diethyl ether and the combined organic phases were washed with saturated aqueous sodium chloride solution, dried with magnesium sulphate, filtered and concentrated. The crude product obtained (8.2 g) was freed from residual solvent under high vacuum and used for the subsequent reaction without further purification.

Example 31A

Ethyl 8-[(2,6-difluorobenzyl)oxy]imidazo[1,2-a]pyridine-3-carboxylate

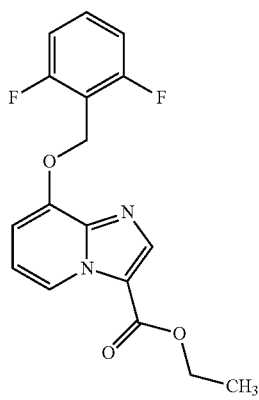 [SMILES: CCOC(=O)c1cnc2c(OCc3c(F)cccc3F)cccn12]

1.93 g of 3[(2,6-difluorobenzyl)oxy]pyridine-2-amine (Example 1A; 8.2 mmol, 1 equivalent) were initially charged in 50 ml of ethanol, and 8.2 g of ethyl 2-chloro-3-oxopropanoate (purity 75%, crude product from Example 30A, 40.8 mmol, 5 equivalents) were added. The reaction mixture was heated at reflux overnight. The mixture was then concentrated under reduced pressure and the crude product obtained was chromatographed on 340 g of silica gel (Biotage Isolera) (mobile phase: cyclohexane:ethyl acetate gradient; $R_f$ of the product in cyclohexane:ethyl acetate 2:1=0.36). The product fractions were combined and concentrated, and the residue obtained was stirred with diisopropyl ether. The solid was filtered off and dried under high vacuum. This gave 2.02 g of the title compound (71% of theory).

LC-MS (Method 1): $R_t$=1.08 min

MS (ESpos): m/z=333.1 (M+H)$^+$ $^1$H-NMR (400 MHz, DMSO-d$_6$): δ=1.35 (t, 3H), 4.39 (q, 2H), 5.35 (s, 2H), 7.15-7.28 (m, 4H), 7.58 (q, 1H), 8.18 (s, 1H), 8.90 (d, 1H).

Example 32A

8-[(2,6-Difluorobenzyl)oxy]imidazo[1,2-a]pyridine-3-carboxylic acid

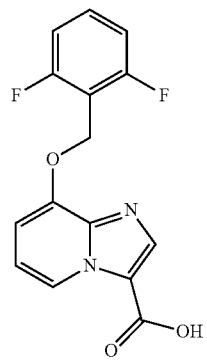 [SMILES: O=C(O)c1cnc2c(OCc3c(F)cccc3F)cccn12]

1 g of ethyl 8-[(2,6-difluorobenzyl)oxy]imidazo[1,2-a]pyridine-3-carboxylate (Example 31A, 3 mmol, 1 equivalent) was initially charged in 60 ml of methanol/THF (5:1), 15 ml of a 1 N aqueous lithium hydroxide solution (15 mmol, 5 equivalents) were added and the mixture was warmed to 40° C. and stirred at this temperature for 4 h. The mixture was then cooled and, with ice cooling, adjusted to pH 4 using 6 N aqueous hydrochloric acid. The organic solvents were removed on a rotary evaporator, water was added to the precipitated product, the mixture was filtered and the product was washed with water and dried under high vacuum. This gave 797 mg (87% of theory) of the title compound.

LC-MS (Method 1): $R_t$=0.66 min

MS (ESpos): m/z=305.1 (M+H)$^+$

1H-NMR (400 MHz, DMSO-d$_6$): δ=5.38 (s, 2H), 7.10-7.28 (m, 4H), 7.59 (q, 1H), 8.12 (s, 1H), 8.92 (s, 1H), 13.1 (br. s, 1H).

Example 33A

Ethyl 2,6-dimethyl-8-(3-methylbutoxy)imidazo[1,2-a]pyridine-3-carboxylate

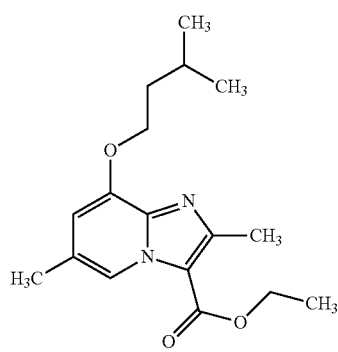 [SMILES: CCOC(=O)c1c(C)nc2c(OCCC(C)C)cc(C)cn12]

1.23 ml (9.4 mmol) of 1-iodo-3-methylbutane and 6.12 g (18.8 mmol) of caesium carbonate were added to 2.0 g (8.5 mmol) of ethyl 8-hydroxy-2,6-dimethylimidazo[1,2-a]pyridine-3-carboxylate Example 20A in 122.3 ml of DMF, and the mixture was stirred at 60° C. for 40 min. The reaction mixture was cooled to RT, 900 ml of water were added, the mixture was stirred at RT for 1 h and the resulting solid was filtered off, washed with water and dried under high vacuum. This gave 2.25 g (84% of theory; purity 97%) of the title compound.

LC-MS (Method 16): $R_t$=1.12 min

MS (ESpos): m/z=305 (M+H)$^+$ $^1$H-NMR (400 MHz, DMSO-d$_6$): δ=0.96 (d, 6H), 1.35 (t, 3H), 1.70 (q, 2H), 1.77-1.89 (m, 1H), 2.33 (s, 3H), 2.56 (s, 3H), 4.17 (t, 2H), 4.34 (q, 2H), 6.88 (s, 1H), 8.64 (s, 1H).

Example 34A 2,6-Dimethyl-8-(3-methylbutoxy)imidazo[1,2-a]pyridine-3-carboxylic acid

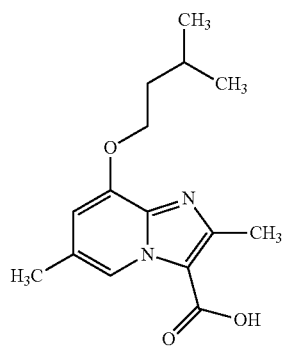

2.25 g (7.4 mmol) of ethyl 2,6-dimethyl-8-(3-methylbutoxy)imidazo[1,2-a]pyridine-3-carboxylate Example 33A were initially charged in 157 ml of THF/methanol (5:1), 37 ml (37 mmol) of 1 N lithium hydroxide solution were added and the reaction mixture was stirred at RT over the weekend. The mixture was then cooled to 0° C., acidified to pH 4 with 6 N hydrochloric acid and freed of the organic solvent under reduced pressure. The solid formed was filtered off, washed with water and dried under high vacuum. This gave 1.64 g (80% of theory; purity 100%) of the title compound.

LC-MS (Method 1): $R_t$=0.71 min

MS (ESpos): m/z=277 (M+H)$^+$ $^1$H-NMR (400 MHz, DMSO-d$_6$): δ=0.96 (d, 6H), 1.70 (q, 2H), 1.78-1.89 (m, 1H), 2.32 (s, 3H), 2.56 (s, 3H), 4.17 (t, 2H), 6.85 (s, 1H), 8.69 (s, 1H), 12.86-13.08 (m, 1H).

Example 35A rac-Ethyl 8-[1-(2,6-difluorophenyl)ethoxy]-2,6-dimethylimidazo[1,2-a]pyridine-3-carboxylate

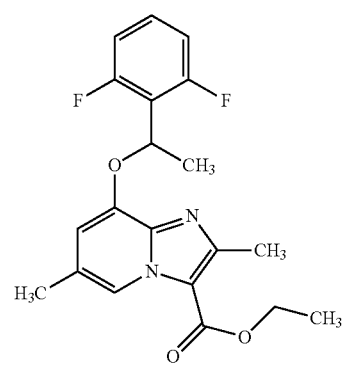 [SMILES: CCOC(=O)c1c(C)nc2c(OC(C)c3c(F)cccc3F)cc(C)cn12]

5.50 g (23.5 mmol) of ethyl 8-hydroxy-2,6-dimethylimidazo[1,2-a]pyridine-3-carboxylate Example 20A together with 4.46 g (28.2 mmol) of 1-(2,6-difluorophenyl)ethanol, 5.35 ml (27.0 mmol) of diisopropyl azodicarboxylate and 7.08 g (27.0 mmol) of triphenylphosphine were dissolved in 141 ml of THF, and the mixture was stirred at RT for 2 h. 0.70 ml (3.5 mmol) of diisopropyl azodicarboxylate and 0.62 g (2.3 mmol) of triphenylphosphine were added to the reaction mixture, and the reaction solution was stirred at RT for 1 h. The solid formed was filtered off and dried under high vacuum. This gave 4.6 g (52.8% of theory; purity 100%) of the title compound. The filtrate was concentrated and purified twice by silica gel chromatography (cyclohexane; ethyl acetate gradient=8:1 to 4:1). All product-containing fractions were purified again by preparative HPLC (RP18 column; mobile phase: acetonitrile/water gradient with addition of 0.1% TFA). This gave another 2.16 g (25% of theory) of the target compound.

LC-MS (Method 1): $R_t$=1.08 min

MS (ESpos): m/z=375 (M+H)$^+$ $^1$H-NMR (400 MHz, DMSO-d$_6$): δ=1.34 (t, 3H), 1.79 (d, 3H), 2.25 (s, 3H), 2.58 (s, 3H), 4.33 (q, 2H), 6.17 (q, 1H), 6.73 (s, 1H), 7.06-7.16 (m, 2H), 7.37-7.48 (m, 1H), 8.67 (s, 1H).

Example 36A ent-Ethyl 8-[1-(2,6-difluorophenyl)ethoxy]-2,6-dimethylimidazo[1,2-a]pyridine-3-carboxylate (Enantiomer B)

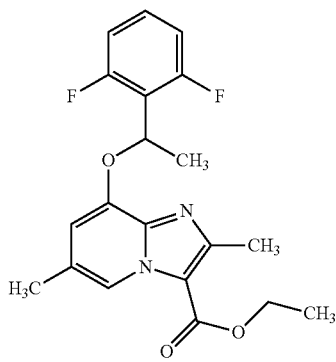 [SMILES: CCOC(=O)c1c(C)nc2c(OC(C)c3c(F)cccc3F)cc(C)cn12]

6.8 g of Example 35A were separated into the enantiomers by preparative separation on a chiral phase [column: Daicel Chiralpak AD-H, 5 µm, 250×30 mm, mobile phase: 70% isohexane, 30% ethanol, flow rate: 50 ml/min; 40° C., detection: 210 nm].

Enantiomer B:
Yield: 2.7 g (98.4% ee)
$R_t$=5.18 min [Daicel Chiralpak AD-H, 5 µm, 250×4.6 mm; mobile phase: 70% isohexane, 30% ethanol; flow rate 1.0 ml/min; 30° C.; detection: 220 nm].

Example 37A ent-8-[1-(2,6-Difluorophenyl)ethoxy]-2,6-dimethyl-imidazo[1,2-a]pyridine-3-carboxylic acid (Enantiomer B)

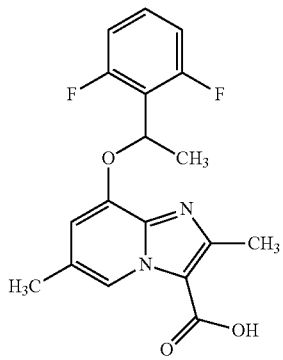

2.58 g (6.9 mmol) of ent-ethyl 8-[1-(2,6-difluorophenyl)ethoxy]-2,6-dimethylimidazo[1,2-a]pyridine-3-carboxylate Example 36A (Enantiomer B) were dissolved in 154 ml of THF/methanol (5:1), 34.5 ml (34.5 mmol) of 1 N aqueous lithium hydroxide solution were added and the mixture was stirred at 40° C. for 5 h. The reaction mixture was cooled to RT and acidified with 6 N hydrochloric acid solution and concentrated. The solid was filtered off, washed with water and dried under high vacuum. This gave 2.26 g (95% of theory; purity 100%) of the title compound.

LC-MS (Method 1): $R_t$=0.74 min
MS (ESpos): m/z=347 (M+H)$^+$
$^1$H-NMR (400 MHz, DMSO-d$_6$): δ=1.79 (d, 3H), 2.24 (s, 3H), 2.57 (s, 3H), 6.16 (q, 1H), 6.67 (s, 1H), 7.06-7.16 (m, 2H), 7.38-7.48 (m, 1H), 8.74 (s, 1H), 12.24-13.90 (br. s, 1H).

Example 38A

Ethyl 2,6-dimethyl-8-[4,4,4-trifluoro-3-(trifluoromethyl)butoxy]imidazo[1,2-a]pyridine-3-carboxylate

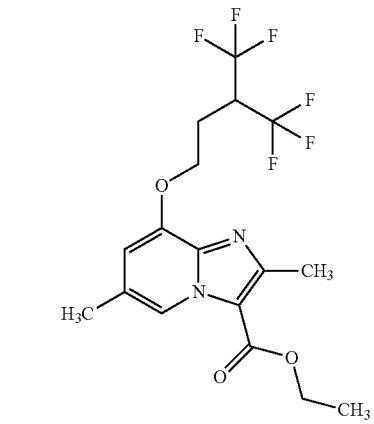 [SMILES: CCOC(=O)c1c(C)nc2c(OCCC(C(F)(F)F)C(F)(F)F)cc(C)cn12]

7.89 g (24.2 mmol) of caesium carbonate and 2.30 g (8.88 mmol) of 4,4,4-trifluoro-3-(trifluoromethyl)butyl bromide were added to 1.89 g (8.07 mmol) of ethyl 8-hydroxy-2,6-dimethylimidazo[1,2-a]pyridine-3-carboxylate Example 20A in 60 ml of DMF, and the reaction mixture was stirred at RT for 90 min. 60 ml of water were then added, the solid formed was filtered off and the filter residue was washed with 100 ml of water and twice with 20 ml of tert-butyl methyl ether. The precipitate formed from the filtrate was filtered off and washed with filtrate. Both filter residues were taken up in 50 ml of ethyl acetate. The solution was concentrated under reduced pressure and the residue was dried under high vacuum overnight. 2.25 g of the target compound (95% purity, 64% of theory) were obtained.

LC-MS (Method 1): $R_t$=1.16 min
MS (ESpos): m/z=413 (M+H)$^+$
$^1$H-NMR (400 MHz, DMSO-d$_6$): δ=1.36 (t, 3H), 2.34 (s, 3H), 2.32-2.38 (m, 2H), 2.58 (s, 3H), 4.18-4.30 (m, 1H), 4.31-4.38 (m, 4H), 6.93 (s, 1H), 8.71 (s, 1H).

Example 39A 2,6-Dimethyl-8-[4,4,4-trifluoro-3-(trifluoromethyl)butoxy]imidazo[1,2-a]pyridine-3-carboxylic acid

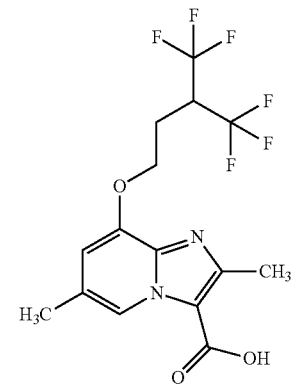 [SMILES: Cc1cc(OCCC(C(F)(F)F)C(F)(F)F)c2nc(C)c(C(=O)O)n2c1]

3.28 g (10.4 mmol) of barium hydroxide octahydrate were added to 1.95 g (4.73 mmol) of ethyl 2,6-dimethyl-8-[4,4,4-trifluoro-3-(trifluoromethyl)butoxy]imidazo[1,2-a]pyridine-3-carboxylate Example 38A in 30 ml of methanol, and the mixture was stirred at RT for 3 days. The suspension was diluted with 30 ml of water and adjusted to pH 6 with 1 M hydrochloric acid. The solid was filtered off, washed with 50 ml of water and dried at 70° C. under reduced pressure for 2 h. 1.64 g of the target compound (90% purity, 81% of theory) were obtained.

LC-MS (Method 1): $R_t$=0.78 min

MS (ESpos): m/z=385 (M+H)$^+$ $^1$H-NMR (400 MHz, DMSO-d$_6$): δ=2.29 (s, 3H), 2.28-2.37 (m, 2H), 2.56 (s, 3H), 4.22-4.35 (m, 3H), 6.74 (s, 1H), 8.99 (s, 1H).

Example 40A

5-Methoxy-2-nitropyridin-3-ol

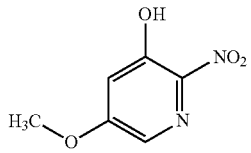

1) Under argon, 1.46 g (4.8 mmol) of tetra-n-butylammonium nitrate were initially charged in 10 ml of dichloromethane, 0.68 ml (4.8 mmol) of trifluoroacetic anhydride was added slowly at 0° C. and the mixture was stirred at 0° C. for 10 min.

2) Under argon, 500 mg (4 mmol) of 5-methoxypyridin-3-ol were dissolved in a separate reaction flask in 10 ml of dichloromethane, and the solution from step 1) was added dropwise at −30° C. The reaction mixture was stirred in the thawing ice bath (not exceeding 0° C.) for 4 h. Kieselguhr was added and the reaction solution was concentrated at low temperature and purified by silica gel chromatography (mobile phase: cyclohexane/ethyl acetate: 9/1). This gave 637 mg of the target compound (94% of theory, purity 100%).

LC-MS (Method 1): $R_t$=0.58 min

MS (ESpos): m/z=171 (M+H)$^+$ $^1$H-NMR (400 MHz, DMSO-d$_6$): δ=3.90 (s, 3H), 7.11 (d, 1H), 7.78 (d, 1H), 11.35 (br. 1H).

Example 41A

3-[(2,6-Difluorobenzyl)oxy]-5-methoxy-2-nitropyridine

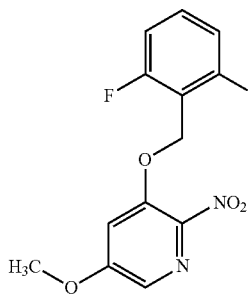

0.76 g (4.47 mmol) of 5-methoxy-2-nitropyridin-3-ol from Example 40A and 2.18 g (6.70 mmol) of caesium carbonate were initially charged in 12.5 ml of DMF, 0.93 g (4.47 mmol) of 2,6-difluorobenzyl bromide was added and the mixture was stirred at RT overnight. The reaction mixture was stirred into 100 ml of 1 N aqueous hydrochloric acid and stirred at RT for 30 min. The solid was filtered off, washed with water and dried under high vacuum. This gave 1.28 g (97% of theory) of the title compound.

LC-MS (Method 1): $R_t$=1.02 min

MS (ESpos): m/z=297 (M+H)$^+$ $^1$H-NMR (400 MHz, DMSO-d$_6$): δ=4.00 (s, 3H), 5.42 (s, 2H), 7.21 (t, 2H), 7.58 (quintet, 1H), 7.70 (d, 1H), 7.88 (d, 1H).

Example 42A

3-[(2,6-Difluorobenzyl)oxy]-5-methoxypyridine-2-amine

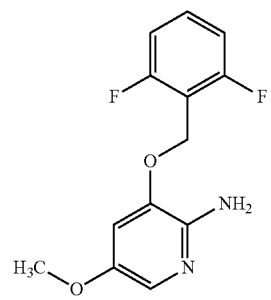

0.73 g (13.1 mmol) of iron powder was added to 1.25 g (4.22 mmol) of 3-[(2,6-difluorobenzyl)oxy]-5-methoxy-2-nitropyridine from 41 A in 12.7 ml of ethanol, and the mixture was heated to reflux. 3.23 ml (38.8 mmol) of concentrated aqueous hydrochloric acid were slowly added dropwise and the mixture was stirred at reflux for a further 30 min. The reaction mixture was cooled and stirred into an ice/water mixture and stirred for 30 min. The organic solvent was removed under reduced pressure, the aqueous phase was made alkaline with 1 N aqueous sodium hydroxide solution and stirred with dichloromethane and the mixture was filtered off through Celite. The filter residue was washed with dichloromethane and the aqueous phase was extracted twice with dichloromethane. The combined organic phases were dried over sodium sulphate and filtered, the filtrate was concentrated and the residue was dried under high vacuum. This gave 974 mg of the target compound (85% of theory).

LC-MS (Method 1): $R_t$=0.61 min

MS (ESpos): m/z=267 (M+H)$^+$ $^1$H-NMR (400 MHz, DMSO-d$_6$): δ=3.72 (s, 3H), 5.10 (s, 2H), 5.14 (s, 2H), 7.04 (d, 1H), 7.20 (t, 2H), 7.32 (d, 1H), 7.55 (quintet, 1H).

Example 43A

Ethyl 8-[(2,6-difluorobenzyl)oxy]-6-methoxy-2-methylimidazo[1,2-a]pyridine-3-carboxylate

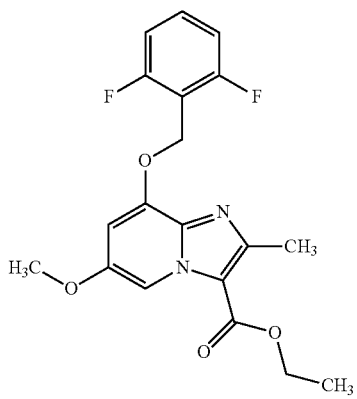 [SMILES: CCOC(=O)c1c(C)nc2c(OCc3c(F)cccc3F)cc(OC)cn12]

0.97 g (3.64 mmol) of 3-[(2,6-difluorobenzyl)oxy]-5-methoxypyridine-2-amine from Example 42A was initially charged in 18.5 ml of ethanol, 0.93 g of powdered molecular sieve 3 Å and 6.0 g (36.43 mmol) of ethyl 2-chloroacetoacetate were added and the mixture was heated at reflux overnight. The reaction mixture was concentrated on a dry-ice rotary evaporator at a water bath temperature of 85° C. The crude product was purified by silica gel chromatography (mobile phase: cyclohexane/ethyl acetate: 9/1 isocratic). This gave 583 mg of the target compound (41% of theory).

LC-MS (Method 1): $R_t$=1.09 min
MS (ESpos): m/z=377 (M+H)$^+$
$^1$H-NMR (400 MHz, DMSO-$d_6$): δ=1.36 (t, 3H), 2.54 (s, 3H; obscured by DMSO signal), 3.83 (s, 3H), 4.37 (q, 2H), 5.32 (s, 2H), 7.05 (d, 1H), 7.23 (t, 2H), 7.60 (quintet, 1H), 8.58 (d, 1H).

Example 44A

8-[(2,6-Difluorobenzyl)oxy]-6-methoxy-2-methylimidazo[1,2-a]pyridine-3-carboxylic acid

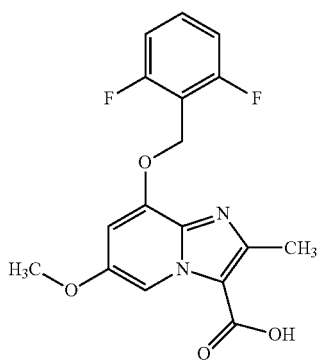

580 mg (1.54 mmol) of ethyl 8-[(2,6-difluorobenzyl)oxy]-6-methoxy-2-methylimidazo[1,2-a]pyridine-3-carboxylate from Example 43A were dissolved in 33 ml of THF/methanol (5/1), 7.7 ml of 1 M aqueous lithium hydroxide solution were added and the mixture was stirred at 40° C. overnight. The reaction mixture was cooled, adjusted to pH 4 using 6 N aqueous hydrochloric acid and ice-cooling and then freed of the organic solvents on a rotary evaporator. The solid formed was filtered off, washed with water and then dried under high vacuum. This gave 507 mg of the target compound (94% of theory).

LC-MS (Method 1): $R_t$=0.74 min
MS (ESpos): m/z=349 (M+H)$^+$
$^1$H-NMR (400 MHz, DMSO-$d_6$): δ=2.54 (s, 3H; superposed by DMSO signal), 3.85 (s, 3H), 5.38 (s, 2H), 7.20-7.32 (m, 3H), 7.61 (quintet, 1H), 8.68 (d, 1H), 13.40 (br. s, 1H).

Example 45A

5-Methyl-2-nitropyridin-3-ol

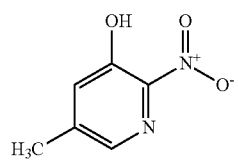

With ice-cooling, 25 g (0.23 mol) of 5-methylpyridin-3-ol were initially charged in 226 ml (4.12 mol) of concentrated sulphuric acid, and the mixture was then warmed to RT. After the starting material had been dissolved completely, the reaction mixture was once more cooled to 0° C. At 0° C. to 10° C., 14.25 ml (0.34 mol) of fuming nitric acid were then added slowly dropwise, and the mixture was warmed to 15° C. over 3.5 hours. The mixture was stirred at RT overnight. The reaction solution was poured onto 1000 g of ice and extracted twice with in each case 500 ml of ethyl acetate. The combined organic phases were dried and concentrated. This gave 31.5 g of the target compound (89% of theory).

LC-MS (Method 14): $R_t$=1.21 min
MS (ESpos): m/z=155 (M+H)$^+$

Example 46A

3-[(2,6-Difluorobenzyl)oxy]-5-methyl-2-nitropyridine

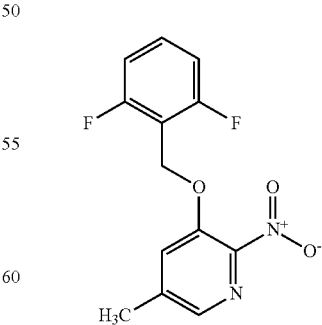

31.5 g (0.155 mol) of 5-methyl-2-nitropyridin-3-ol from Example 45A and 75.78 g (0.23 mol) of caesium carbonate were initially charged in 432 ml of DMF, 33.7 g (0.163 mol) of 2,6-difluorobenzyl bromide were then added and the reaction mixture was stirred at RT overnight. The reaction solution was stirred into 3600 ml of 0.5 N aqueous hydrochloric acid. The precipitate formed was stirred for another 30 min, filtered off with suction, washed with water and air-dried at RT and atmospheric pressure. This gave 45.8 g of the target compound (105% of theory).

LC-MS (Method 1): R$_t$=0.98 min

MS (ESpos): m/z=281 (M+H)$^+$ $^1$H-NMR (400 MHz, DMSO-d$_6$): δ=2.44 (s, 3H), 5.37 (s, 2H), 7.21 (quint., 2H), 7.52-7.61 (m, 1H), 8.01 (s, 1H), 8.06 (s, 1H).

Example 47A

3-[(2,6-Difluorobenzyl)oxy]-5-methylpyridine-2-amine

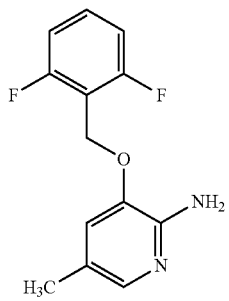 [SMILES: Cc1cnc(N)c(OCc2c(F)cccc2F)c1]

56.2 g (1.0 mol) of iron powder were added to 91 g (324.7 mmol) of 3-[(2,6-difluorobenzyl)oxy]-5-methyl-2-nitropyridine from Example 46A initially charged under argon in 980 ml of ethanol, and the mixture was heated to reflux. 248 ml of concentrated aqueous hydrochloric acid were slowly added dropwise, and the mixture was stirred under reflux for another 30 min. After cooling, about 2000 ml of water/ice (1/1) were added, and the reaction mixture was stirred at RT for 30 min. The solution was concentrated to the point where most of the solvent had been removed. The aqueous phase was made alkaline using concentrated aqueous sodium hydroxide solution, 1200 ml of dichloromethane were added and the mixture was stirred vigorously for 1 h. The mixture was filtered off with suction through kieselguhr and the filter residue was repeatedly washed thoroughly with a total of about 2800 ml of dichloromethane. The mother liquor was separated and the organic phase was dried and concentrated. This gave 77.8 g of the target compound (96% of theory).

LC-MS (Method 1): R$_t$=0.57 min

MS (ESpos): m/z=251 (M+H)$^+$ $^1$H-NMR (400 MHz, DMSO-d$_6$): δ=2.13 (s, 3H), 5.08 (s, 2H), 5.25 (s, 2H), 7.09 (d, 1H), 7.14-7.22 (m, 2H), 7.37-7.41 (m, 1H), 7.49-7.57 (m, 1H).

Example 48A

Ethyl 8-[(2,6-difluorobenzyl)oxy]-2-ethyl-6-methylimidazo[1,2-a]pyridine-3-carboxylate

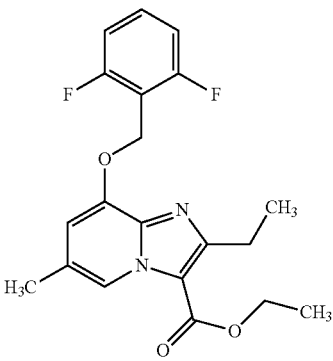 [SMILES: CCOC(=O)c1c(CC)nc2c(OCc3c(F)cccc3F)cc(C)cn12]

Under argon, 3.5 g (13.99 mmol) of 3[(2,6-difluorobenzyl)oxy]-5-methylpyridine-2-amine from Example 47A and 9.6 ml (69.93 mmol) of methyl 2-chloro-2-propionylacetate were dissolved in 140 ml of ethanol, and the solution was stirred under reflux with 500 mg of 3 Å molecular sieve overnight. 500 mg of 3 Å molecular sieve were added and the mixture was stirred under reflux for a further 16 hours. The reaction mixture was stirred under reflux for 8 days, and each day 3 Å molecular sieve was added. The mixture was cooled and filtered off with suction, and the mother liquor was substantially concentrated. The residue obtained was purified by silica gel chromatography (mobile phase: cyclohexane/ethyl acetate 9/1 to 7/3). This gave 3.8 g of the target compound (68% of theory, as a 1:1 mixture with methyl 8-[(2,6-difluorobenzyl)oxy]-2-ethyl-6-methylimidazo[1,2-a]pyridine-3-carboxylate).

LC-MS (Method 1): R$_t$=1.18 min

MS (ESpos): m/z=361 (M+H)$^+$

Example 49A

8-[(2,6-Difluorobenzyl)oxy]-2-ethyl-6-methylimidazo[1,2-a]pyridine-3-carboxylic acid

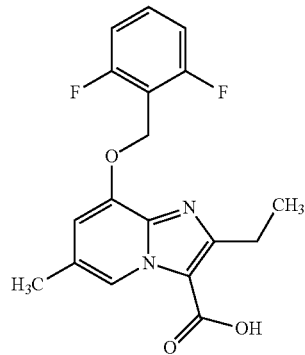 [SMILES: CCc1nc2c(OCc3c(F)cccc3F)cc(C)cn2c1C(=O)O]

2 g (5.34 mmol) of ethyl 8-[(2,6-difluorobenzyl)oxy]-2-ethyl-6-methylimidazo[1,2-a]pyridine-3-carboxylate from Example 48A (1:1 mixture of methyl and ethyl ester) were dissolved in 114 ml of THF/methanol (5/1), 5.34 ml (5.34 mmol) of 1 N aqueous lithium hydroxide solution were added and the mixture was stirred at RT overnight. The reaction mixture was stirred at 40° C. for 4 days, with another 5.34 ml (5.34 mmol) of 1 N aqueous lithium hydroxide solution being added after 3 days. After cooling, the mixture was acidified to pH 4 with ice-cooling using 6 N aqueous hydrochloric acid and then freed of the organic solvent on a rotary evaporator. The solid formed was filtered off with suction, washed with water and then dried under high vacuum. This gave 1.94 g of the target compound (99% of theory).

LC-MS (Method 1): $R_t$=0.79 min

MS (ESpos): m/z=347 (M+H)$^+$ $^1$H-NMR (400 MHz, DMSO-d$_6$): δ=1.19 (t, 3H), 2.36 (s, 3H), 2.95 (q, 2H), 5.31 (s, 2H), 7.08 (s, 1H), 7.26 (quin, 2H), 7.55-7.65 (m, 1H), 8.78 (s, 1H), 13.02-13.06 (m, 1H).

Example 50A

Ethyl 8-[(2,6-difluorobenzyl)oxy]-6-methyl-2-propylimidazo[1,2-a]pyridine-3-carboxylate

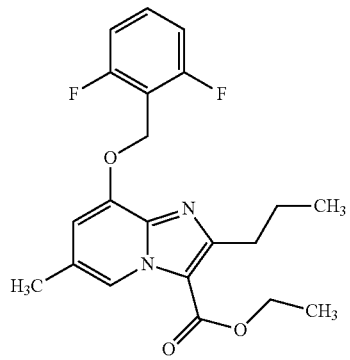 [SMILES: CCCc1nc2c(OCc3c(F)cccc3F)cc(C)cn2c1C(=O)OCC]

Under argon, 3.0 g (11.99 mmol) of 3-[(2,6-difluorobenzyl)oxy]-5-methylpyridine-2-amine from Example 47A were initially charged in 60 ml of ethanol. 18.48 g (95.90 mmol) of ethyl 2-chloro-3-oxohexanoate (described in: M. Altuna-Urquijo et al. Tetrahedron 2009, 65, 975-984) and 600 mg of 3 Å molecular sieve were then added, and the mixture was stirred under reflux for 5 days. The reaction solution was concentrated and partitioned between water and ethyl acetate. The phases were separated and the aqueous phase was extracted with ethyl acetate. The organic phases were combined, dried over sodium sulphate, filtered off and concentrated. The residue was purified by silica gel chromatography (mobile phase: cyclohexane/ethyl acetate=95/5 to 8/2). This gave 2.4 g of the target compound (47% of theory, purity about 92%).

LC-MS (Method 1): $R_t$=1.23 min

MS (ESpos): m/z=389 (M+H)$^+$ $^1$H-NMR (400 MHz, DMSO-d$_6$): δ=0.90 (t, 3H), 1.35 (t, 3H), 1.60-1.70 (m, 2H), 2.37 (s, 3H), 2.87-2.94 (m, 2H), 4.35 (q, 2H), 5.31 (s, 2H), 7.10 (s, 1H), 7.21-7.29 (m, 2H), 7.55-7.65 (m, 1H), 8.74 (s, 1H).

Example 51A

8-[(2,6-Difluorobenzyl)oxy]-6-methyl-2-propylimidazo[1,2-a]pyridine-3-carboxylic acid

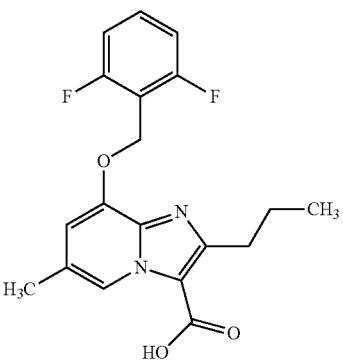 [SMILES: CCCc1nc2c(OCc3c(F)cccc3F)cc(C)cn2c1C(=O)O]

2.30 g (5.92 mmol) of ethyl 8-[(2,6-difluorobenzyl)oxy]-6-methyl-2-propylimidazo[1,2-a]pyridine-3-carboxylate from Example 50A were initially charged in 108 ml of THF, 29 ml of water and 21.6 ml of methanol at RT. 1.24 g (29.61 mmol) of lithium hydroxide monohydrate were added and the mixture was stirred at RT for 16 hours. The reaction mixture was freed from the organic solvents and the aqueous solution obtained was acidified with semiconcentrated hydrochloric acid. The aqueous phase was extracted twice with dichloromethane. The organic phases were combined, dried over sodium sulphate, filtered and concentrated. This gave 2.50 g of the target compound (115% of theory).

LC-MS (Method 1): $R_t$=0.83 min

MS (ESpos): m/z=361 (M+H)$^+$ $^1$H-NMR (400 MHz, DMSO-d$_6$): δ=0.89 (t, 3H), 1.61-1.72 (m, 2H), 2.41 (s, 3H), 2.95 (t, 2H), 5.35 (s, 2H), 7.19-7.35 (m, 3H), 7.56-7.66 (m, 1H), 8.85 (s, 1H), 12.94-13.92 (br. s, 1H).

Example 52A

Ethyl 8-[(2,6-difluoro-3-methoxybenzyl)oxy]-2,6-dimethylimidazo[1,2-a]pyridine-3-carboxylate

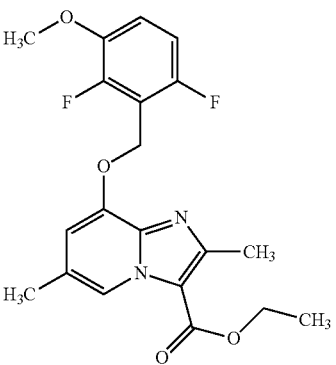 [SMILES: CCOC(=O)c1c(C)nc2c(OCc3c(F)ccc(OC)c3F)cc(C)cn12]

1.35 g (5.75 mmol) of ethyl 8-hydroxy-2,6-dimethylimidazo[1,2-a]pyridine-3-carboxylate from Example 20A and 4.12 g (12.66 mmol) of caesium carbonate were initially charged in 82 ml of DMF. The mixture was heated to 60° C., and 1.50 g (6.33 mmol) of 2-(bromomethyl)-1,3-difluoro-4-methoxybenzene were then added. The mixture was stirred at 60° C. for 20 min. The reaction mixture was poured onto about 500 ml of water and stirred for 30 min. The solid formed was filtered off with suction, washed well with water and dried under high vacuum. This gave 2.11 g of the title compound (86% of theory, purity 92%).

LC-MS (Method 1): $R_t$=1.09 min

MS (ESpos): m/z=391 (M+H)$^+$ $^1$H-NMR (400 MHz, DMSO-d$_6$): δ=1.35 (t, 3H), 2.37 (s, 3H), 3.87 (s, 3H), 4.29-4.38 (m, 2H), 5.30 (s, 2H), 7.09 (s, 1H), 7.12-7.22 (m, 1H), 7.27-7.37 (m, 1H), 8.71 (s, 1H), [further signal under solvent peak].

Example 53A

8-[(2,6-Difluoro-3-methoxybenzyl)oxy]-2,6-dimethylimidazo[1,2-a]pyridine-3-carboxylic acid

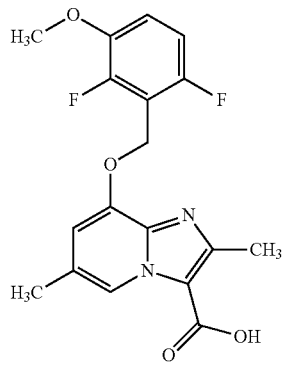

2.00 g (4.69 mmol) of ethyl 8-[(2,6-difluoro-3-methoxybenzyl)oxy]-2,6-dimethylimidazo[1,2-a]pyridine-3-carboxylate from Example 52A were suspended in 50 ml of dioxane, 11.73 ml (23.46 mmol) of 2 N aqueous sodium hydroxide solution were added and the mixture was stirred at 90° C. for 5 h. The reaction solution was acidified with 1 N aqueous hydrochloric acid, and the aqueous phase was extracted three times with ethyl acetate. The organic phase was dried over sodium sulphate, filtered and concentrated. This gave 790 mg of the title compound. The aqueous phase was once more stirred with ethyl acetate for 1.5 h, and the phases were separated. The organic phase was dried over sodium sulphate, filtered and concentrated. This gave 70 mg of the title compound. The aqueous phase was once more stirred with dichloromethane for 2 h, and the phases were separated. The organic phase was dried over sodium sulphate, filtered and concentrated under reduced pressure. This gave 60 mg of the title compound. The aqueous phase was concentrated under reduced pressure and the residue was purified by preparative HPLC (RP18 column, mobile phase: acetonitrile/water gradient with addition of 0.1% TFA). This gave 300 mg of the title compound as trifluoroacetate salt. A total of 920 mg of the title compound (52% of theory) were obtained (some as trifluoroacetate salt).

LC-MS (Method 1): $R_t$=0.69 min

MS (ESpos): m/z=363 (M+H)$^+$ $^1$H-NMR (400 MHz, DMSO-d$_6$): δ=2.36 (s, 3H), 3.87 (s, 3H), 5.29 (s, 2H), 7.06 (s, 1H), 7.12-7.23 (m, 1H), 7.28-7.38 (m, 1H), 8.75 (s, 1H), 12.09-13.12 (br. s, 1H), [further signal under solvent peak].

Example 54A

3-Cyclopropyl-2,6-difluorobenzaldehyde

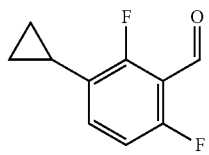 [SMILES: O=Cc1c(F)ccc(C2CC2)c1F]

3.50 g (15.84 mmol) of 3-bromo-2,6-difluorobenzaldehyde were dissolved in 87.5 ml of toluene. A solution of 3.36 g (31.67 mmol) of sodium carbonate in 1.5 ml of water was added, and the mixture was stirred at RT for 10 min. 2.04 g (23.75 mmol) of cyclopropylboronic acid and 366 mg (0.32 mmol) of tetrakis(triphenylphosphine)palladium(0) were then added, and the mixture was stirred under reflux overnight. Another 0.68 g (7.92 mmol) of cyclopropylboronic acid, 0.34 g (3.17 mmol) of sodium carbonate and 183 mg (0.16 mmol) of tetrakis(triphenylphosphine)palladium(0) were added, and the mixture was once more stirred under reflux overnight. The reaction mixture was diluted with ethyl acetate and extracted. The aqueous phase was washed twice with ethyl acetate. The combined organic phases were dried over sodium sulphate, filtered and concentrated under reduced pressure at a bath temperature of 35° C. This gave 3.50 g of the title compound (92% of theory, purity 76%).

LC-MS (Method 14): $R_t$=2.11 min

MS (ESpos): m/z=183 (M+H)$^+$

Example 55A (3-Cyclopropyl-2,6-difluorophenyl)methanol

Under argon, 221 mg (5.84 mmol) of sodium borohydride were initially charged in 47 ml of tetrahydrofuran at 0° C. A solution of 3.5 g (14.60 mmol) of 3-cyclopropyl-2,6-difluorobenzaldehyde from Example 54A in 189 ml of tetrahydrofuran was added. Subsequently, 14.8 ml of methanol were added dropwise at 0° C., and the mixture was stirred at room temperature for 2 h. The reaction solution was poured onto about 88 ml of ice-water and adjusted to about pH=1 using 2 N aqueous sulphuric acid, and the mixture was extracted three times with dichloromethane. The combined organic phases were dried over sodium sulphate, filtered and concentrated to dryness on a rotary evaporator at a bath temperature of 30° C. The residue was taken up in a little dichloromethane/methanol and purified by silica gel chromatography (mobile phase: cyclohexane/ethyl acetate gradient=10/1 to cyclohexane/ethyl acetate 5/1). The product fractions were combined and concentrated at a bath temperature of 30° C. This gave 2.46 g of the title compound (86% of theory, purity 94%).

LC-MS (Method 14): $R_t$=1.90 min

MS (ESpos): m/z=167 (M−H$_2$O+H)$^+$

Example 56A

Ethyl 8-[(3-cyclopropyl-2,6-difluorobenzyl)oxy]-2,6-dimethylimidazo[1,2-a]pyridine-3-carboxylate trifluoroacetate

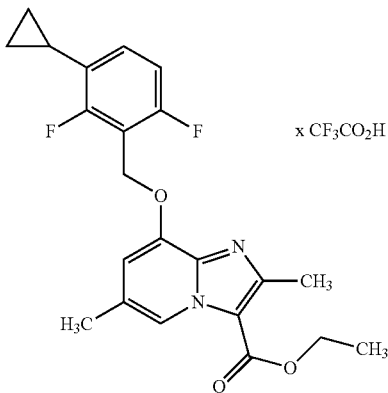 [SMILES: CCOC(=O)c1c(C)nc2c(OCc3c(F)ccc(C4CC4)c3F)cc(C)cn12]

2.67 g (11.41 mmol) of ethyl 8-hydroxy-2,6-dimethylimidazo[1,2-a]pyridine-3-carboxylate from Example 20A were dissolved in 104 ml of THF. 2.46 g (12.55 mmol) of (3-cyclopropyl-2,6-difluorophenyl)methanol from Example 55A and 6.29 g (23.97 mmol) of triphenylphosphine were added. After addition of 4.75 ml (23.97 mmol) of diisopropyl azodicarboxylate (DIAD), the reaction mixture was stirred at RT overnight. The mixture was concentrated and purified by silica gel chromatography (mobile phase: cyclohexane/ethyl acetate gradient=10/1 to 5/1). The product fractions were concentrated and purified once again by preparative HPLC (RP18 column, mobile phase: acetonitrile/water gradient with addition of 0.1% TFA). This gave 1.1 g of the title compound (19% of theory).

LC-MS (Method 1): $R_t$=1.23 min
MS (ESpos): m/z=401 (M−TFA+H)$^+$
$^1$H-NMR (400 MHz, DMSO-$d_6$): δ=0.70-0.78 (m, 2H), 0.95-1.03 (m, 2H), 1.36 (t, 3H), 2.00-2.13 (m, 1H), 2.40 (s, 3H), 4.33-4.40 (m, 2H), 5.32 (s, 2H), 7.08-7.28 (m, 3H), 8.75 (s, 1H), [further signal under solvent peak].

Example 57A

8-[(3-Cyclopropyl-2,6-difluorobenzyl)oxy]-2,6-dimethylimidazo[1,2-a]pyridine-3-carboxylic acid trifluoroacetate

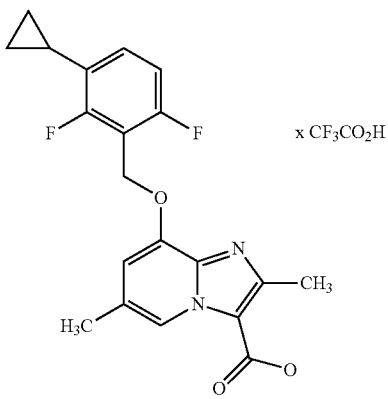 [SMILES: Cc1cc(OCc2c(F)ccc(C3CC3)c2F)c2nc(C)c(C(=O)O)n2c1]

1.1 g (2.14 mmol) of ethyl 8-[(3-cyclopropyl-2,6-difluorobenzyl)oxy]-2,6-dimethylimidazo[1,2-a]pyridine-3-carboxylate trifluoroacetate from Example 56A were suspended in 46 ml of dioxane, 6.4 ml (12.8 mmol) of 2 N aqueous sodium hydroxide solution were added and the mixture was stirred at 90° C. overnight. The mixture was concentrated, and TFA/water/acetonitrile were added to the residue. The solid formed was filtered off and washed with a little water. The product-containing filtrate was concentrated slightly and purified by preparative HPLC (RP18 column, mobile phase: acetonitrile/water gradient with addition of 0.1% TFA). The appropriate product-containing fractions were combined with the solid which had been filtered off and concentrated. This gave 950 mg of the title compound (91% of theory).

LC-MS (Method 1): $R_t$=0.87 min
MS (ESpos): m/z=373 (M−TFA+H)$^+$

Example 58A

Ethyl 8-[(3-fluoropyridin-2-yl)methoxy]-2-methylimidazo[1,2-a]pyridine-3-carboxylate

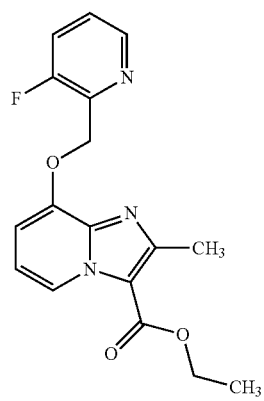 [SMILES: CCOC(=O)c1c(C)nc2c(OCc3ncccc3F)cccn12]

Variant A:

4.18 g of ethyl 8-hydroxy-2-methylimidazo[1,2-a]pyridine-3-carboxylate (Example 24A, 19 mmol) were dissolved in 265 ml of abs. DMF, 3.80 g of 2-(chloromethyl)-3-fluoropyridine hydrochloride (20.88 mmol, commercially available, additionally described in: U.S. Pat. No. 5,593,993, 1997; WO2007/2181 A2, 2007) and 18.55 g of caesium carbonate (56.94 mmol) were added and the mixture was then stirred overnight at 60° C. After cooling, the reaction mixture was filtered, the precipitate was washed with ethyl acetate, the filtrate was concentrated and the residue was purified by silica gel chromatography (mobile phase: Cyclohexane:ethyl acetate=1:3). This gave 4.66 g (73% of theory) of the target compound.

MS (ESpos): m/z=330 (M+H)$^+$
$^1$H-NMR (400 MHz, DMSO-$d_6$): δ=1.36 (t, 3H), 2.61 (s, 3H), 4.38 (q, 2H), 4.50 (br s, 1H), 5.49 (s, 2H), 7.20 (t, 1H), 7.32 (d, 1H), 7.57-7.61 (m, 1H), 7.87 (t, 1H), 8.49 (d, 1H), 8.90 (d, 1H).

Variant B:

144 mg of ethyl 8-hydroxy-2-methylimidazo[1,2-a]pyridine-3-carboxylate (Example 3A, 0.65 mmol) were dissolved in 3.9 ml of THF, 100 mg of (3-fluoropyridin-2-yl)methanol (0.79 mmol), 189 mg of triphenylphosphine (0.72 mmol) and then 0.15 ml of diisopropyl azodicarboxylate (0.72 mmol) were added. The reaction mixture was stirred at RT overnight and then purified by preparative HPLC (RP18 column, mobile phase: acetonitrile/water gradient with addition of 0.1% TFA). This gave 198 mg (68% of theory, purity 99%) of the target compound.

LC-MS (Method 1): $R_t$=0.84 min

Example 59A

8-[(3-Fluoropyridin-2-yl)methoxy]-2-methylimidazo[1,2-a]pyridine-3-carboxylic acid hydrochloride

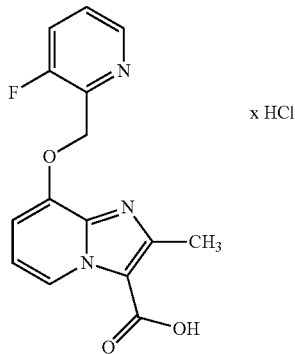 [SMILES: Cc1nc2c(OCc3ncccc3F)cccn2c1C(=O)O]

4.66 g of ethyl 8-[(3-fluoropyridin-2-yl)methoxy]-2-methylimidazo[1,2-a]pyridine-3-carboxylate (Example 58A, 14.2 mmol) were dissolved in 304 ml of THF/MeOH (5/1), 70.8 ml of 1 N aqueous lithium hydroxide solution (70.8 mmol) were added and the mixture was stirred at 40° C. overnight. The reaction mixture was acidified with 1 N aqueous hydrochloric acid (about pH 3-4) and the solution was concentrated. The precipitate formed was cooled with ice-water, then filtered off with suction and dried under reduced pressure. This gave 3.97 g of the product (83% of theory).

LC-MS (Method 1): $R_t$=0.46 min

MS (ESpos): m/z=302 (M+H)$^+$ $^1$H-NMR (400 MHz, DMSO-d$_6$): δ=2.50 (s, 3H, obscured under DMSO signal), 5.42 (s, 2H), 7.02 (t, 1H), 7.13 (d, 1H), 7.56-7.62 (m, 1H), 7.84 (t, 1H), 8.49 (d, 1H), 8.89 (d, 1H), 13.08 (br. s, 1H).

Example 60A

Ethyl 8-[(3-fluoropyridin-2-yl)methoxy]-2,6-dimethylimidazo[1,2-a]pyridine-3-carboxylate

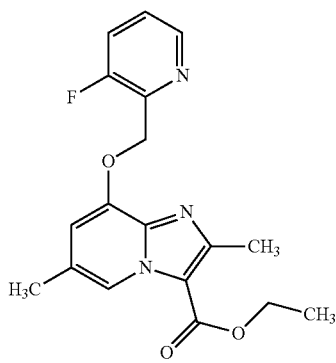 [SMILES: CCOC(=O)c1c(C)nc2c(OCc3ncccc3F)cc(C)cn12]

15.78 g (86.7 mmol) of 2-(chloromethyl)-3-fluoropyridine hydrochloride (commercially available, also described in: U.S. Pat. No. 5,593,993 A1, 1997; WO2007/2181 A2, 2007) and 94.06 g (288.9 mmol) of caesium carbonate were added to 16.92 g (72.2 mmol) of ethyl 8-hydroxy-2,6-dimethylimidazo[1,2-a]pyridine-3-carboxylate from Example 20A in 956 ml of DMF. The reaction mixture was stirred at 60° C. overnight. The reaction mixture, cooled to RT, was filtered, the filter cake was washed with ethyl acetate and the filtrate was concentrated. About 500 ml of water were added to the residue, and the solid formed was filtered off and dried under high vacuum. This gave 24.1 g (93% of theory) of the target compound.

LC-MS (Method 1): $R_t$=0.84 min

MS (ESpos): m/z=344 (M+H)$^+$ $^1$H-NMR (400 MHz, DMSO-d$_6$): δ=1.35 (t, 3H), 2.35 (s, 3H), 2.54 (s, 3H, obscured by DMSO signal), 4.35 (q, 2H), 5.40 (s, 2H), 7.08 (s, 1H), 7.55-7.62 (m, 1H), 7.82-7.89 (m, 1H), 8.48-8.52 (m, 1H), 8.70 (s, 1H).

Example 61A

8-[(3-Fluoropyridin-2-yl)methoxy]-2,6-dimethylimidazo[1,2-a]pyridine-3-carboxylic acid hydrochloride

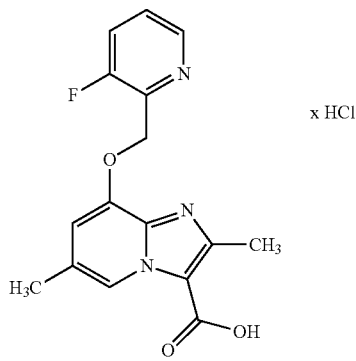

24.06 g (70.1 mmol) of ethyl 8-[(3-fluoropyridin-2-yl)methoxy]-2,6-dimethylimidazo[1,2-a]pyridine-3-carboxylate from Example 60A were initially charged in 1.5 l of THF/methanol (5:1), 350.4 ml (350.4 mmol) of 1 N aqueous lithium hydroxide solution were added and the reaction mixture was stirred at 40° C. for 2.5 h. After cooling, the mixture was acidified to a pH of about 4 using 1 N aqueous hydrochloric acid, and the solution was freed of THF/methanol under reduced pressure. The residue was cooled and the solid formed was filtered off and dried under reduced pressure. This gave 22.27 g (100% of theory) of the title compound.

LC-MS (Method 1): $R_t$=0.55 min

MS (ESpos): m/z=316 (M−HCl+H)$^+$ $^1$H-NMR (400 MHz, DMSO-d$_6$): δ=2.34 (s, 3H), 2.53 (s, 3H, obscured by DMSO signal), 5.38-5.42 (m, 2H), 7.06 (s, 1H), 7.56-7.62 (m, 1H), 7.82-7.89 (m, 1H), 8.48-8.52 (m, 1H), 8.74 (s, 1H), 13.02 (br. s, 1H).

Example 62A (3,3-Difluorocyclobutyl)methyl methanesulphonate

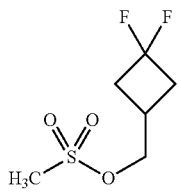

1.35 g (11.06 mmol) of (3,3-difluorocyclobutyl)methanol were initially charged in 41.8 ml of abs. dichloromethane, 3.08 ml (22.11 mmol) of triethylamine and 1.03 ml (13.27 mmol) of methanesulphonyl chloride were added and the mixture was stirred at room temperature overnight. Water was added to the reaction mixture and the aqueous phase was extracted twice with dichloromethane. The combined organic phases were washed with saturated aqueous sodium chloride solution, dried over sodium sulphate and filtered and the filtrate was concentrated. This gave 2.37 g (quantitative yield) of the target compound.

DCI-MS (Method 16): $R_t$=4.18 min. m/z=218 (M+NH$_4$)$^+$.
$^1$H-NMR (400 MHz, DMSO-d$_6$): δ=2.34-2.59 (m, 3H), 2.62-2.74 (m, 2H), 3.21 (s, 3H), 4.26 (d, 2H).

Example 63A

Ethyl 8-[(3,3-difluorocyclobutyl)methoxy]-2,6-dimethylimidazo[1,2-a]pyridine-3-carboxylate

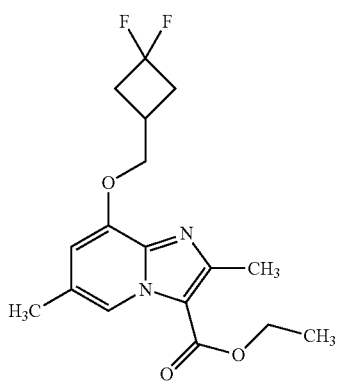 [SMILES: CCOC(=O)c1c(C)nc2c(OCC3CC(F)(F)C3)cc(C)cn12]

1.85 g (7.89 mmol) of ethyl 8-hydroxy-2,6-dimethylimidazo[1,2-a]pyridine-3-carboxylate Example 20A and 2.37 g (9.47 mmol) of (3,3-difluorocyclobutyl)methyl methanesulphonate Example 62A were initially charged in 104 ml of DMF, and 10.28 g (31.56 mmol) of caesium carbonate were added. The reaction mixture was stirred at 60° C. overnight. After cooling, the reaction mixture was filtered, the solid was washed thoroughly with ethyl acetate, the filtrate was concentrated and about 150 ml of water were added to the residue. The solid formed was filtered off and dried under high vacuum. This gave 2.51 g (89% of theory; purity 95%) of the title compound.

LC-MS (Method 1): $R_t$=1.00 min
MS (ESpos): m/z=339 (M+H)$^+$ $^1$H-NMR (400 MHz, DMSO-d$_6$): δ=1.35 (t, 3H), 2.32 (s, 3H), 2.42-2.60 (m, 5H), 2.62-2.84 (m, 3H), 4.22 (d, 2H), 4.33 (q, 2H), 6.90 (s, 1H), 8.68 (s, 1H).

Example 64A

8-[(3,3-Difluorocyclobutyl)methoxy]-2,6-dimethylimidazo[1,2-a]pyridine-3-carboxylic acid

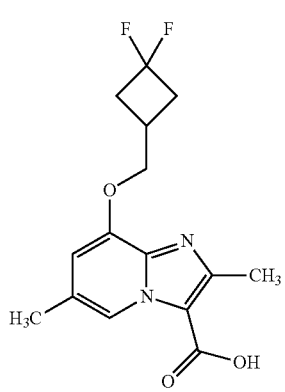

2.39 g (7.06 mmol) of ethyl 8-[(3,3-difluorocyclobutyl)methoxy]-2,6-dimethylimidazo[1,2-a]pyridine-3-carboxylate Example 63A were dissolved in 151 ml of THF/methanol (5:1), 35.3 ml (35.3 mmol) of 1 N aqueous lithium hydroxide solution were added and the mixture was stirred at RT for 2 d. The reaction mixture was acidified to pH 4 using 1 N aqueous hydrochloric acid solution and concentrated. The solid was filtered off, washed with water and dried under high vacuum. This gave 1.63 g (71% of theory; purity 95%) of the title compound.

LC-MS (Method 1): $R_t$=0.63 min
MS (ESpos): m/z=311 (M+H)$^+$
$^1$H-NMR (500 MHz, DMSO-d$_6$): δ=2.32 (s, 3H), 2.42-2.60 (m, 5H), 2.62-2.82 (m, 3H), 4.22 (d, 2H), 6.87 (s, 1H), 8.71 (s, 1H), 12.93 (br. s, 1H).

Example 65A

9H-Fluoren-9-ylmethyl-3-amino-5-cyanopiperidine-1-carboxylate (Mixture of Stereoisomers)

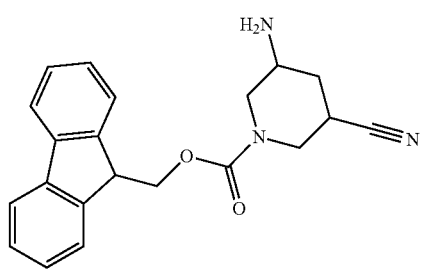 [SMILES: N#CC1CC(N)CN(C(=O)OCC2c3ccccc3-c3ccccc32)C1]

1. Step:
15 g (32.2 mmol) of 5-[(tert-butoxycarbonyl)amino]-1-[(9H-fluoren-9-ylmethoxy)-carbonyl]piperidine-3-carboxylic acid (mixture of stereoisomers) [described in a) D. K. Baeschlin et al. J. Med. Chem. 2013, 56, 2196. b) WO2006/117183. c) W. Breitenstein et al. US2009233920] were initially charged in 150 ml of DMF. 7.1 g (37.0 mmol) of EDCI hydrochloride and 5.0 g (37.0 mmol) of HOBT were added and the mixture was stirred at RT for 1.5 h. 30 ml of a solution of ammonia in DMF (2.2 molar) were then added, and the mixture was stirred at RT overnight and then poured onto water. A mixture of 1:1 diethyl ether/ethyl acetate was added, and the mixture was stirred at RT for 1 h. The mixture was filtered and the solid was washed with diethyl ether and then dried. This gave 11 g (73% of theory) of 9H-fluoren-9-ylmethyl-3-[(tert-butoxycarbonyl) amino]-5-carbamoylpiperidine-1-carboxylate (mixture of stereoisomers).

2. Step:

10 g (21.5 mmol) of 9H-fluoren-9-ylmethyl-3-[(tert-butoxycarbonyl)amino]-5-carbamoylpiperidine-1-carboxylate (mixture of stereoisomers) and 18 g (75.3 mmol) of (methoxycarbonylsulphamoyl)triethylammonium hydroxide (Burgess reagent) in 100 ml of dichloromethane were stirred at RT for 48 h. The mixture was concentrated and purified by silica gel chromatography (cyclohexane/ethyl acetate gradient). This gave 6.8 g (71% of theory) of 9H-fluoren-9-ylmethyl-3-[(tert-butoxycarbonyl)amino]-5-cyanopiperidine-1-carboxylate (mixture of stereoisomers).

3. Step:

18 g (40.2 mmol) of 9H-fluoren-9-ylmethyl-3-[(tert-butoxycarbonyl)amino]-5-cyanopiperidine-1-carboxylate (mixture of stereoisomers) were dissolved in 150 ml of TFA/dichloromethane (1:1), and the solution was stirred at RT for 1 h. The mixture was concentrated and the residue was purified by silica gel chromatography (dichloromethane/methanol gradient). This gave 11 g (61% of theory) of 9H-fluoren-9-ylmethyl-3-amino-5-cyanopiperidine-1-carboxylate (mixture of stereoisomers).

LC-MS (Method 1): $R_t$=0.74 min
MS (ESpos): m/z=348 (M+H)$^+$

Example 66A

9H-Fluoren-9-ylmethyl-3-cyano-5-[({8-[(2,6-difluorobenzyl)oxy]-2,6-dimethylimidazo[1,2-a]pyridin-3-yl}carbonyl)amino]piperidine-1-carboxylate trifluoroacetate (Mixture of Stereoisomers)

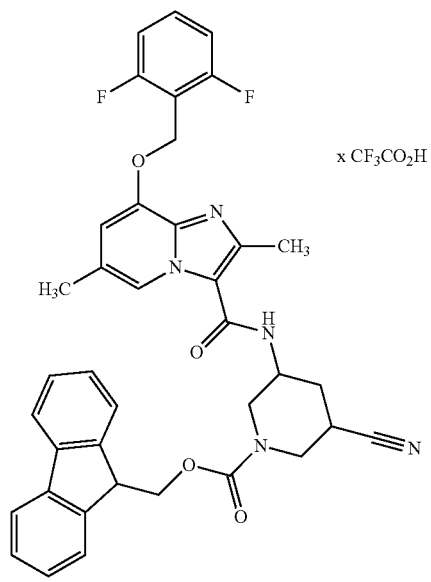 [SMILES: Cc1cc(OCc2c(F)cccc2F)c2nc(C)c(C(=O)NC3CC(C#N)CN(C(=O)OCC4c5ccccc5-c5ccccc54)C3)n2c1]

208 mg (0.55 mmol) of HATU and 0.37 ml (2.11 mmol) of N,N-diisopropylethylamine were added to 140 mg (0.42 mmol) of 8-[(2,6-difluorobenzyl)oxy]-2,6-dimethylimidazo[1,2-a]pyridine-3-carboxylic acid from Example 16A in 1.25 ml of DMF. The reaction mixture was stirred at RT for 20 min, 253 mg (0.55 mmol) of 9H-fluoren-9-ylmethyl-3-amino-5-cyanopiperidine-1-carboxylate (mixture of stereoisomers) were then added and the mixture was stirred at RT for 1 hour. The reaction solution was admixed with water and the solid that formed was stirred at room temperature for about 30 min. Subsequently, the solid was filtered off, washed well with water and dried under high vacuum. Water/TFA was added to the solid and the product was purified by preparative HPLC (RP18 column, mobile phase: acetonitrile/water gradient with addition of 0.1% TFA). This gave 175 mg of the target compound (53% of theory).

LC-MS (Method 1): $R_t$=1.14 min
MS (ESpos): m/z=662 (M+H)$^+$

Example 67A rac-N-(1-Chloro-3-cyanopropan-2-yl)-8-[(2,6-difluorobenzyl)oxy]-2,6-dimethylimidazo[1,2-a]pyridine-3-carboxamide hydrochloride

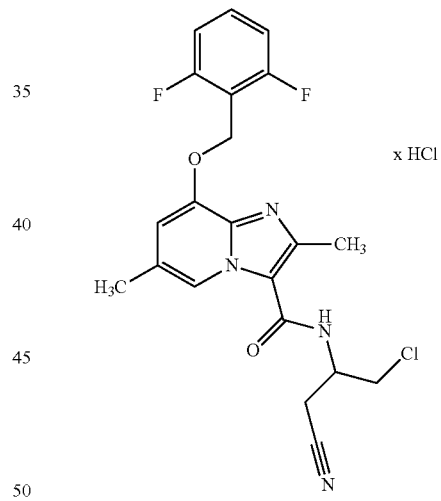

143 mg (0.35 mmol) of rac-N-(1-cyano-3-hydroxypropan-2-yl)-8-[(2,6-difluorobenzyl)oxy]-2,6-dimethylimidazo[1,2-a]pyridine-3-carboxamide from Example 14 were initially charged in 1.3 ml of abs. dichloromethane, and 25 µl (0.35 mmol) of thionyl chloride were added at 0° C. The mixture was stirred at RT overnight. 25 µl (0.35 mmol) of thionyl chloride were added, and the reaction mixture was stirred at room temperature for 20 min. The reaction mixture was concentrated and the residue was dried and used without further purification for the subsequent step.

LC-MS (Method 1): $R_t$=0.84 min
MS (ESpos): m/z=433 (M−HCl+H)$^+$

Example 68A rac-N-(1-Azido-3-cyanopropan-2-yl)-8-[(2,6-difluorobenzyl)oxy]-2,6-dimethylimidazo[1,2-a]pyridine-3-carboxamide

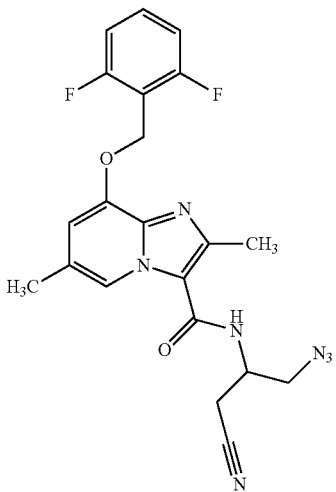 [SMILES: Cc1cc(OCc2c(F)cccc2F)c2nc(C)c(C(=O)NC(CC#N)CN=[N+]=[N-])n2c1]

The crude product of rac-N-(1-chloro-3-cyanopropan-2-yl)-8-[(2,6-difluorobenzyl)oxy]-2,6-dimethylimidazo[1,2-a]pyridine-3-carboxamide hydrochloride from Example 67A was dissolved in 0.35 ml of DMF, and 449 mg (6.9 mmol) of sodium azide were added. The mixture was stirred at 80° C. for 2.5 h. Another 0.35 ml of DMF was added, and the reaction mixture was stirred at 80° C. for 3 h. Water was added and the reaction mixture was extracted three times with ethyl acetate. The combined organic phases were dried over sodium sulphate and filtered, and the filtrate was concentrated. Water/TFA was added to the residue, and the solid was filtered off and then purified by thick-layer chromatography (mobile phase: dichloromethane/ethyl acetate=2.5/1). This gave 38 mg (over two steps: 21% of theory; purity about 85%) of the target compound.

LC-MS (Method 1): $R_t$=0.85 min
MS (ESpos): m/z=440 (M+H)$^+$

Example 69A rac-Benzyl (1-cyano-3-hydroxypropan-2-yl)carbamate

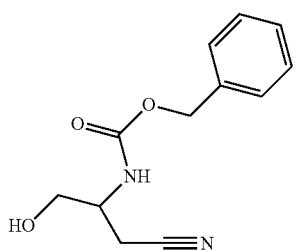 [SMILES: N#CCC(CO)NC(=O)OCc1ccccc1]

1.00 g (7.32 mmol) of rac-3-amino-4-hydroxybutanonitrile hydrochloride was dissolved in 105 ml of 1,4-dioxane, and aqueous potassium carbonate solution (about 2.5 g of potassium carbonate in 2.5 ml of water) and then 1.75 g (10.25 mmol) of benzyl carbonochloridate were added at RT. The reaction mixture was stirred at room temperature overnight. The mixture was concentrated, and the residue was taken up in ethyl acetate and washed once with water. The organic phase was dried over sodium sulphate, filtered and concentrated. The crude product was purified by silica gel chromatography (mobile phase: dichloromethane 100%; dichloromethane/ethyl acetate=2/1). This gave 1.5 g of the target compound (87% of theory).

LC-MS (Method 17): $R_t$=1.56 min
MS (ESpos): m/z=235 (M+H)$^+$
$^1$H-NMR (400 MHz, DMSO-d$_6$): δ=2.55-2.63 (m, 1H), 2.70-2.80 (m, 1H), 3.28-3.36 (m, 1H; superposed by water signal), 3.38-3.47 (m, 1H), 3.69-3.70 (m, 1H), 4.96 (t, 1H), 5.07 (s, 2H), 7.28-7.40 (m, 5H), 7.48 (d, 1H).

Example 70A rac-Benzyl (1-chloro-3-cyanopropan-2-yl)carbamate

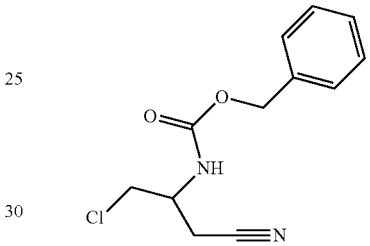

450 mg (1.86 mmol) of rac-benzyl (1-cyano-3-hydroxypropan-2-yl)carbamate were initially charged in 6.8 ml of abs. dichloromethane, and 0.27 ml (3.73 mmol) of thionyl chloride was added at room temperature. The solution was stirred at room temperature for 2 h. 0.27 ml (3.73 mmol) of thionyl chloride was then added, and the reaction solution was stirred overnight. Another 0.27 ml (3.73 mmol) of thionyl chloride was added, and the mixture was stirred for 30 min. The reaction solution was concentrated, concentrated twice with dichloromethane, dried under high vacuum and used without further purification for the subsequent step.

Example 71A rac-Benzyl (1-azido-3-cyanopropan-2-yl)carbamate

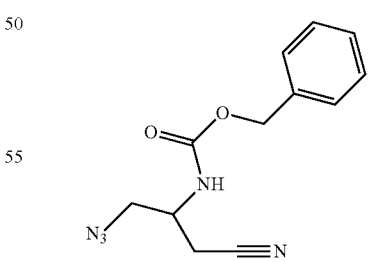

rac-Benzyl (1-chloro-3-cyanopropan-2-yl)carbamate (crude product from Example 70A) was dissolved in 9.2 ml of 1,4-DMF, and 262 mg (4.04 mmol) of sodium azide were added. The mixture was stirred at RT for 1 h, at 50° C. for 2 h and then at 80° C. for 6 h. The reaction mixture was diluted with dichloromethane and washed twice with water. The aqueous phase was extracted once with dichloromethane. The combined organic phases were dried over sodium sulphate, filtered, concentrated and dried under high vacuum. The residue was purified by preparative HPLC (RP18 column, mobile phase: acetonitrile/water gradient with addition of 0.1% TFA). The product fractions were combined, concentrated to half their original volume (bath temperature: 30° C.) and then lyophilized. This gave 117 mg of the target compound (22% of theory over 2 steps; purity about 91%).

LC-MS (Method 17): $R_t$=1.91 min
MS (ESpos): m/z=260 (M+H)$^+$
$^1$H-NMR (400 MHz, DMSO-$d_6$): δ=2.60-2.70 (m, 1H), 2.71-2.81 (m, 1H), 3.33-3.46 (m, 2H), 3.88-3.99 (m, 1H), 5.09 (s, 2H), 7.26-7.39 (m, 5H), 7.78 (d, 1H).

Example 72A rac-Benzyl (1-amino-3-cyanopropan-2-yl)carbamate hydrochloride

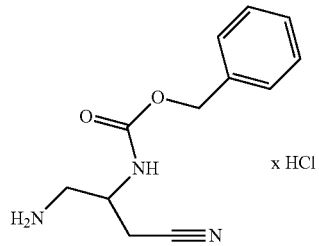 [SMILES: N#CCC(CN)NC(=O)OCc1ccccc1]

117 mg (0.41 mmol; purity about 91%) of rac-benzyl (1-azido-3-cyanopropan-2-yl)carbamate from Example 71A were initially charged in 10.5 ml of ethanol, and 9 mg of palladium on activated carbon (10%) were added. The reaction mixture was hydrogenated at RT under standard pressure for 1 h and then filtered through a Millipore filter. 0.41 ml of 1 N aqueous hydrochloric acid was added and the reaction solution was concentrated and dried under high vacuum. This gave 105 mg of the target compound (95% of theory).

LC-MS (Method 17): $R_t$=1.24 min
MS (ESpos): m/z=234 (M−HCl+H)$^+$

Example 73A rac-Benzyl {1-cyano-3-[({8-[(2,6-difluorobenzyl)oxy]-2,6-dimethylimidazo[1,2-a]pyridin-3-yl}carbonyl)amino]propan-2-yl}carbamate trifluoroacetate

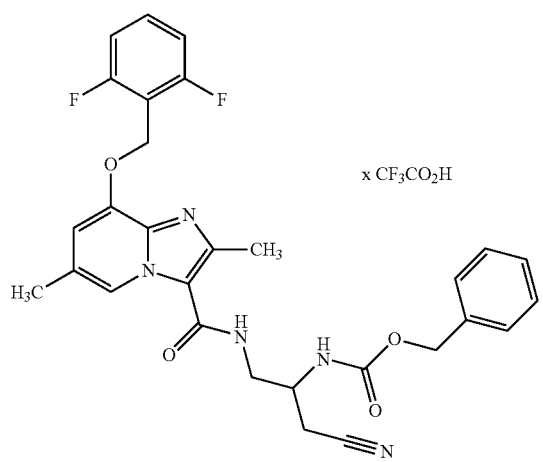 [SMILES: Cc1cc(OCc2c(F)cccc2F)c2nc(C)c(C(=O)NCC(CC#N)NC(=O)OCc3ccccc3)n2c1]

148 mg (0.39 mmol) of HATU and 0.26 ml (1.50 mmol) of N,N-diisopropylethylamine were added to 100 mg (0.30 mmol) of 8-[(2,6-difluorobenzyl)oxy]-2,6-dimethylimidazo[1,2-a]pyridine-3-carboxylic acid from Example 16A in 1.0 ml of DMF. The reaction mixture was stirred at RT for 20 min, 105 mg (0.39 mmol) of rac-benzyl (1-amino-3-cyanopropan-2-yl)carbamate hydrochloride from Example 72A were then added and the mixture was stirred at RT overnight. Acetonitrile, water and TFA were added and the reaction solution was purified by preparative HPLC (RP18 column, mobile phase: acetonitrile/water gradient with addition of 0.1% TFA). This gave 144 mg of the target compound (69% of theory; purity about 95%).

LC-MS (Method 1): $R_t$=0.88 min
MS (ESpos): m/z=548 (M−TFA+H)$^+$

Example 74A rac-Benzyl (4-cyano-1-hydroxybutan-2-yl)carbamate

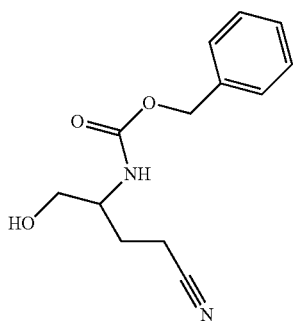 [SMILES: N#CCCC(CO)NC(=O)OCc1ccccc1]

The target compound can be prepared by reacting rac-methyl N-[(benzyloxy)carbonyl]-5-nitrilonorvalinate [which can be prepared analogously to Stapon, A. et al. Journal of the American Chemical Society 2003, 125, 8486-8493; Boger, D. L. et al. 1999, 121, 6197-6205; U.S. Pat. No. 5,747,499 (Example 10); U.S. Pat. No. 5,789,417 (Example 12) from racemic starting material] with sodium borohydride (NaBH$_4$) in THF (or with other reducing agents such as lithium borohydride or lithium aluminium hydride) at room temperature according to methods known from the literature.

Example 75A rac-Benzyl (5-cyano-1-hydroxypentan-2-yl)carbamate

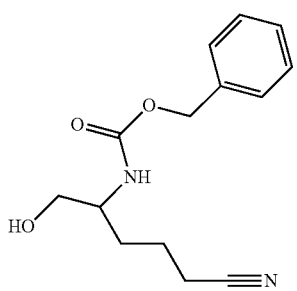 [SMILES: N#CCCCC(CO)NC(=O)OCc1ccccc1]

The target compound can be prepared analogously to Scott, A. I. et al. Synthetic Communications 1980, 10, 127-132 and Huang, S.-B. et al. Synthetic Communications 1989, 19, 3485-3496 from racemic starting material.

Example 76A rac-Benzyl [4-cyano-1-(1,3-dioxo-1,3-dihydro-2H-isoindol-2-yl)butan-2-yl]carbamate

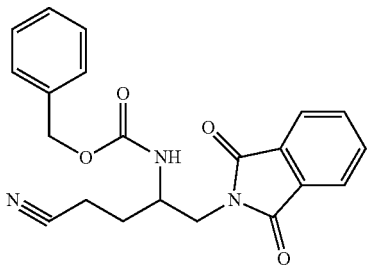 [SMILES: N#CCCC(CN1C(=O)c2ccccc2C1=O)NC(=O)OCc1ccccc1]

178 mg (1.21 mmol) of 1H-isoindole-1,3(2H)-dione and 475 mg (1.81 mmol) of triphenylphosphine were added to 300 mg (1.21 mmol) of rac-benzyl (4-cyano-1-hydroxybutan-2-yl)carbamate in 6 ml of THF. 0.496 ml (1.81 mmol, purity 94%) of diisopropyl azodicarboxylate were then added dropwise, and the mixture was stirred at RT for 30 minutes. The reaction mixture was concentrated and the residue was purified by silica gel chromatography (mobile phase: cyclohexane/ethyl acetate gradient 7/3 to 2/1). This gave 398 mg (86% of theory) of the target compound.

LC-MS (Method 1): $R_t$=0.87 min
MS (ESneg): m/z=376 (M−H)⁻

Example 77A rac-Benzyl [5-cyano-1-(1,3-dioxo-1,3-dihydro-2H-isoindol-2-yl)pentan-2-yl]carbamate

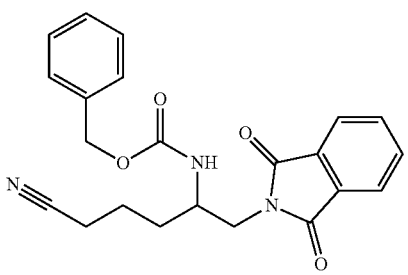 [SMILES: N#CCCCC(CN1C(=O)c2ccccc2C1=O)NC(=O)OCc1ccccc1]

2.24 g (15.2 mmol) of 1H-isoindole-1,3(2H)-dione and 6.00 g (22.9 mmol) of triphenylphosphine were added to 4.00 g (15.2 mmol) of rac-benzyl (5-cyano-1-hydroxypentan-2-yl)carbamate in 76 ml of THF. 6.26 ml (22.9 mmol, purity 94%) of diisopropyl azodicarboxylate were then added dropwise, and the mixture was stirred at RT for 1 hour. The reaction mixture was concentrated and the residue was purified by silica gel chromatography (mobile phase: cyclohexane/ethyl acetate gradient 2/1 to 1/1). This gave 1.40 g (17% of theory, purity 72%) and 9.68 g (49% of theory, purity 30%) of the target compound.

LC-MS (Method 26): $R_t$=2.78 min
MS (ESpos): m/z=392 (M+H)⁺

Example 78A rac-Benzyl (1-amino-4-cyanobutan-2-yl)carbamate trifluoroacetate

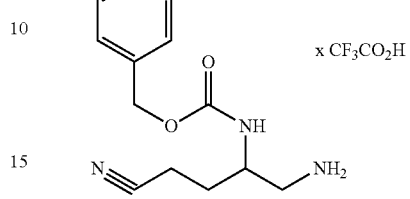

397 mg (1.05 mmol) of rac-benzyl [4-cyano-1-(1,3-dioxo-1,3-dihydro-2H-isoindol-2-yl)butan-2-yl]carbamate from Example 76A were dissolved in 3.63 ml (42.0 mmol) of methanamine (40% in water), and the mixture was stirred at 40° C. for 2.5 hours. The reaction solution was concentrated and distilled with methanol three times. The residue was purified by silica gel chromatography (mobile phase: dichloromethane/methanol gradient 30/1 to 10/1; subsequent rinsing of the column with ethyl acetate/methanol 2/1). The product-containing fractions were combined and concentrated. Acetonitrile, water and TFA were added to the residue and the product was purified by preparative HPLC (RP18 column, mobile phase: acetonitrile/water gradient with addition of 0.1% TFA). This gave 136 mg (35% of theory) of the target compound.

LC-MS (Method 26): $R_t$=0.84 min
MS (ESpos): m/z=248 (M-TFA+H)⁺

Example 79A rac-Benzyl (1-amino-5-cyanopentan-2-yl)carbamate trifluoroacetate

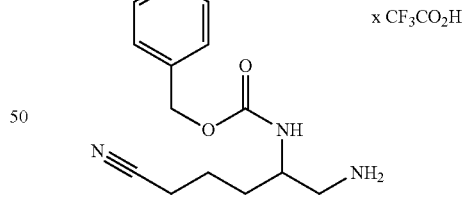

1.40 g (2.58 mmol, purity 72%) of rac-benzyl [5-cyano-1-(1,3-dioxo-1,3-dihydro-2H-isoindol-2-yl)pentan-2-yl]carbamate from Example 77A were dissolved in 11.1 ml (129 mmol) of methanamine (40% in water), and the mixture was stirred at 60° C. for two hours. The reaction solution was concentrated and distilled with methanol three times. The residue was purified by preparative HPLC (RP18 column, mobile phase: acetonitrile/water gradient with addition of 0.1% TFA). This gave 502 mg (52% of theory) of the target compound.

LC-MS (Method 1): $R_t$=0.47 min
MS (ESpos): m/z=262 (M-TFA+H)⁺

Example 80A rac-Benzyl {4-cyano-1-[({8-[(2,6-difluorobenzyl)oxy]-2,6-dimethylimidazo[1,2-a]pyridin-3-yl}carbonyl)amino]butan-2-yl}carbamate

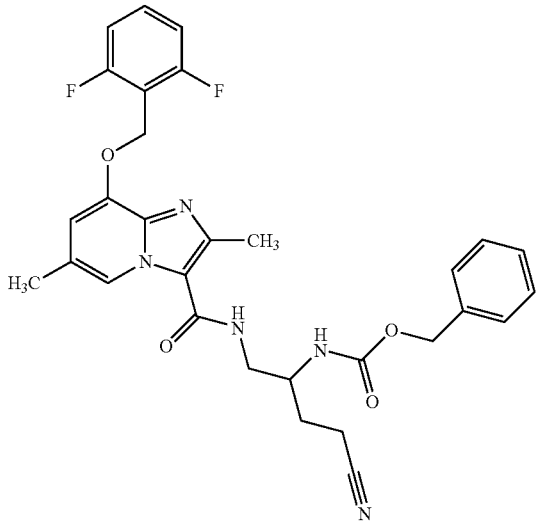 [SMILES: Cc1cc(OCc2c(F)cccc2F)c2nc(C)c(C(=O)NCC(CCC#N)NC(=O)OCc3ccccc3)n2c1]

74 mg (0.19 mmol) of HATU and 0.13 ml (0.75 mmol) of N,N-diisopropylethylamine were added to 50 mg (0.15 mmol) of 8-[(2,6-difluorobenzyl)oxy]-2,6-dimethylimidazo carboxylic acid from Example 16A in 0.5 ml of DMF. The reaction mixture was stirred at RT for 20 min, 70 mg (0.19 mmol) of rac-benzyl (1-amino-4-cyanobutan-2-yl)carbamate trifluoroacetate from Example 78A were then added and the mixture was stirred at RT for 1.5 hours. Water was added to the reaction mixture, and the solid formed was filtered off and dried under high vacuum. This gave 78 mg of the target compound (90% of theory; purity 96%).

LC-MS (Method 1): $R_t$=0.84 min
MS (ESpos): m/z=562 (M+H)$^+$

Example 81A rac-Benzyl {5-cyano-1-[({8-[(2,6-difluorobenzyl)oxy]-2,6-dimethylimidazo[1,2-a]pyridin-3-yl}carbonyl)amino]pentan-2-yl}carbamate trifluoroacetate

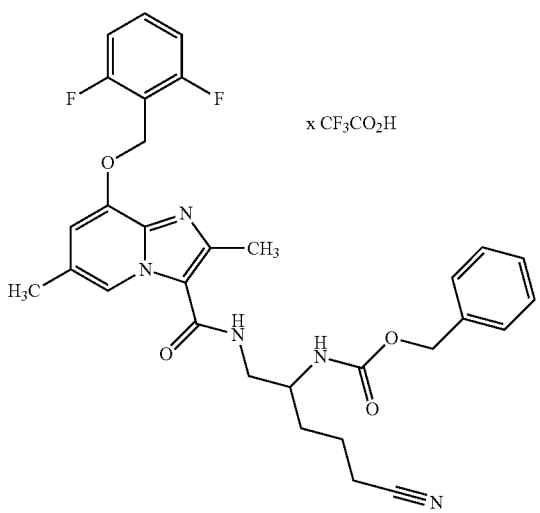 [SMILES: Cc1cc(OCc2c(F)cccc2F)c2nc(C)c(C(=O)NCC(CCCC#N)NC(=O)OCc3ccccc3)n2c1]

240 mg (0.63 mmol) of HATU and 0.52 ml (3.01 mmol) of N,N-diisopropylethylamine were added to 200 mg (0.60 mmol) of 8-[(2,6-difluorobenzyl)oxy]-2,6-dimethylimidazo[1,2-a]pyridine-3-carboxylic acid from Example 16A in 2.0 ml of DMF. The reaction mixture was stirred at RT for 10 min, 248 mg (0.66 mmol) of rac-benzyl (1-amino-5-cyanopentan-2-yl)carbamate trifluoroacetate from Example 79A were then added and the mixture was stirred at RT for 2 hours. Acetonitrile, water and TFA were added and the reaction solution was purified by preparative HPLC (RP18 column, mobile phase: acetonitrile/water gradient with addition of 0.1% TFA). This gave 353 mg of the target compound (81% of theory, purity 95%).

LC-MS (Method 27): $R_t$=1.56 min
MS (ESpos): m/z=576 (M-TFA+H)$^+$

WORKING EXAMPLES

Example 1 rac-N-(1-Cyanoethyl)-8-[(2,6-difluorobenzyl)oxy]-2,6-dimethylimidazo[1,2-a]pyridine-3-carboxamide

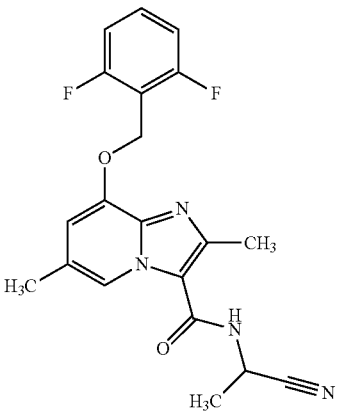 [SMILES: Cc1cc(OCc2c(F)cccc2F)c2nc(C)c(C(=O)NC(C)C#N)n2c1]

119 mg (0.31 mmol) of HATU and 0.29 ml (1.69 mmol) of N,N-diisopropylethylamine were added to 80 mg (0.24 mmol) of 8-[(2,6-difluorobenzyl)oxy]-2,6-dimethylimidazo[1,2-a]pyridine-3-carboxylic acid from Example 16A in 0.8 ml of DMF. The reaction mixture was stirred at RT for 20 min, 33.3 mg (0.31 mmol) of rac-2-aminopropanonitrile hydrochloride were then added and the mixture was stirred at RT for 1 hour. The reaction solution was admixed with water and the solid that formed was stirred at room temperature for about 30 min. Subsequently, the solid was filtered off, washed well with water and dried under high vacuum. This gave 76 mg of the target compound (79% of theory).

LC-MS (Method 1): $R_t$=0.83 min
MS (ESpos): m/z=385 (M+H)$^+$
$^1$H-NMR (400 MHz, DMSO-$d_6$): δ=1.57 (d, 3H), 2.33 (s, 3H), 4.98 (q, 1H), 5.29 (s, 2H), 6.98 (s, 1H), 7.19-7.29 (m, 2H), 7.54-7.65 (m, 1H), 8.47-8.56 (m, 2H), [further signal under solvent peak].

In analogy to Example 1, the example compounds shown in Table 1 were prepared by reacting the carboxylic acid from Example 16A with the appropriate amines which are commercially available or known from the literature (1.1-8 equivalents), HATU (1.1-2.5 equivalents) and N,N-diisopropylethylamine (2.5-8 equivalents) in DMF under the reaction conditions described (reaction time: 0.5-24 h; temperature: RT or 60° C.).

Illustrative workup of the reaction mixture:

The reaction solution was admixed with water and the solid that formed was stirred at room temperature for about 30 min. Subsequently, the solid was filtered off, washed well with water and dried under high vacuum.

Alternatively, the reaction mixture was diluted with water/TFA and purified by preparative HPLC (RP18 column, mobile phase: acetonitrile/water gradient with addition of 0.1% TFA or 0.05% formic acid). Additionally or alternatively, the crude product was optionally purified by silica gel chromatography (mobile phase: dichloromethane/methanol or cyclohexane/ethyl acetate) and/or thick-layer chromatography (mobile phase: dichloromethane/methanol).

The product-containing fractions from the preparative HPLC were concentrated and the residue was taken up in dichloromethane and washed with saturated aqueous sodium bicarbonate solution. The aqueous phase was extracted twice with dichloromethane, and the combined organic phases were dried over sodium sulphate, filtered, concentrated and lyophilized.

TABLE 1

| Example | IUPAC name/structure (Yield) | Analytical data |
|---|---|---|
| 2 | N-(cyanomethyl)-8-[(2,6-difluorobenzyl)oxy]-2,6-dimethylimidazo[1,2-a]pyridine-3-carboxamide 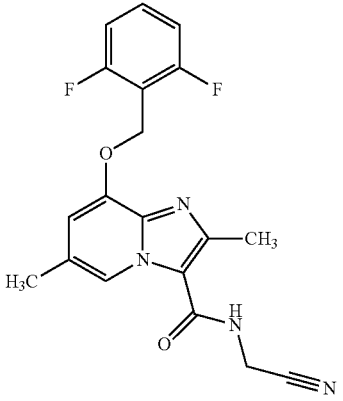 [SMILES: Cc1cc(OCc2c(F)cccc2F)c2nc(C)c(C(=O)NCC#N)n2c1] (72% of theory) | LC-MS (Method 1): $R_t$ = 0.83 min<br>MS (ESpos): m/z = 371 (M + H)$^+$<br>$^1$H-NMR (400 MHz, DMSO-$d_6$) δ = 2.34 (s, 3H), 2.50 (br. s., 3H), 4.33 (s, 2H), 5.29 (s, 2H), 6.99 (s, 1H), 7.18-7.29 (m, 2H), 7.54-7.65 (m, 1H), 8.35 (br. s., 1H), 8.60 (s, 1H). |
| 3 | N-(2-cyanopropan-2-yl)-8-[(2,6-difluorobenzyl)oxy]-2,6-dimethylimidazo[1,2-a]pyridine-3-carboxamide 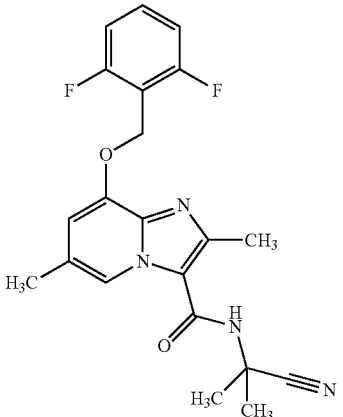 (5% of theory) | LC-MS (Method 1): $R_t$ = 0.88 min<br>MS (ESpos): m/z = 399 (M + H)$^+$<br>$^1$H-NMR (400 MHz, DMSO-$d_6$) δ = 1.72 (s, 6H), 2.34 (s, 3H), 2.49 (br. s., 3H), 5.30 (s, 2H), 6.98 (s, 1H), 7.20-7.28 (m, 2H), 7.55-7.65 (m, 1H), 8.21 (s, 1H), 8.46 (s, 1H). |

TABLE 1-continued

| Example | IUPAC name/structure (Yield) | Analytical data |
|---|---|---|
| 4 | N-(1-cyanocyclopropyl)-8-[(2,6-difluorobenzyl)oxy]-2,6-dimethylimidazo[1,2-a]pyridine-3-carboxamide<br>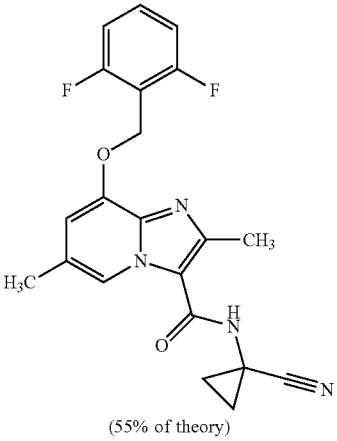<br>(55% of theory) | LC-MS (Method 1): $R_t$ = 0.83 min<br>MS (ESpos): m/z = 397 (M + H)$^+$ |
| 5 | N-(1-cyanocyclobutyl)-8-[(2,6-difluorobenzyl)oxy]-2,6-dimethylimidazo[1,2-a]pyridine-3-carboxamide<br>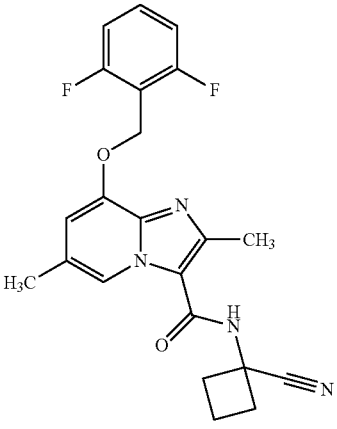 [SMILES: Cc1cc(OCc2c(F)cccc2F)c2nc(C)c(C(=O)NC3(C#N)CCC3)n2c1]<br>(11% of theory) | LC-MS (Method 1): $R_t$ = 0.92 min<br>MS (ESpos): m/z = 411 (M + H)$^+$<br>$^1$H-NMR (400 MHz, DMSO-d$_6$) δ = 2.02-2.13 (m, 2H), 2.34 (s, 3H), 2.41-2.48 (m, 2H), 2.64-2.75 (m, 2H), 5.30 (s, 2H), 7.00 (s, 1H), 7.19-7.29 (m, 2H), 7.54-7.65 (m, 1H), 8.52 (s, 1H), 8.64 (s, 1H), [further signal under solvent peak]. |
| 6 | rac-N-(1-cyano-1-cyclopropylethyl)-8-[(2,6-difluorobenzyl)oxy]-2,6-dimethylimidazo[1,2-a]pyridine-3-carboxamide$^{1)}$<br>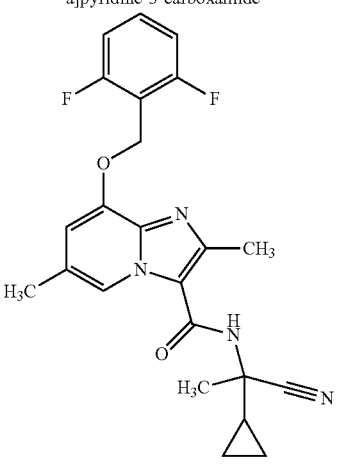<br>(3% of theory) | LC-MS (Method 1): $R_t$ = 0.95 min<br>MS (ESpos): m/z = 425 (M + H)$^+$<br>$^1$H-NMR (400 MHz, DMSO-d$_6$) δ = 0.51-0.72 (m, 4H), 1.52-1.63 (m, 1H), 1.68 (s, 3H), 2.33 (s, 3H), 5.31 (s, 2H), 6.97 (s, 1H), 7.19-7.28 (m, 2H), 7.54-7.65 (m, 1H), 8.24 (s, 1H), 8.42 (s, 1H), [further signal under solvent peak]. |

TABLE 1-continued

| Example | IUPAC name/structure (Yield) | Analytical data |
|---|---|---|
| 7 | rac-N-(2-cyano-1-methoxypropan-2-yl)-8-[(2,6-difluorobenzyl)oxy]-2,6-dimethylimidazo[1,2-a]pyridine-3-carboxamide[1]<br>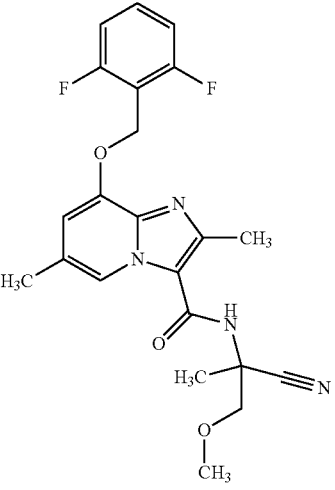 [SMILES: COCC(C)(C#N)NC(=O)c1c(C)nc2c(OCc3c(F)cccc3F)cc(C)cn12]<br>(7% of theory) | LC-MS (Method 1): $R_t$ = 0.89 min<br>MS (ESpos): m/z = 429 (M + H)$^+$<br>$^1$H NMR (400 MHz, DMSO-d$_6$) δ = 1.70 (s, 3H), 2.34 (s, 3H), 2.48 (s, 3H), 3.41 (s, 3H), 3.63 (d, 1H), 3.87 (d, 1H), 5.30 (s, 2H), 6.99 (s, 1H), 7.20-7.29 (m, 2H), 7.53-7.66 (m, 1H), 8.16 (s, 1H), 8.44 (s, 1H). |
| 8 | rac-N-[(4-chlorophenyl)(cyano)methyl]-8-[(2,6-difluorobenzyl)oxy]-2,6-dimethylimidazo[1,2-a]pyridine-3-carboxamide<br>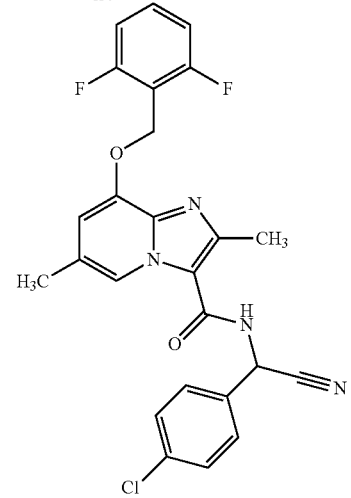 [SMILES: Cc1cc(OCc2c(F)cccc2F)c2nc(C)c(C(=O)NC(C#N)c3ccc(Cl)cc3)n2c1]<br>(39% of theory) | LC-MS (Method 1): $R_t$ = 1.12 min<br>MS (ESpos): m/z = 481 (M + H)$^+$<br>$^1$H NMR (400 MHz, DMSO-d$_6$) δ = 2.33 (s, 3H), 5.30 (s, 2H), 6.39 (d, 1H), 7.00 (s, 1H), 7.19-7.29 (m, 2H), 7.53-7.66 (m, 5H), 8.48 (s, 1H), 9.06 (d, 1H), [further signal under solvent peak]. |
| 9 | N-(2-cyanoethyl)-8-[(2,6-difluorobenzyl)oxy]-2,6-dimethylimidazo[1,2-a]pyridine-3-carboxamide<br>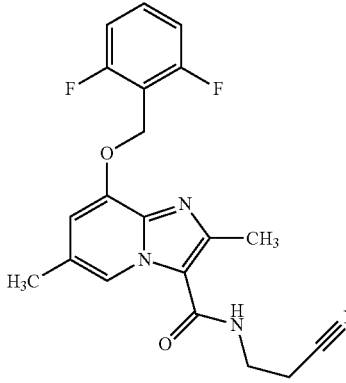<br>(64% of theory) | LC-MS (Method 1): $R_t$ = 0.78 min<br>MS (ESpos): m/z = 385 (M + H)$^+$<br>$^1$H NMR (400 MHz, DMSO-d$_6$) δ = 2.31 (s, 3H), 2.82 (t, 2H), 3.55 (q, 2H), 5.29 (s, 2H), 6.94 (s, 1H), 7.18-7.30 (m, 2H), 7.53-7.65 (m, 1H), 8.14 (br. t, 1H), 8.47 (s, 1H), [further signal under solvent peak]. |

TABLE 1-continued

| Example | IUPAC name/structure (Yield) | Analytical data |
|---|---|---|
| 10 | N-(5-cyanopentyl)-8-[(2,6-difluorobenzyl)oxy]-2,6-dimethylimidazo[1,2-a]pyridine-3-carboxamide<br><br>(89% of theory) | LC-MS (Method 1): $R_t$ = 0.81 min<br>MS (ESpos): m/z = 427 (M + H)$^+$<br>$^1$H NMR (400 MHz, DMSO-$d_6$) δ = 1.38-1.49 (m, 2H), 1.54-1.65 (m, 4H), 2.30 (s, 3H), 3.25-3.38 (t, 2H; superposed by solvent peak), 5.28 (s, 2H), 6.90 (s, 1H), 7.18-7.28 (m, 2H), 7.54-7.63 (m, 1H), 7.80-7.90 (m, 1H), 8.43 (s, 1H), [further signal under solvent peak]. |
| 11 | N-(2-cyanocyclohexyl)-8-[(2,6-difluorobenzyl)oxy]-2,6-dimethylimidazo[1,2-a]pyridine-3-carboxamide (mixture of stereoisomers)<br><br>(77% of theory) | LC-MS (Method 1): $R_t$ = 0.86 and 0.89 min<br>MS (ESpos): m/z = 439 (M + H)$^+$ |
| 12 | N-[(4-cyanocyclohexyl)methyl]-8-[(2,6-difluorobenzyl)oxy]-2,6-dimethylimidazo[1,2-a]pyridine-3-carboxamide (cis/trans mixture)<br><br>(86% of theory) | LC-MS (Method 1): $R_t$ = 0.85 and 0.86 min<br>MS (ESpos): m/z = 453 (M + H)$^+$ |

TABLE 1-continued

| Example | IUPAC name/structure (Yield) | Analytical data |
|---|---|---|
| 13 | rac-N-(1-cyanobutan-2-yl)-8-[(2,6-difluorobenzyl)oxy]-2,6-dimethylimidazo[1,2-a]pyridine-3-carboxamide<br>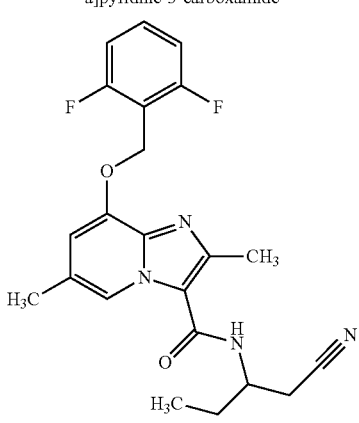<br>(72% of theory) | LC-MS (Method 1): $R_t$ = 0.82 min<br>MS (ESpos): m/z = 413 (M + H)$^+$<br>$^1$H NMR (500 MHz, DMSO-d$_6$) δ = 0.93 (t, 3H), 1.60-1.69 (m, 2H), 2.30 (s, 3H), 2.74-2.83 (m, 1H), 2.84-2.92 (m, 1H), 4.10-4.20 (m, 1H), 5.29 (s, 2H), 6.92 (s, 1H), 7.19-7.27 (m, 2H), 7.55-7.63 (m, 1H), 7.99 (d, 1H), 8.33 (s, 1H) [further signal under solvent peak]. |
| 14 | rac-N-(1-cyano-3-hydroxypropan-2-yl)-8-[(2,6-difluorobenzyl)oxy]-2,6-dimethylimidazo[1,2-a]pyridine-3-carboxamide<br>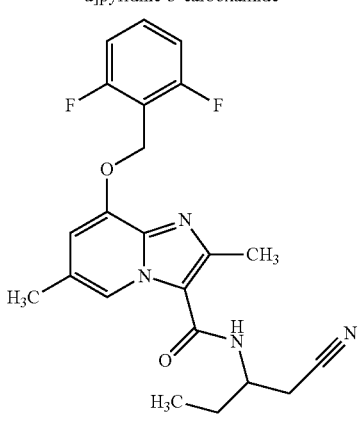<br>(79% of theory) | LC-MS (Method 1): $R_t$ = 0.67 min<br>MS (ESpos): m/z = 415 (M + H)$^+$<br>$^1$H NMR (400 MHz, DMSO-d$_6$) δ = 2.32 (s, 3H), 2.74-2.83 (m, 1H), 2.86-2.94 (m, 1H), 3.43-3.54 (m, 1H), 3.56-3.63 (m, 1H), 4.20-4.32 (m, 1H), 5.09 (br. s, 1H), 5.29 (s, 2H), 6.98 (br. s, 1H), 7.18-7.28 (m, 2H), 7.53-7.63 (m, 1H), 7.93 (br. s, 1H), 8.39 (s, 1H), [further signal under solvent peak]. |

$^{I)}$reaction temperature: 60° C.

Example 15 ent-N-(1-Cyanoethyl)-8-[(2,6-difluorobenzyl)oxy]-2,6-dimethylimidazo[1,2-a]pyridine-3-carboxamide (Enantiomer A)

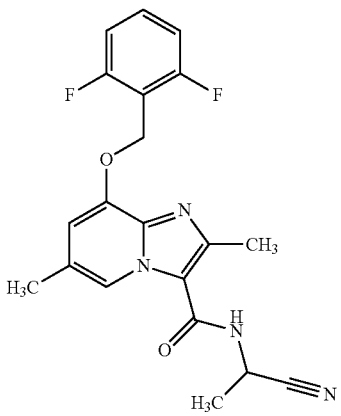 [SMILES: Cc1cc(OCc2c(F)cccc2F)c2nc(C)c(C(=O)NC(C)C#N)n2c1]

155 mg of Example 1 were separated into the enantiomers on a chiral phase [column: Daicel Chiralpak AD-H, 5 µm, 250×20 mm, mobile phase: 50% isohexane, 50% ethanol; flow rate: 20 ml/min; 20° C., detection: 220 nm].

The product was purified again by preparative HPLC (RP18 column; mobile phase: acetonitrile/water gradient with addition of 0.1% TFA). The product-containing fractions were concentrated, and the residue was taken up in dichloromethane and washed with saturated aqueous sodium bicarbonate solution. The aqueous phase was extracted twice with dichloromethane, and the combined organic phases were dried over sodium sulphate, filtered, concentrated and lyophilized.

Yield: enantiomer A: 17 mg (99% ee)

enantiomer A: $R_t$=7.13 min [Daicel Chiralpak AD-H, 5 µm, 250×4.6 mm, mobile phase: 50% isohexane, 50% isopropanol; flow rate: 1 ml/min; 30° C., detection: 220 nm].

Example 16 ent-N-(1-Cyanoethyl)-8-[(2,6-difluorobenzyl)oxy]-2,6-dimethylimidazo[1,2-a]pyridine-3-carboxamide (Enantiomer B)

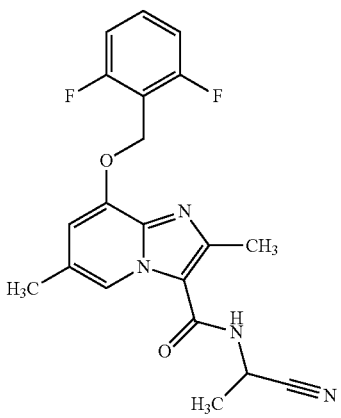 [SMILES: Cc1cc(OCc2c(F)cccc2F)c2nc(C)c(C(=O)NC(C)C#N)n2c1]

155 mg of Example 1 were separated into the enantiomers on a chiral phase [column: Daicel Chiralpak AD-H, 5 µm, 250×20 mm, mobile phase: 50% isohexane, 50% ethanol; flow rate: 20 ml/min; 20° C., detection: 220 nm].

The product was purified again by preparative HPLC (RP18 column; mobile phase: acetonitrile/water gradient with addition of 0.1% TFA). The product-containing fractions were concentrated, and the residue was taken up in dichloromethane and washed with saturated aqueous sodium bicarbonate solution. The aqueous phase was extracted twice with dichloromethane, and the combined organic phases were dried over sodium sulphate, filtered, concentrated and lyophilized.

Yield: enantiomer B: 20 mg (89% ee)

enantiomer B: $R_t$=11.08 min [Daicel Chiralpak AD-H, 5 µm, 250×4.6 mm, mobile phase: 50% isohexane, 50% isopropanol; flow rate: 1 ml/min; 30° C., detection: 220 nm].

Example 17 rac-N-[(4-Chlorophenyl)(cyano)methyl]-2,6-dimethyl-8-[(2,3,6-trifluorobenzyl)oxy]imidazo[1,2-a]pyridine-3-carboxamide

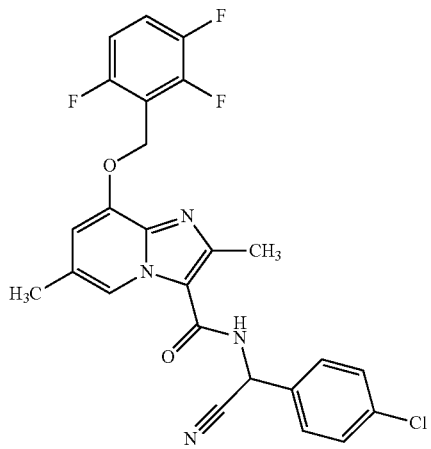 [SMILES: Cc1cc(OCc2c(F)ccc(F)c2F)c2nc(C)c(C(=O)NC(C#N)c3ccc(Cl)cc3)n2c1]

35 mg (0.10 mmol) of 2,6-dimethyl-8-[(2,3,6-trifluorobenzyl)oxy]imidazo[1,2-a]pyridine-3-carboxylic acid from Example 22A were initially charged in a 96-well deep-well multititre plate. A solution of 17 mg (0.10 mmol) of rac-amino(4-chlorophenyl)acetonitrile [CAS-RN-No.: 49704-71-4] in 0.4 ml of DMF and a solution of 45.6 mg (0.12 mol) of HATU in 0.4 ml of DMF were added successively. After adding 20.2 mg (0.20 mmol) of 4-methylmorpholine, the mixture was shaken at RT overnight. Then the mixture was filtered and the target compound was isolated from the filtrate by preparative LC-MS (Method 11). The product-containing fractions were concentrated under reduced pressure using a centrifugal dryer. The residue of each product fraction was dissolved in 0.6 ml of DMSO. These were combined and finally freed of the solvent in a centrifugal dryer. This gave 5 mg (10% of theory) of the target compound.

LC-MS (Method 12): $R_t$=1.11 min

MS (ESpos): m/z=499 (M+H)$^+$

In analogy to Example 17, the example compounds shown in Table 2 were prepared by reacting the appropriate carboxylic acids with rac-amino(4-chlorophenyl)acetonitrile [CAS-RN-No.: 49704-71-4], under the conditions described:

TABLE 2

| Example | IUPAC name/structure (Yield) | Analytical data |
|---|---|---|
| 18 | rac-N-[(4-chlorophenyl)(cyano)methyl]-8-[(2,6-difluorobenzyl)oxy]imidazo[1,2-a]pyridine-3-carboxamide<br>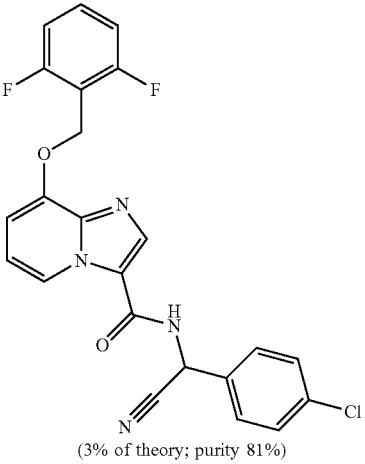<br>(3% of theory; purity 81%) | LC-MS (Method 12): $R_t$ = 1.15 min<br>MS (ESpos): m/z = 453 (M + H)$^+$ |
| 19 | rac-N-[(4-chlorophenyl)(cyano)methyl]-8-[(3-fluoropyridin-2-yl)methoxy]-2,6-dimethylimidazo[1,2-a]pyridine-3-carboxamide<br>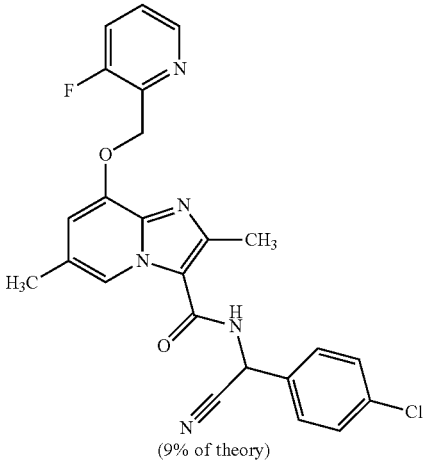<br>(9% of theory) | LC-MS (Method 12): $R_t$ = 0.98 min<br>MS (ESpos): m/z = 464 (M + H)$^+$ |
| 20 | rac-N-[(4-chlorophenyl)(cyano)methyl]-8-(cyclohexylmethoxy)-2-methylimidazo[1,2-a]pyridine-3-carboxamide<br>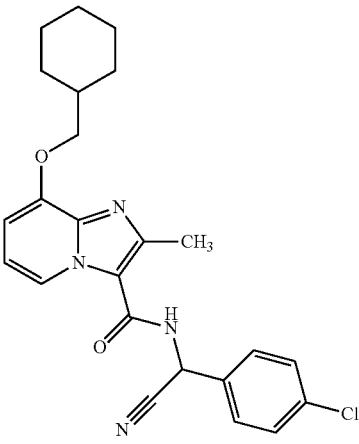 [SMILES: Cc1nc2c(OCC3CCCCC3)cccn2c1C(=O)NC(C#N)c1ccc(Cl)cc1]<br>(13% of theory) | LC-MS (Method 12): $R_t$ = 1.11 min<br>MS (ESpos): m/z = 437 (M + H)$^+$ |

TABLE 2-continued

| Example | IUPAC name/structure (Yield) | Analytical data |
|---|---|---|
| 21 | rac-N-[(4-chlorophenyl)(cyano)methyl]-8-[(3-fluoropyridin-2-yl)methoxy]-2-methylimidazo[1,2-a]pyridine-3-carboxamide 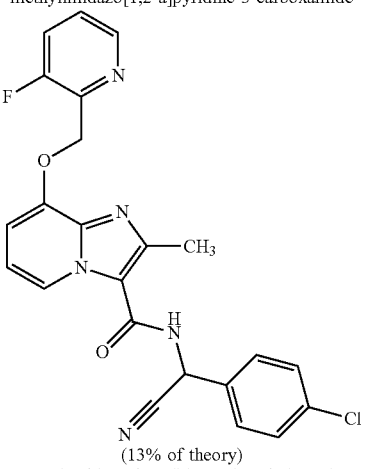 (13% of theory) | LC-MS (Method 12): $R_t$ = 0.98 min<br>MS (ESpos): m/z = 450 (M + H)$^+$ |
| 22 | rac-N-[(4-chlorophenyl)(cyano)methyl]-8-[(2,6-difluoro-3-methoxybenzyl)oxy]-2,6-dimethylimidazo[1,2-a]pyridine-3-carboxamide 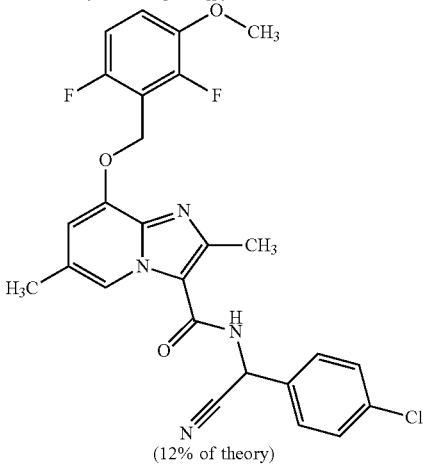 (12% of theory) | LC-MS (Method 12): $R_t$ = 1.10 min<br>MS (ESpos): m/z = 511 (M + H)$^+$ |
| 23 | rac-N-[(4-chlorophenyl)(cyano)methyl]-2,6-dimethyl-8-[4,4,4-trifluoro-3-(trifluoromethyl)butoxy]imidazo[1,2-a]pyridine-3-carboxamide 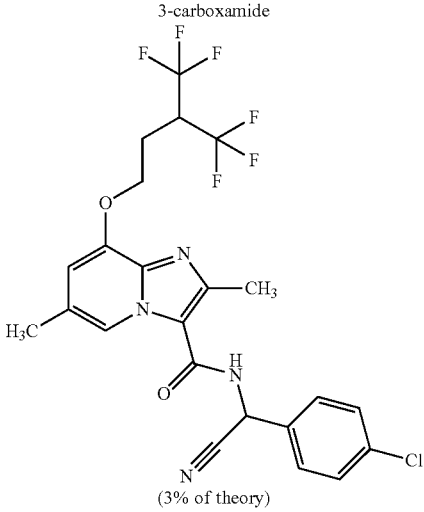 (3% of theory) | LC-MS (Method 12): $R_t$ = 1.13 min<br>MS (ESpos): m/z = 533 (M + H)$^+$ |

TABLE 2-continued

| Example | IUPAC name/structure (Yield) | Analytical data |
|---|---|---|
| 24 | rac-N-[(4-chlorophenyl)(cyano)methyl]-8-[(2,6-difluorobenzyl)oxy]-6-methyl-2-propylimidazo[1,2-a]pyridine-3-carboxamide<br />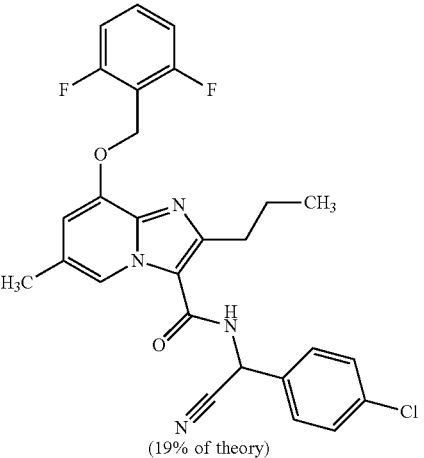<br />(19% of theory) | LC-MS (Method 12): $R_t$ = 1.16 min<br />MS (ESpos): m/z = 509 (M + H)$^+$ |
| 25 | rac-N-[(4-chlorophenyl)(cyano)methyl]-2,6-dimethyl-8-(3-methylbutoxy)imidazo[1,2-a]pyridine-3-carboxamide<br />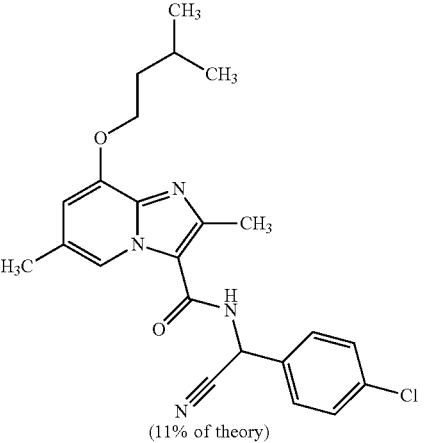<br />(11% of theory) | LC-MS (Method 12): $R_t$ = 1.06 min<br />MS (ESpos): m/z = 425 (M + H)$^+$ |
| 26 | N-[(4-chlorophenyl)(cyano)methyl]-8-[1-(2,6-difluorophenyl)ethoxy]-2,6-dimethylimidazo[1,2-a]pyridine-3-carboxamide (mixture of stereoisomers)[1]<br />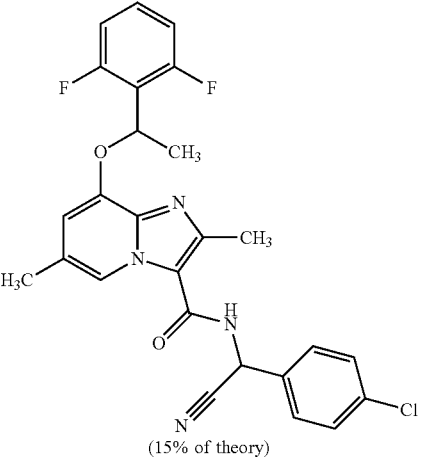<br />(15% of theory) | LC-MS (Method 12): $R_t$ = 1.09 min<br />MS (ESpos): m/z = 495 (M + H)$^+$ |

TABLE 2-continued

| Example | IUPAC name/structure (Yield) | Analytical data |
|---|---|---|
| 27 | rac-N-[(4-chlorophenyl)(cyano)methyl]-8-[(2,6-difluorobenzyl)oxy]-2-ethyl-6-methylimidazo[1,2-a]pyridine-3-carboxamide<br />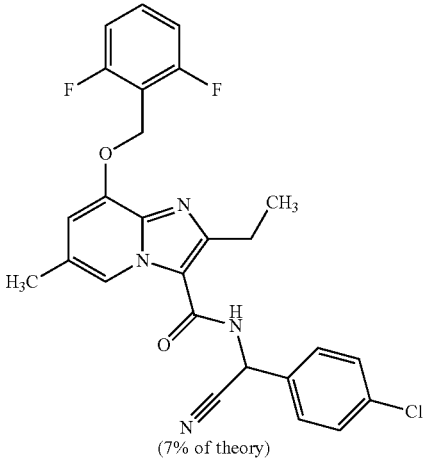<br />(7% of theory) | LC-MS (Method 12): $R_t$ = 1.14 min<br />MS (ESpos): m/z = 495 (M + H)$^+$ |
| 28 | rac-N-[(4-chlorophenyl)(cyano)methyl]-8-[(2,6-difluorobenzyl)oxy]-6-methoxy-2-methylimidazo[1,2-a]pyridine-3-carboxamide<br />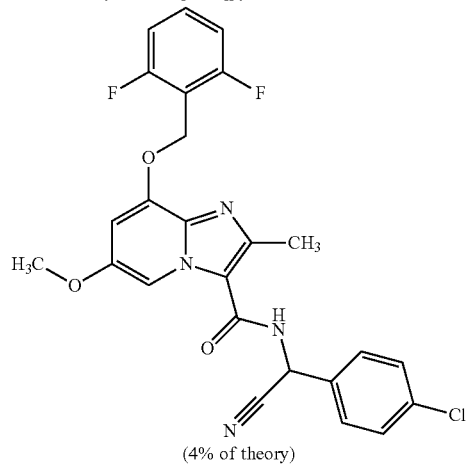<br />(4% of theory) | LC-MS (Method 12): $R_t$ = 1.12 min<br />MS (ESpos): m/z = 497 (M + H)$^+$ |
| 29 | rac-6-chloro-N-[(4-chlorophenyl)(cyano)methyl]-8-[(2,6-difluorobenzyl)oxy]-2-methylimidazo[1,2-a]pyridine-3-carboxamide<br />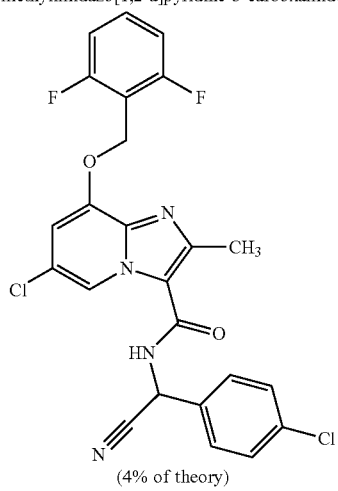<br />(4% of theory) | LC-MS (Method 12): $R_t$ = 1.24 min<br />MS (ESpos): m/z = 501 (M + H)$^+$ |

TABLE 2-continued

| Example | IUPAC name/structure (Yield) | Analytical data |
|---|---|---|
| 30 | rac-N-[(4-chlorophenyl)(cyano)methyl]-8-[(3,5-difluoropyridin-4-yl)methoxy]-2,6-dimethylimidazo[1,2-a]pyridine-3-carboxamide<br />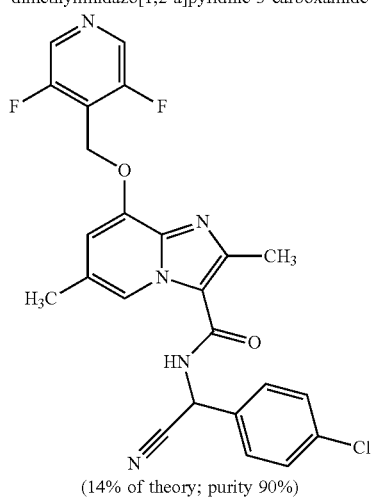<br />(14% of theory; purity 90%) | LC-MS (Method 1): $R_t$ = 0.97 min<br />MS (ESpos): m/z = 482 (M + H)$^+$ |
| 31 | rac-N-[(4-chlorophenyl)(cyano)methyl]-8-[(3,3-difluorocyclobutyl)methoxy]-2,6-dimethylimidazo[1,2-a]pyridine-3-carboxamide<br />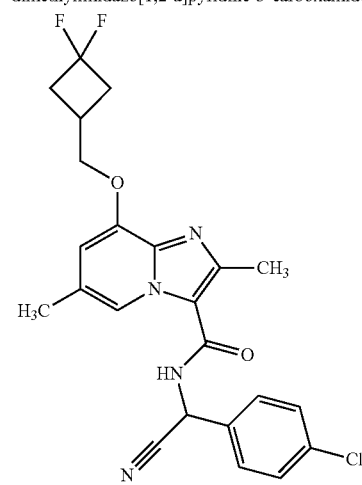<br />(6% of theory) | LC-MS (Method 1): $R_t$ = 1.00 min<br />MS (ESpos): m/z = 459 (M + H)$^+$ |

[1] the starting material was Example 37A (enantiomer B)

Example 32

N-(3-Cyano-4-ethoxyphenyl)-8-[(2,6-difluorobenzyl)oxy]-2,6-dimethylimidazo[1,2-a]pyridine-3-carboxamide

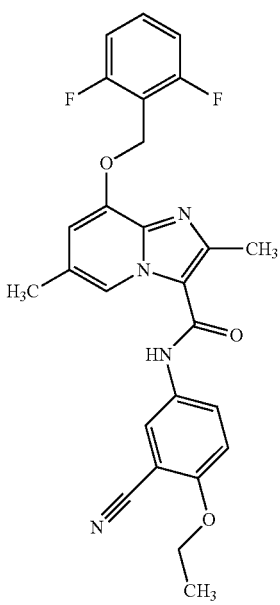

16.2 mg (0.10 mmol) of 5-amino-2-ethoxybenzonitrile were initially charged in a 96-well deep-well multititre plate. A solution of 33 mg (0.10 mmol) of 8-[(2,6-difluorobenzyl)oxy]-2,6-dimethylimidazo[1,2-a]pyridine-3-carboxylic acid from Example 16A in 0.4 ml of DMF and a solution of 45.6 mg (0.12 mol) of HATU in 0.4 ml of DMF were successively added thereto. After adding 20.2 mg (0.20 mmol) of 4-methylmorpholine, the mixture was shaken at RT overnight. Then the mixture was filtered and the target compound was isolated from the filtrate by preparative LC-MS (Method 11). The product-containing fractions were concentrated under reduced pressure using a centrifugal dryer. The residue of each product fraction was dissolved in 0.6 ml of DMSO. These were combined and finally freed of the solvent in a centrifugal dryer. This gave 9 mg (18% of theory) of the target compound.

LC-MS (Method 12): $R_t$=1.06 min

MS (ESpos): m/z=477 (M+H)$^+$

In analogy to Example 32, the example compounds shown in Table 3 were prepared by reacting the appropriate carboxylic acids with the appropriate amines, which are commercially available or have been described above, under the conditions described:

TABLE 3

| Example | IUPAC name/structure (Yield) | Analytical data |
| --- | --- | --- |
| 33 | N-(4-cyano-1H-pyrazol-5-yl)-8-[(2,6-difluorobenzyl)oxy]-2,6-dimethylimidazo[1,2-a]pyridine-3-carboxamide | LC-MS (Method 12): $R_t$ = 1.05 min<br>MS (ESpos): m/z = 423 (M + H)$^+$ |
| | (20% of theory) | |

TABLE 3-continued

| Example | IUPAC name/structure (Yield) | Analytical data |
|---|---|---|
| 34 | rac-N-(2-amino-1-cyan-2-oxoethyl)-8-[(2,6-difluorobenzyl)oxy]-2,6-dimethylimidazo[1,2-a]pyridine-3-carboxamide<br>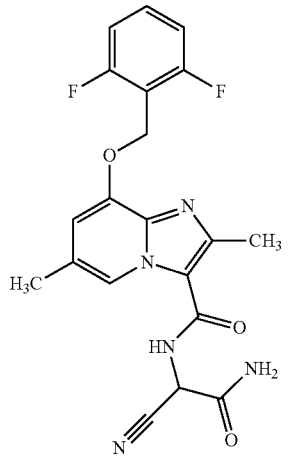<br>(35% of theory; purity 81%) | LC-MS (Method 12): $R_t$ = 0.83 min<br>MS (ESpos): m/z = 414 (M + H)$^+$ |
| 35 | N-[2-(cyanomethyl)phenyl]-8-[(2,6-difluorobenzyl)oxy]-2,6-dimethylimidazo[1,2-a]pyridine-3-carboxamide<br>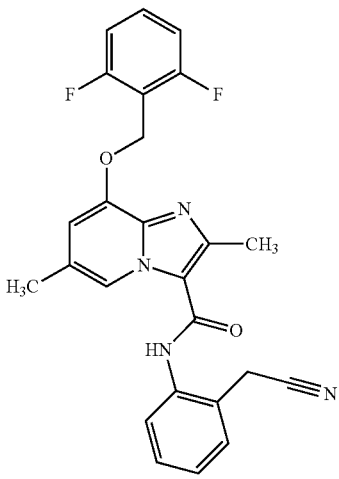 [SMILES: Cc1cc(OCc2c(F)cccc2F)c2nc(C)c(C(=O)Nc3ccccc3CC#N)n2c1]<br>(1% of theory) | LC-MS (Method 12): $R_t$ = 0.96 min<br>MS (ESpos): m/z = 447 (M + H)$^+$ |

TABLE 3-continued
| Example | IUPAC name/structure (Yield) | Analytical data |
|---|---|---|
| 36 | N-[4-(cyanomethyl)phenyl]-8-[(2,6-difluorobenzyl)oxy]-2,6-dimethylimidazo[1,2-a]pyridine-3-carboxamide 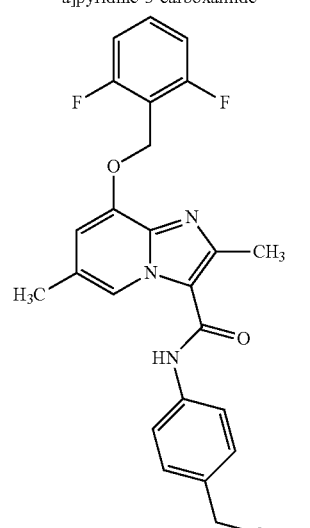 (34% of theory) | LC-MS (Method 12): $R_t$ = 0.97 min MS (ESpos): m/z = 447 (M + H)$^+$ |
| 37 | N-(3-cyano-4-methoxyphenyl)-8-[(2,6-difluorobenzyl)oxy]-2,6-dimethylimidazo[1,2-a]pyridine-3-carboxamide 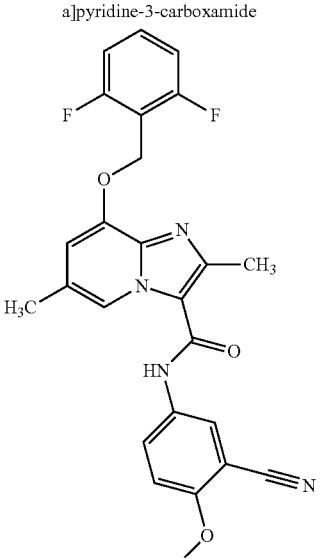 (25% of theory) | LC-MS (Method 12): $R_t$ = 1.01 min MS (ESpos): m/z = 463 (M + H)$^+$ |

Example 38

N-(5-Cyanopiperidin-3-yl)-8-[(2,6-difluorobenzyl)oxy]-2,6-dimethylimidazo[1,2-a]pyridine-3-carboxamide (Mixture of Stereoisomers)

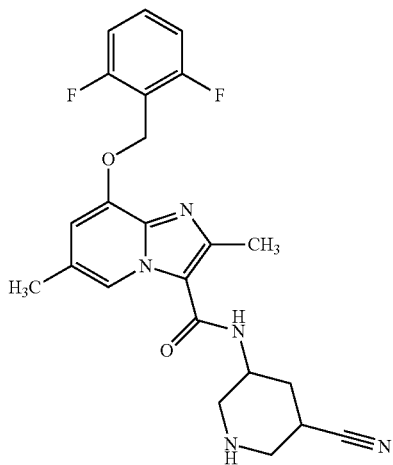 [SMILES: Cc1cc(OCc2c(F)cccc2F)c2nc(C)c(C(=O)NC3CNCC(C#N)C3)n2c1]

175 mg (0.23 mmol) of 9H-fluoren-9-ylmethyl-3-cyano-5-[({8-[(2,6-difluorobenzyl)oxy]-2,6-dimethylimidazo pyridin-3-yl}carbonyl)amino]piperidine-1-carboxylate trifluoroacetate (mixture of stereoisomers) from Example 66A were initially charged in 0.5 ml of DMF, 49 μl (0.50 mmol) of piperidine were added and the mixture was stirred at RT for 4 h. Acetonitrile/water and TFA were added and the reaction solution was purified by preparative HPLC (RP18 column, mobile phase: acetonitrile/water gradient with addition of 0.1% TFA). The product fractions were concentrated, taken up in dichloromethane and washed with saturated aqueous sodium bicarbonate solution. The aqueous phase was extracted twice with dichloromethane, the combined organic phases were dried over sodium sulphate and filtered and the filtrate was concentrated and lyophilized. This gave 67 mg of the target compound (67% of theory).

LC-MS (Method 1): $R_t$=0.56 min

MS (ESpos): m/z=440 (M+H)$^+$

Retention times of the stereoisomers: $R_t$=6.09 min and 13.02 min [Daicel Chiralpak AD-H, 5 μm, 250×4.6 mm, mobile phase: 50% isohexane, 50% isopropanol+0.2% diethylamine; flow rate: 1 ml/min; 40° C., detection: 220 nm].

Example 39 rac-N-(1-Amino-3-cyanopropan-2-yl)-8-[(2,6-difluorobenzyl)oxy]-2,6-dimethylimidazo[1,2-a]pyridine-3-carboxamide

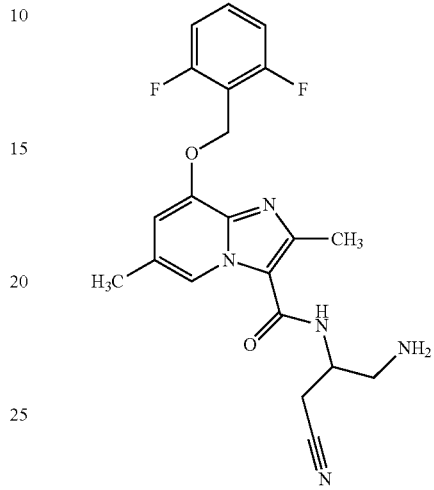

38 mg (0.07 mmol; purity about 85%) of rac-N-(1-azido-3-cyanopropan-2-yl)-8-[(2,6-difluorobenzyl)oxy]-2,6-dimethylimidazo[1,2-a]pyridine-3-carboxamide from Example 68A were dissolved in 4.6 ml of ethanol and 0.6 ml of DMF. 4 mg of palladium/carbon (10%) were added, and the mixture was hydrogenated at RT and under standard pressure for 1 h. Another 4 mg of palladium/carbon (10%) were added, and the mixture was hydrogenated at RT and under standard pressure for 0.5 h. The reaction solution was filtered through a Millipore filter and concentrated. The crude product was purified by thick-layer chromatography (mobile phase: dichloromethane/2N ammonia in methanol=20/1). This gave 6.6 mg of the target compound (21% of theory).

LC-MS (Method 1): $R_t$=0.57 min

MS (ESpos): m/z=414 (M+H)$^+$ $^1$H-NMR (400 MHz, DMSO-d$_6$): δ=1.75 (br. s, 2H), 2.32 (s, 3H), 2.67-2.84 (m, 3H), 2.92 (dd, 1H), 4.08-4.21 (m, 1H), 5.29 (s, 2H), 6.92 (s, 1H), 7.18-7.28 (m, 2H), 7.55-7.64 (m, 1H), 7.75-8.05 (m, 1H), 8.38 (s, 1H), [further signal under solvent peak].

Example 40

N-[(4-Cyanocyclohexyl)methyl]-8-[(3-cyclopropyl-2,6-difluorobenzyl)oxy]-2,6-dimethylimidazo[1,2-a]pyridine-3-carboxamide (Cis/Trans Mixture)

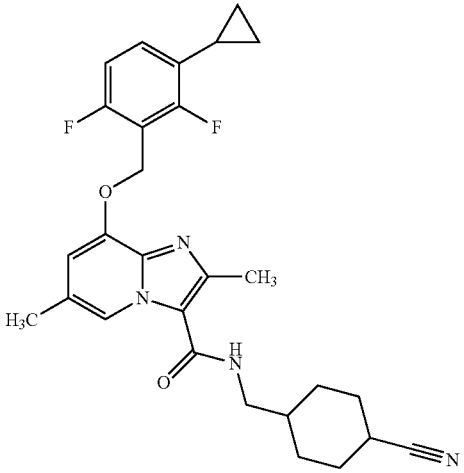 [SMILES: Cc1cc(OCc2c(F)ccc(C3CC3)c2F)c2nc(C)c(C(=O)NCC3CCC(C#N)CC3)n2c1]

30.5 mg (0.08 mmol) of HATU and 0.05 ml (0.31 mmol) of N,N-diisopropylethylamine to 30 mg (0.06 mmol) of 8-[(3-cyclopropyl-2,6-difluorobenzyl)oxy]-2,6-dimethylimidazo[1,2-a]pyridine-3-carboxylic acid trifluoroacetate from Example 57A in 0.2 ml of DMF. The mixture was stirred at RT for 20 min, 11 mg (0.08 mmol) of 4-(aminomethyl)cyclohexanecarbonitrile (cis/trans mixture) were then added and the mixture was stirred at RT for 1 hour. Water, TFA and acetonitrile were added and the reaction solution was purified by preparative HPLC (RP18 column, mobile phase: acetonitrile/water gradient with addition of 0.1% TFA). The product fractions were concentrated, taken up in dichloromethane and washed twice with saturated aqueous sodium bicarbonate solution. The aqueous phase was extracted twice with dichloromethane, the combined organic phases were dried over sodium sulphate and filtered and the filtrate was concentrated and lyophilized. This gave 20 mg of the target compound (65% of theory).

LC-MS (Method 1): $R_t$=0.96 and 0.97 min

MS (ESpos): m/z=493 (M+H)$^+$

Example 41 rac-N-(2-Amino-3-cyanopropyl)-8-[(2,6-difluorobenzyl)oxy]-2,6-dimethylimidazo[1,2-a]pyridine-3-carboxamide

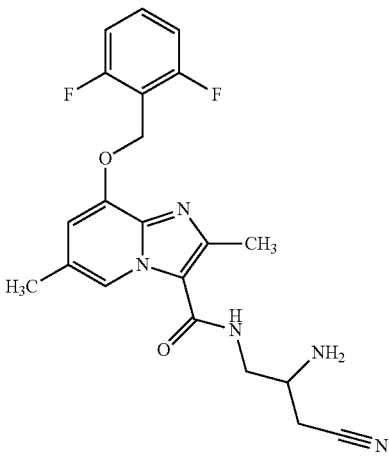 [SMILES: Cc1cc(OCc2c(F)cccc2F)c2nc(C)c(C(=O)NCC(N)CC#N)n2c1]

144 mg (0.21 mmol; purity about 95%) of rac-benzyl {1-cyano-3-[({8-[(2,6-difluorobenzyl)oxy]-2,6-dimethylimidazo[1,2-a]pyridin-3-yl}carbonyl)amino]propan-2-yl}carbamate trifluoroacetate from Example 73a were dissolved in 5.3 ml of ethanol. 7 mg of palladium/carbon (10%) were added, and the mixture was hydrogenated at RT and under standard pressure for 70 min. The reaction solution was filtered through a Millipore filter and concentrated. The residue was dissolved in dichloromethane/a little methanol, and washed twice with saturated aqueous sodium bicarbonate solution. The combined aqueous phases were extracted twice with dichloromethane. The combined organic phases were dried over sodium sulphate, filtered and concentrated. This gave 73 mg of the target compound (85% of theory).

LC-MS (Method 1): $R_t$=0.57 min

MS (ESpos): m/z=414 (M+H)$^+$ $^1$H-NMR (500 MHz, DMSO-$d_6$): δ=1.84 (br. s, 2H), 2.31 (s, 3H), 2.50-2.56 (m, 1H; superposed by solvent peak), 2.60-2.67 (m, 1H), 3.14-3.21 (m, 1H), 3.22-3.39 (m, 2H; superposed by solvent peak), 5.29 (s, 2H), 6.91 (s, 1H), 7.19-7.28 (m, 2H), 7.55-7.64 (m, 1H), 7.81 (t, 1H), 8.48 (s, 1H), [further signal under solvent peak].

Example 42 ent-N-(2-Amino-3-cyanopropyl)-8-[(2,6-difluorobenzyl)oxy]-2,6-dimethylimidazo[1,2-a]pyridine-3-carboxamide (Enantiomer A)

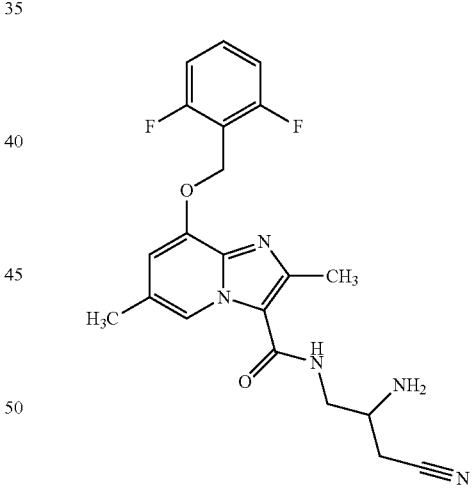

69 mg of Example 41 were separated into the enantiomers on a chiral phase [column: Daicel Chiralpak IF, 5 μm, 250×20 mm, mobile phase: 100% ethanol+0.2% diethylamine; flow rate: 15 ml/min; 40° C., detection: 220 nm]. The product fractions were collected on dry ice and then concentrated on a rotary evaporator at a bath temperature of 30° C. Acetonitrile and water were then added, and the product was lyophilized.

Yield: enantiomer A: 29 mg (99% ee)

enantiomer A: $R_t$=6.02 min [Daicel Chiralpak AZ-H, 5 μm, 250×4.6 mm, mobile phase: 100% ethanol+0.2% diethylamine; flow rate: 1 ml/min; 40° C., detection: 220 nm].

Example 43 ent-N-(2-Amino-3-cyanopropyl)-8-[(2,6-difluorobenzyl)oxy]-2,6-dimethylimidazo[1,2-a]pyridine-3-carboxamide (Enantiomer B)

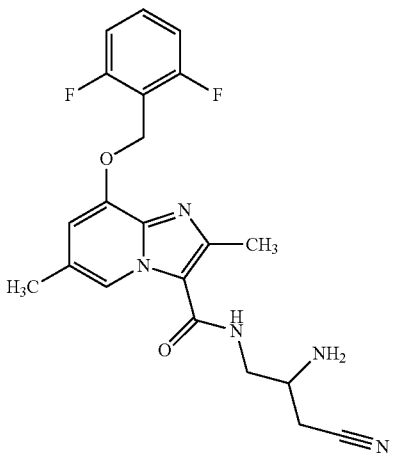 [SMILES: Cc1cc(OCc2c(F)cccc2F)c2nc(C)c(C(=O)NCC(N)CC#N)n2c1]

69 mg of Example 41 were separated into the enantiomers on a chiral phase [column: Daicel Chiralpak IF, 5 μm, 250×20 mm, mobile phase: 100% ethanol+0.2% diethylamine; flow rate: 15 ml/min; 40° C., detection: 220 nm]. The product fractions were collected on dry ice and then concentrated on a rotary evaporator at a bath temperature of 30° C. Acetonitrile and water were then added, and the product was lyophilized.

Yield: enantiomer B: 29 mg (90% ee)

enantiomer B: $R_t$=7.45 min [Daicel Chiralpak AZ-H, 5 μm, 250×4.6 mm, mobile phase: 100% ethanol+0.2% diethylamine; flow rate: 1 ml/min; 40° C., detection: 220 nm].

Example 44 rac-N-(2-Amino-4-cyanobutyl)-8-[(2,6-difluorobenzyl)oxy]-2,6-dimethylimidazo[1,2-a]pyridine-3-carboxamide

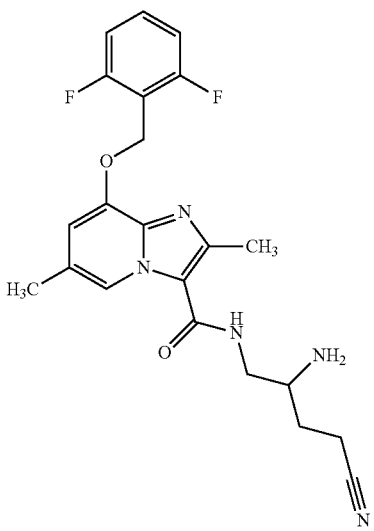 [SMILES: Cc1cc(OCc2c(F)cccc2F)c2nc(C)c(C(=O)NCC(N)CCC#N)n2c1]

78 mg (0.13 mmol, purity 96%) of rac-benzyl {4-cyano-1-[({8-[(2,6-difluorobenzyl)oxy]-2,6-dimethylimidazo[1,2-a]pyridin-3-yl}carbonyl)amino]butan-2-yl}carbamate from Example 80A were dissolved in 3.5 ml of ethanol, and 52 μl (0.67 mmol) of trifluoroacetic acid were added. 4.3 mg (0.004 mmol) of palladium on activated carbon (10%) were added, and the mixture was hydrogenated at RT and under standard pressure for 3.5 hours. The reaction solution was filtered and the filtrate was concentrated. The residue was dissolved in 3.5 ml of ethanol, and 52 μl (0.67 mmol) of trifluoroacetic acid were added. 4.3 mg (0.004 mmol) of palladium on activated carbon (10%) were added, and the mixture was hydrogenated at RT and under standard pressure for 1.5 hours. The reaction solution was filtered and the filtrate was concentrated. The residue was dissolved in dichloromethane and purified by thick-layer chromatography (mobile phase: dichloromethane/2N ammonia in methanol=10/0.5). This gave 16 mg (27% of theory, purity 95%) of the target compound.

LC-MS (Method 1): $R_t$=0.56 min

MS (ESpos): m/z=428 (M+H)$^+$ $^1$H-NMR (500 MHz, DMSO-$d_6$): δ=1.44-1.54 (m, 1H), 1.74-1.82 (m, 1H), 2.31 (s, 3H), 2.50 (s, 3H; superposed by solvent peak), 2.55-2.68 (m, 2H), 2.85-2.92 (m, 1H), 3.19-3.26 (m, 1H), 3.27-3.40 (2H, superposed by solvent peak), 5.29 (s, 2H), 6.91 (s, 1H), 7.20-7.27 (m, 2H), 7.55-7.63 (m, 1H), 7.81 (t, 1H), 8.45 (s, 1H), [further signal under solvent peak].

Example 45 rac-N-(2-Amino-5-cyanopentyl)-8-[(2,6-difluorobenzyl)oxy]-2,6-dimethylimidazo[1,2-a]pyridine-3-carboxamide

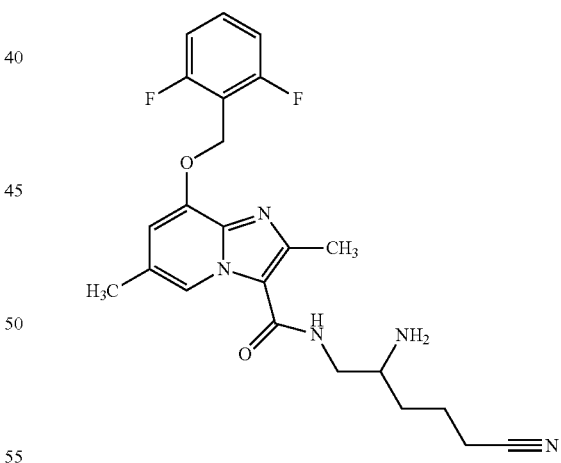

353 mg (0.49 mmol; purity 95%) of rac-benzyl {5-cyano-1-[({8-[(2,6-difluorobenzyl)oxy]-2,6-dimethylimidazo[1,2-a]pyridin-3-yl}carbonyl)amino]pentan-2-yl}carbamate trifluoroacetate from Example 81A were dissolved in 16.5 ml of ethanol. 0.19 ml of trifluoroacetic acid and 5.2 mg (0.005 mmol) of palladium on activated carbon (10%) were added, and the mixture was hydrogenated at RT and under standard pressure for 4.5 hours. The reaction solution was filtered through a Millipore filter and concentrated. The residue was purified by preparative HPLC (RP18 column, mobile phase: acetonitrile/water gradient with addition of 0.1% TFA). The product-containing fractions were combined and concentrated. The residue was dissolved in dichloromethane/a little methanol, and washed twice with saturated aqueous sodium bicarbonate solution. The combined aqueous phases were reextracted twice with dichloromethane. The combined organic phases were dried over sodium sulphate, filtered and concentrated. This gave 193 mg of the target compound (88% of theory).

LC-MS (Method 27): $R_t$=0.98 min

MS (ESneg): m/z=440 (M−H)⁻

$^1$H-NMR (400 MHz, DMSO-$d_6$): δ=1.24-1.35 (m, 1H), 1.47-1.68 (m, 4H), 1.68-1.81 (m, 1H), 2.31 (s, 3H), 2.50 (s, 3H; superposed by solvent peak), 2.77-2.86 (m, 1H), 3.10-3.19 (m, 1H), 3.23-3.39 (m, 2H; superposed by solvent peak), 5.29 (s, 2H), 6.91 (s, 1H), 7.19-7.28 (m, 2H), 7.54-7.63 (m, 1H), 7.76 (t, 1H), 8.46 (s, 1H), [further signal under solvent peak].

Example 46 ent-N-(2-Amino-5-cyanopentyl)-8-[(2,6-difluorobenzyl)oxy]-2,6-dimethylimidazo[1,2-a]pyridine-3-carboxamide (Enantiomer A)

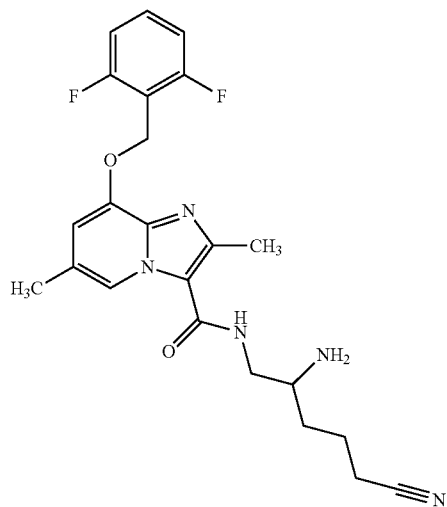 [SMILES: Cc1cc(OCc2c(F)cccc2F)c2nc(C)c(C(=O)NCC(N)CCCC#N)n2c1]

173 mg of Example 45 were separated into the enantiomers on a chiral phase [column: Daicel Chiralpak IF, 5 μm, 250×20 mm, mobile phase: 100% ethanol+0.2% diethylamine; flow rate: 15 ml/min; 40° C., detection: 220 nm]. The product fractions were collected on dry ice and then concentrated on a rotary evaporator at a bath temperature of 30° C. Acetonitrile and water were then added, and the product was lyophilized.

Yield: enantiomer A: 67 mg (98% ee)

enantiomer A: $R_t$=5.73 min [Daicel Chiralpak AZ-H, 5 μm, 250×4.6 mm, mobile phase: 100% ethanol+0.2% diethylamine; flow rate: 1 ml/min; 40° C., detection: 220 nm].

Example 47 ent-N-(2-Amino-5-cyanopentyl)-8-[(2,6-difluorobenzyl)oxy]-2,6-dimethylimidazo[1,2-a]pyridine-3-carboxamide (Enantiomer B)

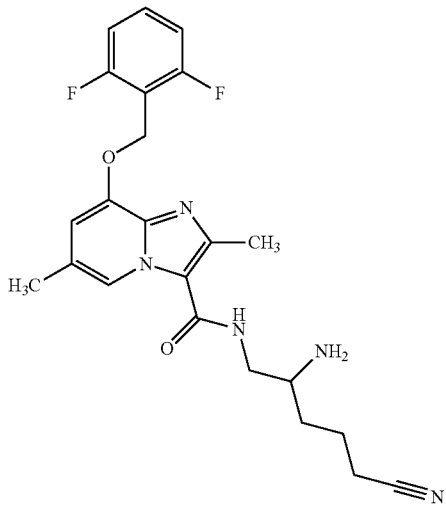 [SMILES: Cc1cc(OCc2c(F)cccc2F)c2nc(C)c(C(=O)NCC(N)CCCC#N)n2c1]

173 mg of Example 45 were separated into the enantiomers on a chiral phase [column: Daicel Chiralpak IF, 5 μm, 250×20 mm, mobile phase: 100% ethanol+0.2% diethylamine; flow rate: 15 ml/min; 40° C., detection: 220 nm]. The product fractions were collected on dry ice and then concentrated on a rotary evaporator at a bath temperature of 30° C. Acetonitrile and water were then added, and the product was lyophilized.

Yield: enantiomer A: 73 mg (89% ee)

enantiomer A: $R_t$=7.06 min [Daicel Chiralpak AZ-H, 5 μm, 250×4.6 mm, mobile phase: 100% ethanol+0.2% diethylamine; flow rate: 1 ml/min; 40° C., detection: 220 nm].

B. ASSESSMENT OF PHARMACOLOGICAL EFFICACY

The following abbreviations are used:
ATP adenosine triphosphate
Brij35 polyoxyethylene(23) lauryl ether
BSA bovine serum albumin
DTT dithiothreitol
TEA triethanolamine The pharmacological action of the compounds of the invention can be demonstrated in the following assays:

B-1. Measurement of sGC Enzyme Activity by Means of PPi Detection

Soluble guanylyl cyclase (sGC) converts GTP to cGMP and pyrophosphate (PPi) when stimulated. PPi is detected with the aid of the method described in WO 2008/061626. The signal that arises in the assay increases as the reaction progresses and serves as a measure of the sGC enzyme activity. With the aid of a PPi reference curve, the enzyme can be characterized in a known manner, for example in terms of conversion rate, stimulability or Michaelis constant.

Practice of the Test

To conduct the test, 29 μl of enzyme solution (0-10 nM soluble guanylyl cyclase (prepared according to Hönicka et al., Journal of Molecular Medicine 77 (1999) 14-23), in 50 mM TEA, 2 mM magnesium chloride, 0.1% BSA (fraction V), 0.005% Brij 35, pH 7.5) were initially charged in the microplate, and 1 µl of the stimulator solution (0-10 µM 3-morpholinosydnonimine, SIN-1, Merck in DMSO) was added. The microplate was incubated at RT for 10 min. Then 20 µl of detection mix (1.2 nM Firefly Luciferase (Photinus pyralis luciferase, Promega), 29 µM dehydroluciferin (prepared according to Bitler & McElroy, Arch. Biochem. Biophys. 72 (1957) 358), 122 µM luciferin (Promega), 153 µM ATP (Sigma) and 0.4 mM DTT (Sigma) in 50 mM TEA, 2 mM magnesium chloride, 0.1% BSA (fraction V), 0.005% Brij 35, pH 7.5) were added. The enzyme reaction was started by adding 20 µl of substrate solution (1.25 mM guanosine 5'-triphosphate (Sigma) in 50 mM TEA, 2 mM magnesium chloride, 0.1% BSA (fraction V), 0.005% Brij 35, pH 7.5) and analysed continuously in a luminometer.

B-2. Effect on a Recombinant Guanylate Cyclase Reporter Cell Line

The cellular activity of the compounds according to the invention is determined using a recombinant guanylate cyclase reporter cell line, as described in F. Wunder et al., Anal. Biochem. 339, 104-112 (2005).

Representative MEC values (MEC=minimum effective concentration) for the compounds of the invention are shown in the table below (in some cases as mean values from individual determinations):

TABLE A

| Example | MEC [µM] |
|---------|----------|
| 1 | 0.55 |
| 2 | 0.3 |
| 3 | 0.1 |
| 4 | 0.3 |
| 5 | 0.03 |
| 6 | 0.1 |
| 7 | 0.3 |
| 8 | 0.1 |
| 9 | 0.3 |
| 10 | 0.1 |
| 11 | 0.3 |
| 12 | 0.1 |
| 13 | 1 |
| 14 | 0.3 |
| 15 | 0.3 |
| 16 | 0.3 |
| 17 | 0.3 |
| 18 | 10 |
| 19 | 1 |
| 20 | 1 |
| 21 | 10 |
| 22 | 3 |
| 23 | 3 |
| 25 | 3 |
| 26 | 10 |
| 27 | 0.3 |
| 28 | 1 |
| 29 | 1 |
| 30 | 1 |
| 31 | 10 |
| 32 | 1 |
| 33 | 1 |
| 34 | 1 |
| 35 | 0.3 |
| 36 | 1 |
| 37 | 0.3 |
| 38 | 0.3 |
| 39 | 1 |
| 40 | 3 |
| 42 | 1 |
| 43 | 1 |
| 44 | 1 |

TABLE A-continued

| Example | MEC [µM] |
|---------|----------|
| 45 | 2 |
| 46 | 3 |
| 47 | 1 |

B-3. Vasorelaxant Effect In Vitro

Rabbits are stunned by a blow to the neck and exsanguinated. The aorta is removed, freed from adhering tissue and divided into rings of width 1.5 mm, which are placed individually under prestress into 5 ml organ baths with carbogen-sparged Krebs-Henseleit solution at 37° C. having the following composition (each mM): sodium chloride: 119; potassium chloride: 4.8; calcium chloride dihydrate: 1; magnesium sulphate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders. To generate a contraction, phenylephrine is added to the bath cumulatively in increasing concentration. After several control cycles, the substance to be studied is added in increasing dosage each time in every further run, and the magnitude of the contraction is compared with the magnitude of the contraction attained in the last preceding run. This is used to calculate the concentration needed to reduce the magnitude of the control value by 50% ($IC_{50}$ value). The standard administration volume is 5 µl; the DMSO content in the bath solution corresponds to 0.1%.

B-4. Blood Pressure Measurement on Anaesthetized Rats

Male Wistar rats having a body weight of 300-350 g are anaesthetized with thiopental (100 mg/kg i.p.). After tracheotomy, a catheter is introduced into the femoral artery to measure the blood pressure. The substances to be tested are administered as solutions, either orally by means of a gavage or intravenously via the femoral vein (Stasch et al. Br. J. Pharmacol. 2002; 135: 344-355).

B-5. Radiotelemetry Measurement of Blood Pressure in Conscious, Spontaneously Hypertensive Rats A commercially available telemetry system from DATA SCIENCES INTERNATIONAL DSI, USA, is employed for the blood pressure measurement on conscious rats described below.

The system consists of 3 main components:

implantable transmitters (Physiotel® telemetry transmitter)

receivers (Physiotel® receiver) which are linked via a multiplexer (DSI Data Exchange Matrix) to a data acquisition computer.

The telemetry system makes it possible to continuously record blood pressure, heart rate and body motion of conscious animals in their usual habitat.

Animal Material

The studies are conducted on adult female spontaneously hypertensive rats (SHR Okamoto) with a body weight of >200 g. SHR/NCrl from the Okamoto Kyoto School of Medicine, 1963, were a cross of male Wistar Kyoto rats having greatly elevated blood pressure and female rats having slightly elevated blood pressure, and were handed over at F13 to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6:00 am and at 7:00 pm.

Transmitter Implantation

The TA11 PA-C40 telemetry transmitters used are surgically implanted under aseptic conditions in the experimental animals at least 14 days before the first experimental use. The animals instrumented in this way can be used repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (Vet-BonD™, 3M). The transmitter housing is fixed intraperitoneally to the abdominal wall muscle, and the wound is closed layer by layer.

An antibiotic (Tardomyocel COMP, Bayer, 1 ml/kg s.c.) is administered postoperatively for prophylaxis of infection.

Substances and Solutions

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% tylose.

A solvent-treated group of animals is used as control.

Experimental Procedure

The telemetry measuring unit present is configured for 24 animals Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute values are corrected in the diagram with the currently measured barometric pressure (Ambient Pressure Reference Monitor; APR-1) and stored as individual data. Further technical details are given in the extensive documentation from the manufacturer company (DSI).

Unless indicated otherwise, the test substances are administered at 9:00 am on the day of the experiment. Following the administration, the parameters described above are measured over 24 hours.

Evaluation

After the end of the experiment, the acquired individual data are sorted using the analysis software (DATAQUEST™ A.R.T.™ ANALYSIS). The blank value is assumed here to be the time 2 hours before administration, and so the selected data set encompasses the period from 7:00 am on the day of the experiment to 9:00 am on the following day.

The data are smoothed over a predefinable period by determination of the average (15-minute average) and transferred as a text file to a storage medium. The measured values presorted and compressed in this way are transferred to Excel templates and tabulated. For each day of the experiment, the data obtained are stored in a dedicated file bearing the number of the experiment. Results and test protocols are stored in files in paper form sorted by numbers.

LITERATURE

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994.

B-6. Determination of Pharmacokinetic Parameters Following Intravenous and Oral Administration The pharmacokinetic parameters of the compounds according to the invention are determined in male CD-1 mice, male Wistar rats and female beagles. Intravenous administration in the case of mice and rats is effected by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The removal of blood from rats is simplified by inserting a silicone catheter into the right Vena jugularis externa prior to substance administration. The operation is effected at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it is stored at −20° C. until further processing.

An internal standard (which may also be a chemically unrelated substance) is added to the samples of the compounds of the invention, calibration samples and qualifiers, and there follows protein precipitation by means of acetonitrile in excess. Addition of a buffer solution matched to the LC conditions, and subsequent vortexing, is followed by centrifugation at 1000 g. The supernatant is analysed by LC-MS/MS using C18 reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, $t_{1/2}$ (terminal half-life), F (bioavailability), MRT (mean residence time) and CL (clearance), by means of a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. After centrifugation at 1000 g, the plasma concentration is measured (by means of LC-MS/MS; see above) and determined by calculating the ratio of the $C_{blood}/C_{plasma}$ value.

B-7. Metabolic Study

To determine the metabolic profile of the inventive compounds, they are incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The compounds of the invention were incubated with a concentration of about 0.1-10 µM. To this end, stock solutions of the compounds of the invention having a concentration of 0.01-1 mM in acetonitrile were prepared, and then pipetted with a 1:100 dilution into the incubation mixture. Liver microsomes and recombinant enzymes were incubated at 37° C. in 50 mM potassium phosphate buffer pH 7.4 with and without NADPH-generating system consisting of 1 mM NADP$^+$, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were stopped with acetonitrile (final concentration about 30%) and the protein was centrifuged off at about 15 000×g. The samples thus stopped were either analysed directly or stored at −20° C. until analysis.

The analysis is carried out by high-performance liquid chromatography with ultraviolet and mass spectrometry detection (HPLC-UV-MS/MS). To this end, the supernatants of the incubation samples are chromatographed with suitable C18 reversed-phase columns and variable eluent mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic reduction of the compound of the invention in the incubation mixtures.

B-8. Caco-2 Permeability Test

The permeability of a test substance was determined with the aid of the Caco-2 cell line, an established in vitro model for permeability prediction at the gastrointestinal barrier (Artursson, P. and Karlsson, J. (1991). Correlation between oral drug absorption in humans and apparent drug permeability coefficients in human intestinal epithelial (Caco-2) cells. Biochem. Biophys. 175 (3), 880-885). The Caco-2 cells (ACC No. 169, DSMZ, Deutsche Sammlung von Mikroorganismen and Zellkulturen, Braunschweig, Germany) were sown in 24-well plates having an insert and cultivated for 14 to 16 days. For the permeability studies, the test substance was dissolved in DMSO and diluted to the final test concentration with transport buffer (Hanks Buffered Salt Solution, Gibco/Invitrogen, with 19.9 mM glucose and 9.8 mM HEPES). In order to determine the apical to basolateral permeability ($P_{app}$A-B) of the test substance, the solution comprising the test substance was applied to the apical side of the Caco-2 cell monolayer, and transport buffer to the basolateral side. In order to determine the basolateral to apical permeability ($P_{app}$B-A) of the test substance, the solution comprising the test substance was applied to the basolateral side of the Caco-2 cell monolayer, and transport buffer to the apical side. At the start of the experiment, samples were taken from the respective donor compartment in order to ensure the mass balance. After an incubation time of two hours at 37° C., samples were taken from the two compartments. The samples were analysed by means of LC-MS/MS and the apparent permeability coefficients ($P_{app}$) were calculated. For each cell monolayer, the permeability of Lucifer Yellow was determined to ensure cell layer integrity. In each test run, the permeability of atenolol (marker for low permeability) and sulfasalazine (marker for active excretion) was also determined as quality control.

B-9. hERG Potassium Current Assay

The hERG (human ether-a-go-go related gene) potassium current makes a significant contribution to the repolarization of the human cardiac action potential (Scheel et al., 2011). Inhibition of this current by pharmaceuticals can in rare cases cause potentially lethal cardiac arrhythmia, and is therefore studied at an early stage during drug development.

The functional hERG assay used here is based on a recombinant HEK293 cell line which stably expresses the KCNH2(HERG) gene (Zhou et al., 1998). These cells are studied by means of the "whole-cell voltage-clamp" technique (Hamill et al., 1981) in an automated system (Patchliner™; Nanion, Munich, Germany), which controls the membrane voltage and measures the hERG potassium current at room temperature. The PatchControlHT™ software (Nanion) controls the Patchliner system, data capture and data analysis. The voltage is controlled by 2 EPC-10 quadro amplifiers controlled by the PatchMasterPro™ software (both: HEKA Elektronik, Lambrecht, Germany) NPC-16 chips with moderate resistance (~2 MΩ; Nanion) serve as the planar substrate for the voltage clamp experiments.

NPC-16 chips are filled with intra- and extracellular solution (cf. Himmel, 2007) and with cell suspension. After forming a gigaohm seal and establishing whole-cell mode (including several automated quality control steps), the cell membrane is clamped at the −80 mV holding potential. The subsequent voltage clamp protocol changes the command voltage to +20 mV (for 1000 ms), −120 mV (for 500 ms), and back to the −80 mV holding potential; this is repeated every 12 s. After an initial stabilization phase (about 5-6 minutes), test substance solution is introduced by pipette in rising concentrations (e.g. 0.1, 1, and 10 µmol/l) (exposure about 5-6 minutes per concentration), followed by several washing steps.

The amplitude of the inward "tail" current which is generated by a change in potential from +20 mV to −120 mV serves to quantify the hERG potassium current, and is described as a function of time (IgorPro™ Software). The current amplitude at the end of various time intervals (for example stabilization phase before test substance, first/second/third concentration of test substance) serves to establish a concentration/effect curve, from which the half-maximum inhibiting concentration $IC_{50}$ of the test substance is calculated.

Hamill O P, Marty A, Neher E, Sakmann B, Sigworth F J. Improved patch-clamp techniques for high-resolution current recording from cells and cell-free membrane patches. Pfluegers Arch 1981; 391:85-100.

Himmel H M. Suitability of commonly used excipients for electrophysiological in-vitro safety pharmacology assessment of effects on hERG potassium current and on rabbit Purkinje fiber action potential. J Pharmacol Toxicol Methods 2007; 56:145-158.

Scheel O, Himmel H, Rascher-Eggstein G, Knott T. Introduction of a modular automated voltage-clamp platform and its correlation with manual human ether-a-go-go related gene voltage-clamp data. Assay Drug Dev Technol 2011; 9:600-607.

Zhou Z F, Gong Q, Ye B, Fan Z, Makielski J C, Robertson G A, January C T. Properties of hERG channels stably expressed in HEK293 cells studied at physiological temperature. Biophys J 1998; 74:230-241.

C. WORKING EXAMPLES OF PHARMACEUTICAL COMPOSITIONS

The compounds of the invention can be converted to pharmaceutical preparations as follows:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed using a conventional tabletting press (see above for format of the tablet). The guide value used for the pressing is a pressing force of 15 kN.

Suspension for Oral Administration:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol; the compound of the invention is added to the suspension. The water is added while stirring. The mixture is stirred for about 6 h until the swelling of the Rhodigel is complete.

Solution for Oral Administration:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring operation is continued until dissolution of the compound of the invention is complete.

i.v. Solution:

The compound of the invention is dissolved in a concentration below the saturation solubility in a physiologically acceptable solvent (e.g. isotonic saline solution, glucose solution 5% and/or PEG 400 solution 30%). The resulting solution is subjected to sterile filtration and dispensed into sterile and pyrogen-free injection vessels.

The invention claimed is:
1. Compound of the formula (I)

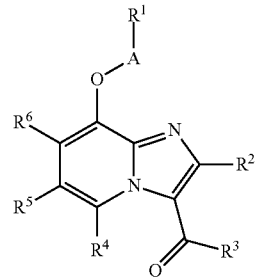

in which

A represents $CH_2$, $CD_2$ or $CH(CH_3)$, $R^1$ represents $(C_4-C_6)$-alkyl, $(C_3-C_7)$-cycloalkyl, pyridyl or phenyl,
  where $(C_4-C_6)$-alkyl may be up to hexasubstituted by fluorine,
  where $(C_3-C_7)$-cycloalkyl may be substituted by 1 to 4 substituents independently of one another selected from the group consisting of fluorine, trifluoromethyl and $(C_1-C_4)$-alkyl,
  and
  where phenyl may be substituted by 1 to 4 substituents independently of one another selected from the group consisting of halogen, cyano, monofluoromethyl, difluoromethyl, trifluoromethyl, $(C_1-C_4)$-alkyl, $(C_3-C_5)$-cycloalkyl, $(C_1-C_4)$-alkoxy, difluoromethoxy and trifluoromethoxy, or may be substituted on two adjacent carbon atoms in the phenyl by a difluoromethylenedioxy bridge,
  where pyridyl may be substituted by 1 to 4 substituents independently of one another selected from the group consisting of fluorine, monofluoromethyl, difluoromethyl, trifluoromethyl and $(C_1-C_4)$-alkyl, $R^2$ represents hydrogen, $(C_1-C_4)$-alkyl, cyclopropyl, monofluoromethyl, difluoromethyl or trifluoromethyl, $R^3$ represents a group of the formula

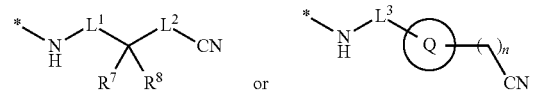

where

\* represents the point of attachment to the carbonyl group, $L^1$ represents a bond or $(C_1-C_4)$-alkanediyl,
  in which $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy, $L^2$ represents a bond or $(C_1-C_4)$-alkanediyl,
  in which $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy, $R^7$ represents hydrogen, $(C_1-C_6)$-alkyl, $(C_2-C_6)$-alkenyl, $(C_2-C_6)$-alkynyl, $(C_3-C_7)$-cycloalkyl, —(C=O)—$NR^9R^{10}$, $(C_1-C_4)$-alkoxycarbonyl, amino, hydroxy, 5- or 6-membered heteroaryl or phenyl, in which $(C_1-C_6)$-alkyl may be substituted by 1 to 3 substituents independently of one another selected from the group consisting of fluorine, trifluoromethyl, difluoromethoxy, trifluoromethoxy, hydroxy, $(C_3-C_7)$-cycloalkyl, $(C_1-C_4)$-alkoxy, $(C_1-C_4)$-alkoxycarbonyl, amino, phenyl, phenoxy and benzyloxy,
in which phenyl, phenoxy and benzyloxy for their part may be substituted by 1 to 3 substituents independently of one another selected from the group consisting of halogen and cyano,
in which $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
in which
$R^9$ represents hydrogen, $(C_1-C_6)$-alkyl or $(C_3-C_7)$-cycloalkyl,
$R^{10}$ represents hydrogen or $(C_1-C_6)$-alkyl,
and
in which phenyl and 5- or 6-membered heteroaryl may be substituted by 1 to 3 substituents independently of one another selected from the group consisting of halogen, cyano, trifluoromethyl, $(C_1-C_4)$-alkyl, $(C_1-C_4)$-alkoxy and $(C_1-C_4)$-alkylsulphonyl,
$R^8$ represents hydrogen or $(C_1-C_4)$-alkyl,
in which $(C_1-C_4)$-alkyl may be substituted by hydroxy, or
$R^7$ and $R^8$ together with the carbon atom to which they are bonded form a 3- to 7-membered carbocycle or a 4- to 7-membered heterocycle, in which the 3- to 7-membered carbocycle and the 4- to 7-membered heterocycle may in turn be substituted by 1 or 2 substituents independently of one another selected from the group consisting of fluorine and $(C_1-C_4)$-alkyl,
$L^3$ represents a bond or $(C_1-C_4)$-alkanediyl,
in which $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
n represents 0, 1 or 2,
the ring Q represents 3- to 7-membered carbocyclyl, 4- to 7-membered heterocyclyl, phenyl or 5- to 6-membered heteroaryl,
where the ring Q may be substituted by 1 to 3 substituents independently of one another selected from the group consisting of halogen, $(C_1-C_4)$-alkyl, trifluoromethyl, amino, hydroxy and $(C_1-C_4)$-alkoxy,
$R^4$ represents hydrogen,
$R^5$ represents hydrogen, halogen, cyano, monofluoromethyl, difluoromethyl, trifluoromethyl, $(C_1-C_4)$-alkyl, $(C_3-C_7)$-cycloalkyl, $(C_2-C_4)$-alkenyl, $(C_2-C_4)$-alkynyl, difluoromethoxy, trifluoromethoxy, $(C_1-C_4)$-alkoxy, amino, 4- to 7-membered heterocyclyl or 5- or 6-membered heteroaryl,
$R^6$ represents hydrogen, cyano or halogen,
and the N-oxides, salts, solvates, salts of the N-oxides and solvates of the N-oxides and salts thereof.

2. Compound of claim 1 in which
A represents $CH_2$ or $CH(CH_3)$,
$R^1$ represents $(C_4-C_6)$-alkyl, $(C_4-C_6)$-cycloalkyl, pyridyl or phenyl,
where $(C_4-C_6)$-alkyl may be up to hexasubstituted by fluorine,
where $(C_4-C_6)$-cycloalkyl may be substituted by 1 to 4 fluorine substituents, and
where phenyl may be substituted by 1 to 3 substituents independently of one another selected from the group consisting of fluorine, chlorine, cyano, trifluoromethyl, methyl, cyclopropyl, methoxy and ethoxy,
where pyridyl may be substituted by 1 or 2 substituents,
$R^2$ represents hydrogen, $(C_1-C_4)$-alkyl, cyclopropyl or trifluoromethyl,
$R^3$ represents a group of the formula

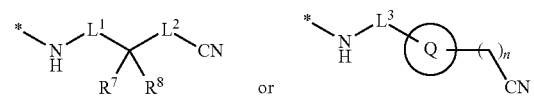

where
* represents the point of attachment to the carbonyl group,
$L^1$ represents a bond or $(C_1-C_4)$-alkanediyl,
in which $(C_1-C_4)$-alkanediyl may be substituted by 1 or 2 substituents independently of one another selected from the group consisting of fluorine, trifluoromethyl, methyl and ethyl,
$L^2$ represents a bond, methylene, ethylene or propylene,
$R^7$ represents hydrogen, $(C_1-C_6)$-alkyl, $(C_3-C_5)$-cycloalkyl, —(C=O)—$NR^9R^{10}$, amino or phenyl,
in which $(C_1-C_6)$-alkyl may be substituted by 1 to 3 substituents independently of one another selected from the group consisting of fluorine, trifluoromethyl, hydroxy, methoxy, ethoxy, amino and phenyl,
in which phenyl may be substituted by 1 to 3 fluorine substituents, in which $(C_3-C_5)$-cycloalkyl may be substituted by 1 or 2 fluorine substituents,
in which
$R^9$ represents hydrogen, $(C_1-C_4)$-alkyl, cyclopropyl or cyclobutyl,
$R^{10}$ represents hydrogen or $(C_1-C_4)$-alkyl,
and
in which phenyl may be substituted by 1 to 3 substituents independently of one another selected from the group consisting of fluorine, chlorine, cyano, trifluoromethyl, methyl, ethyl, methoxy and ethoxy,
$R^8$ represents hydrogen or $(C_1-C_4)$-alkyl,
or
$R^7$ and $R^8$ together with the carbon atom to which they are bonded form a 3- to 6-membered carbocycle,
in which the 3- to 6-membered carbocycle may be substituted by 1 or 2 fluorine substituents,
$L^3$ represents a bond, methylene or ethylene,
in which methylene and ethylene may be substituted by 1 or 2 substituents independently of one another selected from the group consisting of fluorine, methyl, ethyl and trifluoromethyl,
n represents 0 or 1,
the ring Q represents cyclopentyl, cyclohexyl, piperidinyl, piperazinyl, phenyl, pyrazolyl, pyridyl, oxazolyl, isoxazolyl, thiazolyl, oxadiazolyl or triazolyl,
in which the ring Q may be substituted by 1 or 2 substituents independently of one another selected from the group consisting of fluorine, chlorine, methyl, ethyl, trifluoromethyl, methoxy and ethoxy,
$R^4$ represents hydrogen,
$R^5$ represents hydrogen, fluorine, bromine, chlorine, cyano, methyl, ethyl, cyclopropyl, ethynyl, methoxy or ethoxy,
$R^6$ represents hydrogen or fluorine,
and the N-oxides, salts, solvates, salts of the N-oxides and solvates of the N-oxides and salts thereof.

3. Compound of claim 1 in which
A represents $CH_2$,
$R^1$ represents 3-methylbutyl,
  where 3-methylbutyl may be up to hexasubstituted by fluorine,
or
represents cyclohexyl,
  where cyclohexyl may be substituted by 2 fluorine substituents,
or
represents a phenyl group of the formula

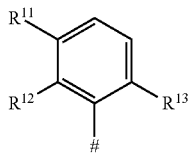

where
# represents the point of attachment to A,
and
$R^{11}$ represents hydrogen or fluorine,
$R^{12}$ and $R^{13}$ represent fluorine,
or
represents a pyridyl group of the formula

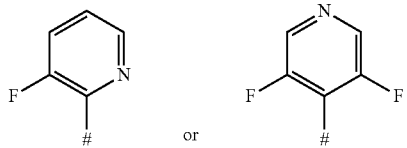

where
# represents the point of attachment to A,
$R^2$ represents methyl,
$R^3$ represents a group of the formula

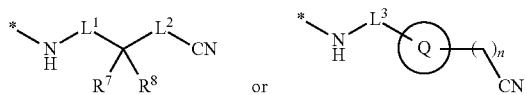

where
* represents the point of attachment to the carbonyl group,
$L^1$ represents a bond, methylene or ethylene,
$L^2$ represents a bond, methylene, ethylene or propylene,
$R^7$ represents hydrogen, methyl, ethyl, propyl, cyclopropyl, —(C=O)—$NR^9R^{10}$, amino or phenyl,
  in which methyl, ethyl and propyl may be substituted by hydroxy, methoxy, ethoxy or amino,
  in which cyclopropyl may be substituted by 1 or 2 fluorine substituents, in which
$R^9$ represents hydrogen,
$R^{10}$ represents hydrogen,
and
in which phenyl may be substituted by chlorine,
$R^8$ represents hydrogen or methyl,
or
$R^7$ and $R^8$ together with the carbon atom to which they are attached form a cyclopropyl ring or a cyclobutyl ring,
$L^3$ represents a bond or methylene,
n represents 0 or 1,
the ring Q represents cyclohexyl, piperidinyl, phenyl or pyrazolyl,
  in which the ring Q may be substituted by methoxy or ethoxy,
$R^4$ represents hydrogen,
$R^5$ represents hydrogen, chlorine, methyl, cyclopropyl or methoxy,
$R^6$ represents hydrogen,
and the N-oxides, salts, solvates, salts of the N-oxides and solvates of the N-oxides and salts thereof.

4. Compound of claim 1 in which
A represents $CH_2$,
$R^1$ represents a phenyl group of the formula

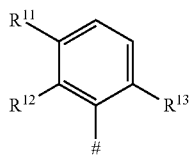

where
# represents the point of attachment to A,
and
$R^{11}$ represents hydrogen,
$R^{12}$ and $R^{13}$ represent fluorine,
$R^2$ represents methyl,
$R^3$ represents a group of the formula

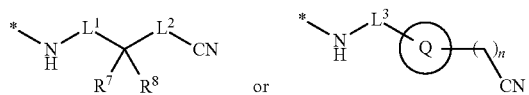

where
* represents the point of attachment to the carbonyl group,
$L^1$ represents a bond, methylene or ethylene,
$L^2$ represents a bond, methylene or ethylene,
$R^7$ represents hydrogen, methyl, ethyl, cyclopropyl, —(C=O)—$NR^9R^{10}$, amino or phenyl,
  in which methyl and ethyl may be substituted by hydroxy, methoxy, ethoxy or amino,
in which
$R^9$ represents hydrogen,
$R^{10}$ represents hydrogen,
and
in which phenyl may be substituted by chlorine,
$R^8$ represents hydrogen or methyl,
or
$R^7$ and $R^8$ together with the carbon atom to which they are attached form a cyclopropyl ring or a cyclobutyl ring, $L^3$ represents a bond or methylene, n represents 0 or 1, the ring Q represents cyclohexyl, piperidin-3-yl, phenyl or 1H-pyrazol-5-yl, in which phenyl may be substituted by methoxy or ethoxy, $R^4$ represents hydrogen, $R^5$ represents hydrogen, chlorine, methyl or methoxy, $R^6$ represents hydrogen, and the N-oxides, salts, solvates, salts of the N-oxides and solvates of the N-oxides and salts thereof.

5. Process for preparing the compound of claim 1, wherein

[A] a compound of the formula (II)

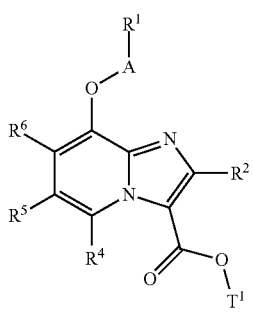
(II)

in which A, $R^1$, $R^2$, $R^4$, $R^5$ and $R^6$ are each as defined above and $T^1$ represents ($C_1$-$C_4$)-alkyl or benzyl, is reacted in an inert solvent in the presence of a suitable base or acid to give a carboxylic acid of the formula (III)

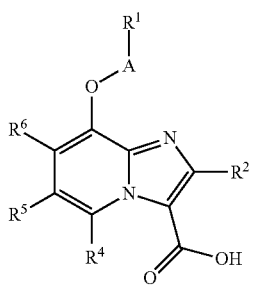
(III)

in which A, $R^1$, $R^2$, $R^4$, $R^5$ and $R^6$ each have the meanings given above, and this is subsequently reacted in an inert solvent under amide coupling conditions with an amine of the formula (IV-A) or (IV-B)

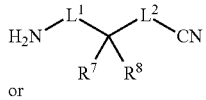
(IV-A)

or

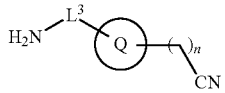
(IV-B)

in which n, $L^1$, $L^2$, $L^3$, Q, $R^7$ and $R^8$ each have the meanings given above, or

[B] a compound of the formula (III-B)

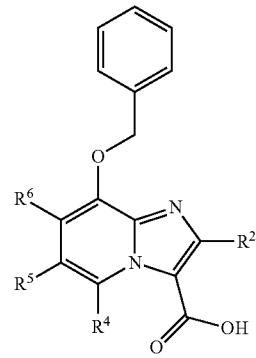
(III-B)

in which $R^2$, $R^4$, $R^5$ and $R^6$ each have the meanings given above, is reacted in an inert solvent under amide coupling conditions with an amine of the formula (IV) to give a compound of the formula (I-A) and (I-B)

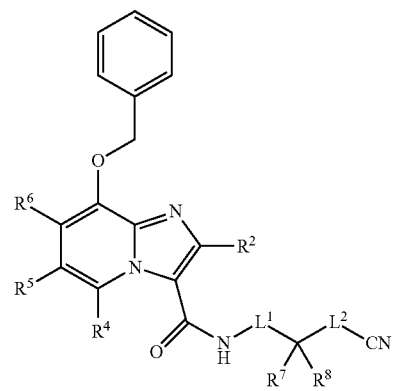
(I-A)

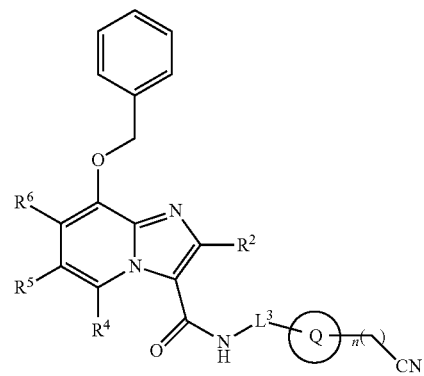
(I-B)

in which $R^2$, $R^4$, $R^5$, $R^6$, n, $L^1$, $L^2$, $L^3$, Q, $R^7$ and $R^8$ each have the meanings given above, and the benzyl group is subsequently detached therefrom by the methods known to the person skilled in the art and the resulting compound of the formula (V-A) or (V-B)

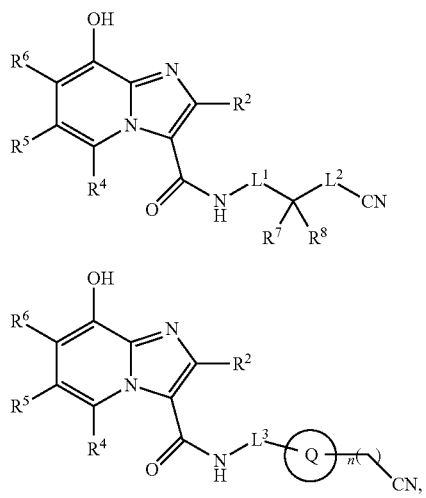

in which $R^2$, $R^4$, $R^5$, $R^6$, n, $L^1$, $L^2$, $L^3$, Q, $R^7$ and $R^8$ each have the meanings given above, is reacted in an inert solvent in the presence of a suitable base with a compound of the formula (VI)

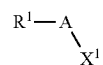

in which A and $R^1$ have the meaning given above and $X^1$ represents a suitable leaving group, in particular chlorine, bromine, iodine, mesylate, triflate or tosylate, pthen any protective groups present are detached, and the resulting compounds of the formula (I) are optionally converted with the appropriate (i) solvents and/or (ii) acids or bases to the solvates, salts and/or solvates of the salts thereof.

6. Medicament comprising the compound of claim 1 in combination with an inert, non-toxic, pharmaceutically suitable excipient.

7. Medicament comprising the compound of claim 1 in combination with a further active compound selected from the group consisting of organic nitrates, NO donors, cGMP-PDE inhibitors, antithrombotic agents, hypotensive agents and lipid metabolism modifiers.

* * * * *